(12) United States Patent
Reardon et al.

(10) Patent No.: US 7,858,341 B2
(45) Date of Patent: Dec. 28, 2010

(54) FGF18 PRODUCTION IN PROKARYOTIC HOSTS

(75) Inventors: Brian J. Reardon, Seattle, WA (US); Susan H. Julien, Seattle, WA (US); Chung-leung Chan, Sammamish, WA (US); Hong Y. Liu, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 11/301,383

(22) Filed: Dec. 12, 2005

(65) Prior Publication Data

US 2006/0172384 A1 Aug. 3, 2006

Related U.S. Application Data

(60) Provisional application No. 60/635,023, filed on Dec. 10, 2004.

(51) Int. Cl.
C12P 21/06 (2006.01)
C12N 1/20 (2006.01)
C12N 15/00 (2006.01)
C07H 21/04 (2006.01)
C07K 14/50 (2006.01)

(52) U.S. Cl. .................. 435/69.1; 536/23.5; 435/320.1; 435/252.8; 530/412; 530/416; 530/417

(58) Field of Classification Search .................. None
See application file for complete search history.

(56) References Cited

U.S. PATENT DOCUMENTS

| | | | |
|---|---|---|---|
| 5,439,818 A | 8/1995 | Fiddes et al. | |
| 5,514,566 A | 5/1996 | Fiddes et al. | |
| 5,604,293 A | 2/1997 | Fiddes et al. | |
| 5,989,866 A * | 11/1999 | Deisher et al. | ............. 435/69.4 |
| 6,013,477 A | 1/2000 | Greene et al. | |
| 6,352,971 B1 | 3/2002 | Deisher et al. | |
| 6,518,236 B1 | 2/2003 | Deisher et al. | |
| 7,135,459 B2 | 11/2006 | Deisher et al. | |
| 7,247,608 B2 | 7/2007 | Deisher et al. | |
| 7,563,438 B2 | 7/2009 | Deisher et al. | |
| 7,671,020 B2 | 3/2010 | Deisher et al. | |
| 2003/0008351 A1 | 1/2003 | Deisher et al. | |
| 2005/0043234 A1 | 2/2005 | Deisher et al. | |

FOREIGN PATENT DOCUMENTS

| WO | WO01/39788 | 6/2001 |
|---|---|---|
| WO | WO2004/032849 | 4/2004 |
| WO | WO2004/047857 | 6/2004 |

OTHER PUBLICATIONS

Ellsworth et al., "Fibroblast growth factor-18 is a trophic factor for mature chondrocytes and their progenitors," *Osteoarthritis and Cartilage* 10(4):308-320, 2002.

Ellsworth et al., "Fibroblast Growth Factor-18 Reduced Infarct Volumes and Behavioral Deficits After Transient Occlusion of the Middle Cerebral Artery in Rats," *Stroke* 34:1507-1512, Jun. 2003.

Hu et al., "FGF-18, a Novel Member of the Fibroblash Growth Factor Family, Stimulates Hepatic and Intestinal Proliferation," *Molecular and Cellular Biology* 18(10):6063-6074, Oct. 1998.

Ayala et al., *Modern Genetics*, 1984, Benjamin/Cummings Publishing Company, 44, 46 and Glossary.

Bowie et al., "Deciphering the Message in Protein Sequences: Tolerance to Amino Acid Substitutions," *Science*, 1990, (247), 1306-1310.

Crossley, P.H. et al., "Roles for FGF8 in the induction, initiation, and maintenance of chick limb development," *Cell*, Jan. 12, 1996, 84(1), 127-136.

Doerks et al., "Protein annotation: detective work for function prediction," *Trends in Genetics*, Jun. 1998, (14,6), 248-250.

Goldfarb, M., "The fibroblast growth factor family," *Cell Growth Differ.*, Sep. 1990, 1(9), 439-445.

Long, C.S. et al., "A growth factor for cardiac myocytes is produced by cardiac nonmyocytes," *Cell Regul.*, Dec. 1991, 2(12), 1081-1095.

Mickle et al., "Genotype-phenotype relationships in cystic fibrosis," *Medical Clinics of North America*, May 2000, (84,3), 597-607.

Mikayama, T., "Molecular cloning and functional expression of a cDNA encoding glycosylation-inhibiting factor," *Proceedings of the National Academy of Sciences*, (90):10056-10060, 1993.

Ngo et al., *The Protein Folding Problem and Tertiary Structure*, 1994, Birkhauser, Boston, 491-495.

Ohbayashi et al., "Structure and expression of the mRNA encoding . . . , FGF-18," *Journal of Biological Chemistry*, 273(29), 18161-18164, Jul. 17, 1998.

Reifers et al., *Mechanisms of Development*, 2000, (99), 39-49.

Robson et al., *Introduction to Proteins and Protein Engineering*, 1986, Elsevier, New York, p. 41.

Voet et al., *Biochemistry*, John Wiley & Sons, Inc., 126-128 and 228-234, 1990.

Wells, "Additivity of Mutational Effects in Proteins," *Biochemistry*, 1990, (29,37), 8509-8517.

Yan et al., "Two-amino acid molecular switch in an epithelial morphogen that regulates binding to two distinct receptors," *Science*, 2000, (290), 523-527.

* cited by examiner

*Primary Examiner*—Marianne P Allen
(74) *Attorney, Agent, or Firm*—Woodcock Washburn LLP

(57) ABSTRACT

The expression vectors and methods using an *E. coli* expression system for the large scale production of FGF18 are described. The vectors utilize the FGF18 coding sequence with specific changes in nucleotides in order to optimize codons and mRNA secondary structure for translation in *E. coli*. Using the expression vectors, the FGF18 gene was produced in *E. coli* to a level of greater than 1 g/L in fed batch fermentation. Also included are OmpT deficient *E. coli* strains, as well as OmpT and fhuA negative strains transformed with an FGF18 expression vector.

41 Claims, 2 Drawing Sheets

FGF18 PRODUCTION IN PROKARYOTIC HOSTS

This application claims the benefit of U.S. Provisional Application Ser. No. 60/635,023, filed Dec. 10, 2004, which is herein incorporated by reference.

BACKGROUND OF THE INVENTION

The increased availability and identification of genes from human and other genomes has led to an increased need for efficient expression and purification of recombinant proteins. The expression of proteins in bacteria is by far the most widely used approach for the production of cloned genes. For many reasons, expression in bacteria is preferred to expression in eukaryotic cells. For example, bacteria are much easier to grow than eukaryotic cells. More specifically, the availability of a wealth of sophisticated molecular genetic tools and thousands of mutants make *E. coli*, as an expression host, extremely useful for protein production. However, the high-level production of functional proteins in *E. coli.*, especially those from eukaryotic sources has often been difficult.

FGF18 is a member of the fibroblast growth factor family that shares significant sequence homology with FGF8 and FGF17. These three factors are thought to comprise a subfamily of the FGF proteins. As with all members of the FGF family, FGF18 has discrete effects on both developing and adult tissues and is thought to play a part in embroyonic development and wound healing (see, e.g., Ornitz and Marie, *Genes & Development,* 16:1446-1465 (discussing the role of all FGFs, including FGF18 in bone development)). In particular, FGF18 has been shown to have proliferative effects on cartilage and neural tissues, among others (Ellsworth et al., *Osteoarthritis and Cartilage* (2002) 10, 308-320; Ellsworth et al. *Stroke* (2003) 34(6): 1507-12).

Recombinant FGF18 has been produced in prokaryotic cells, in particular *E. coli*. The resulting bacterial produced protein is not glycosylated and is produced in an aggregated state. Initial experiments indicated that FGF18 produced in bacterial resulted in truncation of the protein, producing truncated FGF18 (trFGF18). As the truncated version appeared to have very similar, if not identical, biological properties as the full-length protein, constructs were then made that produced solely the truncated version. Production of FGF18 or trFGF18 from *E. coli* requires that the aggregated proteins be solubilized from the insoluble inclusion bodies and renatured or refolded. Without renaturation, the specific activity of the recombinant protein will be significantly reduced.

Despite advances in the expression of recombinant proteins in bacterial hosts, there exists a need for improved methods for producing biologically active and purified recombinant FGF18 and trFGF18 proteins in prokaryotic systems that result in higher yields for protein production. These and other aspects of the invention will become evident upon reference to the following detailed description. In addition, various references are identified below and are incorporated by reference in their entirety.

SUMMARY OF THE INVENTION

In one aspect, the present invention provides an expression vector for producing FGF18 or trFGF18 proteins comprising the operably linked elements of a prokaryotic origin of replication, a transcriptional initiation DNA element, and polynucleotide sequence and a transcriptional terminator. In another aspect, the expression vector is the vector pSDH170 (SEQ ID NO:1) that can be used to produce FGF18. In another aspect, the expression vector is pSDH174 (SEQ ID NO:2) that can be used to produce trFGF18. Further embodiments provide the expression vector can include a selectable marker.

In another aspect, the present invention provides prokaryotic host cells transformed the expression vectors described as comprising SEQ ID NO: 3:, a polynucleotide sequence encoding the polypeptide of SEQ ID NO:4, or vector pSDH170 (SEQ ID NO:1). In another aspect, the present invention provides prokaryotic host cells transformed the expression vectors described as comprising SEQ ID NO:5, a polynucleotide sequence encoding the polypeptide of SEQ ID NO:6, or vector pSDH174 (SEQ ID NO:2). In other embodiments, the host strain is *E. coli* strain W3110 or the strain zGOLD1 or zGOLD5.

In another aspect, the present invention provides methods for producing FGF18 or trFGF18 proteins under conditions wherein the FGF18 or trFGF18 protein is expressed. In one embodiment, the method comprises culturing a host cell expressing FGF18 after being transformed with pSDH170. In a second embodiment, the method comprises culturing a host cell expressing trFGF18 after being transformed with pSDH174. In other embodiments, the method comprising culturing a host cell transformed with an expression vector comprising SEQ ID NO:1. In further embodiments, the method comprising culturing a host cell transformed with an expression vector comprising SEQ ID NO:2. The method also comprises recovering the host cells from the growth medium, and then isolating the FGF18 or trFGF18 protein from the host cells.

In other aspects, the present invention provides methods for producing FGF18 or trFGF18 comprising the steps as described above, in a fed batch fermentation process or a batch fermentation process.

In another aspect, the present invention provides methods for producing an FGF18 or trFG18 protein comprising culturing a host cell as described above in a shake flask to an $OD_{600}$ of 5 to 20 in a growth medium, inoculating a fermentation vessel with 1 to 12% volume to volume (v/v) of shake flask medium containing host cells, culturing the host cells in a growth medium at a pH of 6.2 to 7.2, where a feed solution is fed into the fermentation vessel before 15 hours elapsed fermentation time (EFT), adding an inducing agent to the fermentation vessel at 20 to 30 hours EFT, and harvesting the host cells at 48 to 56 hours EFT. In one embodiment, the inducing agent is isopropyl β-D thiogalactopyranoside (IPTG) at 0.5 to 2 mM. In another embodiment, the feed solution comprises a carbohydrate selected from the group consisting of glycerol and glucose and the feed is 5 to 15 grams of carbohydrate per hour. In another embodiment, the glycerol in the feed solution is 40 to 70% v/v glycerol or the glucose is 40 to 70% w/v glucose. In further embodiments, the glycerol is about 70% v/v or the glucose is about 60% w/v.

In one aspect, the present invention provides methods of producing FGF18 or trFGF18 comprising seeding a flask with an inoculum comprising an *E. coli* W3110 host cells expressing an FGF18 or trFGF18 polypeptide as shown in SEQ ID NO:4 or SEQ ID NO:6, or an *E. coli* W3110 host cell comprising pSDH170 or pSDH174 vector, wherein an FGF18 or trFGF18 polypeptide is expressed, and with growth medium comprising about 5 g/l glycerol, culturing the inoculum in a growth medium for 16 to 20 hours at about 30° C., transferring the cultured inoculum in growth medium to a batch fermentator at a concentration 0.5 to 5% v/v inoculum, fermenting the batch fermentation at about 37° C. and about pH 6.8 with about 2% glycerol, introducing a glucose feed at about 8 hours EFT of about 9.5 g glucose/liter/hour and continuing until end of a fermentation run, adding IPTG at about 24 hours EFT to final concentration of 0.5 to 2 mM, fermenting about 28 hours of IPTG, harvesting fermentation broth from the fermentor, adding an equal volume of water to the fermentation broth, and homogenizing and centrifuging to collect a cell pellet or cell slurry comprising FGF18 or trFGF18 protein material.

In another aspect, the present invention provides methods for isolating insoluble FGF18 or trFGF18 protein comprising a sequence of amino acid residues as shown in SEQ ID NO:4 or SEQ ID NO:6 comprising separating water insoluble FGF18 or trFGF18 protein from a cell pellet or slurry, dissolving the insoluble FGF18 or trFGF18 material in a chaotropic solvent, diluting the chaotropic solvent and refolding the FGF18 or trFGF18 protein; and isolating the FGF18 or trFGF18 protein, wherein the isolated protein is capable of being biologically active. In one embodiment of the invention, the isolated FGF18 or trFGF18 protein is at least 90% pure. In another embodiment, the isolated FGF18 or trFGF18 protein is at least 90% pure and has an endotoxin level of less that 10 endotoxin units per mg FGF18 or trFGF18 protein.

In another aspect, the present invention provides methods for isolating insoluble FGF18 or trFGF18 protein comprising a sequence of amino acid residues as shown in SEQ ID NO:4 or SEQ ID NO:6 comprising separating from a fermentation broth a cell pellet or cell slurry comprising water insoluble FGF18 or trFGF18 protein material, homogenizing the cell pellet or cell slurry to collect inclusion bodies, dissolving the insoluble FGF18 or trFGF18 protein material in a chaoptropic solvent comprising a guanidine salt, diluting the chaotropic solvent by addition of a refolding buffer, isolating the FGF18 or trFGF18 protein by removing unfolded and aggregated proteins by filtering, and purifying the FGF18 or trFGF18 refolded protein on a cation exchange column, wherein the isolated and purified FGF18 or trFGF18 protein is capable of being biologically active.

In another aspect, the present invention provides a method for isolating insoluble FGF18 or trFGF18 protein comprising a sequence of amino acid residues as shown in SEQ ID NO:4 or SEQ ID NO:6 comprising separating from a fermentation broth a cell pellet or cell slurry comprising water insoluble FGF18 or trFGF18 material, homogenizing the cell pellet or cell slurry to collect inclusion bodies, dissolving the insoluble FGF18 or trFGF18 protein material in a chaotropic solvent comprising a guanidine salt, diluting the chaotropic solvent by addition of a refolding buffer, isolating the FGF18 or trFGF18 protein by removing unfolded and aggregated proteins by filtering, purifying the FGF18 or trFGF18 refolded protein on a cation exchange column, and purifying the FGF18 or trFGF18 eluate on a hydrophobic interaction column, wherein the isolated and purified FGF18 or trFGF18 protein is capable of being biologically active.

In other embodiments, the above methods for isolating insoluble FGF18 or trFGF18 protein comprise measuring biological activity using an FGF18 receptor binding assays.

DESCRIPTION OF THE INVENTION

Figure 1:
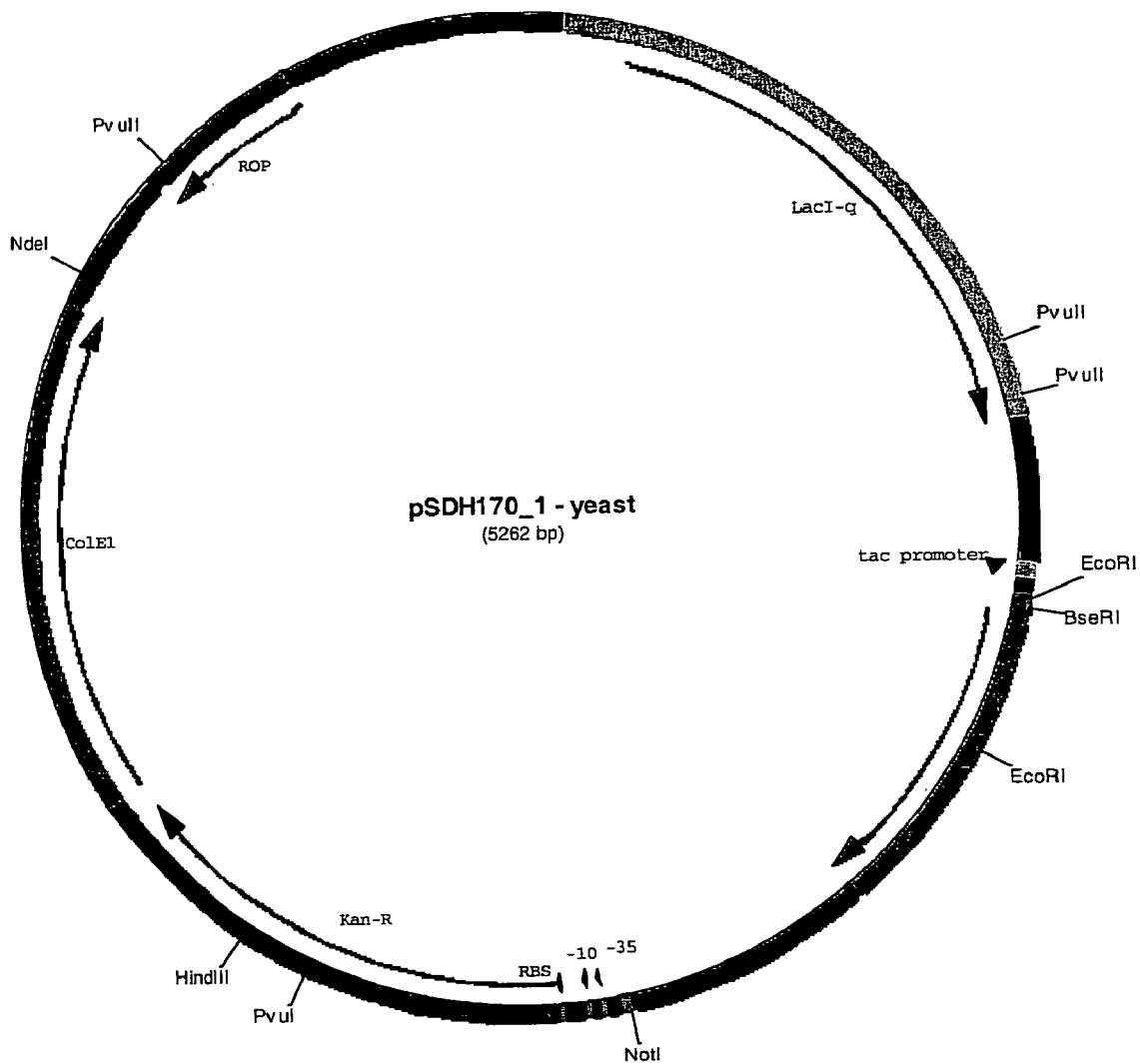
FIG. 1 is illustration of expression plasmid pSDH170, which comprises the codon optimized nucleotide sequence for FGF18.

The following definitions are provided to facilitate understanding of the invention.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

The term "complement of a nucleic acid molecule" refers to a nucleic acid molecule having a complementary nucleotide sequence and reverse orientation as compared to a reference nucleotide sequence.

An "enhancer" is a type of regulatory element that can increase the efficiency of transcription, regardless of the distance or orientation of the enhancer relative to the start site of transcription.

"Heterologous DNA" refers to a DNA molecule, or a population of DNA molecules, that does not exist naturally within a given host cell. DNA molecules heterologous to a particular host cell may contain DNA derived from the host cell species (i.e., endogenous DNA) so long as that host DNA is combined with non-host DNA (i.e., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

The term "contig" denotes a nucleic acid molecule that has a contiguous stretch of identical or complementary sequence to another nucleic acid molecule. Contiguous sequences are said to "overlap" a given stretch of a nucleic acid molecule either in their entirety or along a partial stretch of the nucleic acid molecule.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a cDNA molecule synthesized from an RNA template.

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

"Linear DNA" denotes non-circular DNA molecules with free 5' and 3' ends. Linear DNA can be prepared from closed circular DNA molecules, such as plasmids, by enzymatic digestion or physical disruption.

A "promoter" is a nucleotide sequence that directs the transcription of a structural gene. Typically, a promoter is located in the 5' non-coding region of a gene, proximal to the transcriptional start site of a structural gene. Sequence elements within promoters that function in the initiation of transcription are often characterized by consensus nucleotide sequences. These promoters include, for example, but are not limited to, IPTG-inducible promoters, bacteriophage T7 promoters and bacteriophage $\lambda p_L$. See Sambrook et al., *Molecular Cloning: A Laboratory Manual*, 3rd ed., Cold Spring Harbor Laboratory Press, Cold Spring Harbor, N.Y., 2001. A typical promoter will have three components, consisting of consensus sequences at −35 and −10 with a sequence of between 16 and 19 nucleotides between them (Lisset, S. and Margalit, H., *Nucleic Acids Res.* 21: 1512, 1993). Promoters of this sort include the lac, trp, trp-lac (tac) and trp-lac(trc) promoters. If a promoter is an inducible promoter, then the rate of transcription increases in response to an inducing agent. In contrast, the rate of transcription is not regulated by an inducing agent if the promoter is a constitutive promoter. Repressible promoters are also known.

A "core promoter" contains essential nucleotide sequences for promoter function, including the start of transcription. By this definition, a core promoter may or may not have detectable activity in the absence of specific sequences that may enhance the activity or confer tissue specific activity.

A "regulatory element" is a nucleotide sequence that modulates the activity of a core promoter. For example, a eukaryotic regulatory element may contain a nucleotide sequence that binds with cellular factors enabling transcription exclusively or preferentially in particular cells, tissues, or organelles. These types of regulatory elements are normally associated with genes that are expressed in a "cell-specific," "tissue-specific," or "organelle-specific" manner. Bacterial promoters have regulatory elements that bind and modulate the activity of the core promoter, such as operator sequences that bind activator or repressor molecules.

A "cloning vector" is a nucleic acid molecule, such as a plasmid, cosmid, or, bacteriophage, which has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transformed with the cloning vector. Marker genes typically include genes that provide resistance to antibiotic.

An "expression vector" is a nucleic acid molecule encoding a gene that is expressed in a host cell. Typically, an expression vector comprises a transcriptional promoter, a gene, an origin of replication, a selectable marker, and a transcriptional terminator. Gene expression is usually placed under the control of a promoter, and such a gene is said to be "operably linked to" the promoter. Similarly, a regulatory element and a core promoter are operably linked if the regulatory element modulates the activity of the core promoter. An expression vector may also be known as an expression construct.

A "recombinant host" is a cell that contains a heterologous nucleic acid molecule, such as a cloning vector or expression vector.

The term "expression" refers to the biosynthesis of a gene product. For example, in the case of a structural gene, expression involves transcription of the structural gene into mRNA and the translation of mRNA into one or more polypeptides.

The term "secretory signal sequence" denotes a DNA sequence that encodes a peptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

A "polypeptide" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein. Proteins are defined herein in terms of their amino acid backbone structures; substituents such as carbohydrate groups and non-peptidic groups are generally not specified, but may be present nonetheless.

A peptide or polypeptide encoded by a non-host DNA molecule is a "heterologous" peptide or polypeptide.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

The terms "amino-terminal" or "N-terminal" and "carboxyl-terminal" or "C-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

A "fusion protein" is a hybrid protein expressed by a nucleic acid molecule comprising nucleotide sequences of at least two genes.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075 (1985); Nilsson et al., *Methods Enzymol.* 198:3 (1991)), glutathione S transferase (Smith and Johnson, *Gene* 67:31 (1988)), Glu-Glu affinity tag (Grussenmeyer et al., *Proc. Natl. Acad. Sci. USA* 82:7952 (1985)), substance P, FLAG peptide (Hopp et al., *Biotechnology* 6:1204 (1988)), streptavidin binding peptide, or other antigenic epitope or binding domain. See, in general, Ford et al., *Protein Expression and Purification* 2:95 (1991). DNA molecules encoding affinity tags are available from commercial suppliers (e.g., Pharmacia Biotech, Piscataway, N.J.).

The term "isotonic" is used herein for its conventional meaning, that is a tonicity equal to that of blood, equivalent to a 0.9% solution of NaCl. "An isotonic amount" of a salt is that amount required to make a solution isotonic or to produce an isotonic solution upon reconstitution of a lyophilized preparation.

Concentrations are specified herein in units of molarity or % w/v of liquid compositions. When the composition is in the form of a lyophilized powder, the concentrations of the respective components will be such as to provide the specified concentration on reconstitution of the powder.

Due to the imprecision of standard analytical methods, molecular weights and lengths of polymers are understood to be approximate values. When such a value is expressed as "about" X or "approximately" X, the stated value of X will be understood to be accurate to ±10%.

Expression of Recombinant FGF18 or TRFGF18

The present invention provides expression vectors and methods for producing recombinant FGF18 protein from a prokaryotic host. FGF18 was previously designated zfgf5, and is fully described in commonly assigned U.S. Pat. Nos. 5,989,866 6,518,236 and 6,352,971, incorporated herein by reference. In particular, the expression vectors and methods of the present invention comprise an *E. coli* expression system for the large scale production of FGF18 or trFGF18 utilizing the FGF18 or trFGF18 coding sequence with specific changes in nucleotides in order to optimize codons and mRNA secondary structure for translation in *E. coli*. Using the expression vectors and methods of the present invention, the FGF18 or trFGF18 gene was produced in *E. coli* to a level of greater than 1 g/L in fed batch fermentation. The present inventors found that use of the *E. coli* OmpT protease deficient strains like, for example, UT5600, as a production host overcame stability problems with FGF18 or trFGF18. In addition to full length FGF18, a different polypeptide can be produced, truncated FGF18 (trFGF18) that is the FGF18 coding sequence with a codon encoding an N-terminal Met added at the 5' end of the polynucleotide sequence at amino acid 27 (Glu) and truncated at amino acid 196 (Lys). The trFGF18 sequence is SEQ ID NO: 5. Using the expression vectors described herein significantly improved the yield of recombinant protein recovered from the bacteria. In another embodiment, to facilitate the development of high cell density fed-batch fermentation, another *E. coli* strain, W3110, was selected as a host for the large-scale production of FGF18 or trFGF18. This host strain is non-pathogenic and can grow to high cell density in minimally defined fermentation media. The productivity of FGF18 or trFGF18 in *E. coli* strain W3110 was comparable to that obtained in *E. coli* strain UT5600 when produced in shaker flask and batch fermentations.

The present invention also provides methods for recovering recombinant FGF18 or trFGF18 protein from a prokaryotic host when the protein is expressed by the host and found within the host cell as an unglycosylated, insoluble inclusion body. When the prokaryotic cell is lysed to isolate the inclusion bodies (also called refractile bodies), the inclusion bodies are aggregates of FGF18 or trFGF18. Therefore, the inclusion bodies must be disassociated and dissolved to isolate the FGF18 or trFGF18 protein, and generally this requires the use of a denaturing chaotropic solvent, resulting in recovering a polypeptide that must be refolded to have significant biological activity. Once the FGF18 or trFGF18 protein is refolded, the protein must be captured and purified. Thus, the present invention provides for methods for isolating insoluble FGF18 or trFGF18 protein from prokaryotic cells, dissolving the insoluble protein material in a chaotropic solvent, diluting the chaotropic solvent in such a manner that the FGF18 or trFGF18 protein is refolded and isolated. The present invention also includes methods for capturing the renatured FGF18 or trFGF18 from the dilute refold buffer using cation exchange chromatography, and purifying the refolded FGF18 or trFGF18 protein using hydrophobic interaction chromatography. Further purification can be achieved using anion exchange in binding assays using an FGF18 receptor and the like.

The human FGF18 gene encodes a polypeptide of 207 amino acids. The full length sequence includes a signal peptide of 27 amino acids, as shown in SEQ ID NOS: 3 and 4, and a mature protein of 180 amino acids comprising residue 28 (Glu) to residue 207 (Ala). Truncated FGF18 (trFGF18) comprises the fragment from residue 28 (Glu) to 196 (Lys) with an added N-terminal Met. The nucleotide sequence of SEQ ID NO: 3 (SEQ ID NO:1 nucleotides 1495-2040) and SEQ ID NO:5 (SEQ ID NO: 2 nucleotides 1494-2007) show codon optimized sequences that fall within the scope of the present invention.

Production of recombinant human FGF18 or trFGF18 which utilized a mammalian expression system produced approximately 20 mg/L of protein. Therefore, a more cost effective expression system was desirable for large-scale production of FGF18 or trFGF18. The *E. coli* system was found to be a better alternative for large-scale production. Expression in *E. coli* offers numerous advantages over other expression systems, particularly low development costs and high production yields.

Recombinant FGF18 or trFGF18 expressed in *E. coli* was isolated as insoluble inclusion bodies after cell breakage. In most cases inclusion bodies needed to be solublized in denaturing chaotropic solvent and the protein refolded by dilution of the chaotropic agent followed by purification. Proteins vary a great deal with respect to their optimal refolding environment. Factors that can affect the recovery of properly folded and biologically active material include: initial protein concentration, oxidative state, pH, excipients, salts, detergents, termperature, mode of refolding buffer addition and the like.

Examination of the codons used in the human FGF18 cDNA indicated that it contained an excess of the least frequently used codons in *E. coli*. Genes with a high content of rarely used codons tend to be expressed at a low level in *E. coli* (Kane, *Curr Opin Biotechnol.* 6(5):494-500, 1995). An additional concern relating to the expression of human FGF18 in *E. coli* was the occurrence of eight potential OmpT cleavage sites located in the FGF18 sequence. OmpT is an endopeptidase that specifically cleaves between two consecutive basic residues and the enzyme is active under denaturing conditions such as 8M urea and 6M guanidine-HCl (White et al., *J Biol. Chem.* 270(22):12990-4, 1995; Dekker et al., *Biochemistry* 40(6):1694-701, 2001). It appeared that the site closest to the C-terminal end of the protein was particularly susceptible to cleavage. This raises concerns for the stability of full length FGF18 in a cell extract from *E. coli* due to the proteolytic activity of OmpT.

Several laboratories have shown that the expression level of proteins whose genes contain rare codons can be dramatically improved when the level of certain rare tRNAs is increased within the host (Zdanovsky et al., *Appl Environ Microbiol.* 66(8):3166-73, 2000; Calderone et al., *J Mol. Biol.* 262(4):407-12; Kleber-Janke et al., *Protein Expr Purif.* 19(3): 419-24, 2000; You et al., *Biotechniques.* 27(5):950-4, 1999.) An alternative approach is engineering the nucleotide sequence to take advantage of the redundancy of the genetic code and no longer require the utilization of the rare codons. Because these rare codons were plentiful in FGF18, the present inventors re-synthesized both the FGF18 gene and the trFGF18 gene with more appropriate codons.

The present invention provides an expression vector comprising the coding sequence of FGF18 with codons optimized for translation in *E. coli*. It also provides an expression vector comprising the coding sequence of a truncated FGF18 with codons optimized for translation in *E. coli*. The synthetic gene encoding trFGF18 was obtained by overlap PCR. The final PCR product was introduced into an expression vector for expression under the control of the Tac promotor. An examination of the secondary structure of the trFGF18 cDNA revealed an exceptionally stable two hairpin structure. It was suspected that these hairpin loops were a structural element that would prevent efficient expression from the fully optimized sequence. Therefore, the hairpin structures were eliminated during the codon optimization process. The resulting gene was expressed in *E. coli* at high levels. Expression levels with the new expression construct increased to around 20% of total cell protein or 100 mg/L.

Expression vectors that are suitable for production of a desired protein in prokaryotic cells typically comprise (1) prokaryotic DNA elements coding for a bacterial origin for the maintenance of the expression vector in a bacterial host; (2) DNA elements that control initiation of transcription, such as a promoter; (3) DNA elements that control the processing of transcripts, such as a transcriptional terminator, and (4) a gene encoding a selectable marker, such as antibiotic resistance. The prokaryotic host cell produces FGF18 or trFGF18 upon introduction of an expression vector and addition of an appropriate inducer. Accordingly, the present invention contemplates expression vectors comprising a promoter, the FGF18 or trFGF18 optimized nucleotide sequence, and a terminator sequence. The exemplary optimized FGF18 nucleotide sequence is shown in SEQ ID NO:3, while the exemplary optimized trFGF18 sequence is shown in SEQ ID NO:5. In another embodiment, the expression vector further comprises a selectable marker. In one embodiment, the selectable marker is kanamycin resistance.

Expression vectors can also comprise nucleotide sequences that encode a peptide tag to aid in purification of the desired protein. Peptide tags that are useful for isolating recombinant polypeptides include, for example, polyHistidine tags (which have an affinity for nickel-chelating resin), c-myc tags, calmodulin binding protein (isolated with calmodulin affinity chromatography), substance P, the RYIRS tag (which binds with anti-RYIRS antibodies), the Glu-Glu tag, and the FLAG tag (which binds with anti-FLAG antibodies). See, for example, Luo et al., *Arch. Biochem. Biophys.* 329: 215 (1996), Morganti et al., *Biotechnol. Appl. Biochem.* 23:67 (1996), and Zheng et al., *Gene* 186:55 (1997). Nucleic acid molecules encoding such peptide tags are available, for example, from Sigma-Aldrich Corporation (St. Louis, Mo.).

One of ordinary skill in the art will be familiar with a multitude of molecular techniques for the preparation of the expression vector. For example, the FGF18 or trFGF18 polynucleotide can be prepared by synthesizing nucleic acid molecules using mutually priming, long oligonucleotides and the nucleotide sequences described herein (see, for example, Ausubel (1995) at pages 8-8 to 8-9). Established techniques using the polymerase chain reaction provide the ability to synthesize DNA molecules at least two kilobases in length (Adang et al., *Plant Molec. Biol.* 21:1131 (1993), Bambot et al., *PCR Methods and Applications* 2:266 (1993), Dillon et al., "Use of the Polymerase Chain Reaction for the Rapid Construction of Synthetic Genes," in *Methods in Molecular Biology, Vol. 15: PCR Protocols: Current Methods and Applications*, White (ed.), pages 263-268, (Humana Press, Inc. 1993), and Holowachuk et al., *PCR Methods Appl.* 4:299 (1995)).

Another method for constructing expression systems utilizes homologous recombination using a yeast system. See U.S. Pat. No. 6,207,442, Plasmid Construction by Homologous Recombination, incorporated herein by reference. The system provides a universal acceptor plasmid that can be used to clone a DNA encoding any polypeptide of interest, including polypeptide fusions. The system provides methods for preparing double stranded, circular DNA molecules comprising a region encoding a protein of interest. One or more donor DNA fragments encoding the protein of interest, i.e., FGF18 or trFGF18, are combined with an acceptor plasmid, a first DNA linker, and a second DNA linker in a *Saccharomyces cerevisiae* host cell whereby the donor DNA fragment is joined to the acceptor plasmid by homologous recombination of the donor DNA, acceptor plasmid, and linkers to form the closed, circular plasmid.

The nucleic acid molecules of the present invention can also be synthesized with "gene machines" using protocols such as the phosphoramidite method. If chemically-synthesized, double stranded DNA is required for an application such as the synthesis of a gene or a gene fragment, then each complementary strand is made separately. The production of short genes (60 to 80 base pairs) is technically straightforward and can be accomplished by synthesizing the complementary strands and then annealing them. For the production of longer genes (>300 base pairs), however, special strategies may be required, because the coupling efficiency of each cycle during chemical DNA synthesis is seldom 100%. To overcome this problem, synthetic genes (double-stranded) are assembled in modular form from single-stranded fragments that are from 20 to 100 nucleotides in length. For reviews on polynucleotide synthesis, see, for example, Glick and Pasternak, *Molecular Biotechnology. Principles and Applications of Recombinant DNA* (ASM Press 1994), Itakura et al., *Annu. Rev. Biochem.* 53:323 (1984), and Climie et al., *Proc. Nat'l Acad. Sci. USA* 87:633 (1990).

Examples of alternate techniques that can be used to prepare the FGF18 or trFGF18 gene and expression vector include, for example, restriction endonuclease digestion and ligation, and polymerase chain reaction, all of which are well known in the art.

A wide variety of selectable marker genes is available (see, for example, Kaufman, *Meth. Enzymol.* 185:487 (1990); Kaufman, *Meth. Enzymol.* 185:537 (1990)). It is common for expression vectors to comprise selection markers, such as tetracycline resistance, amplicillin resistance, kanamycin resistance, neomycin resistance, or chlormaphenicol resistance. A selectable marker will permit selection and/or detection of cells that have been transformed with expression vector from cells that have not been transformed. An expression vector can carry more than one such antibiotic resistance gene. An example of selectable marker without antibiotic resistance uses the hok/sok system from plasmid R1. The hok gene encodes the toxic Hok protein of 52 amino acids and the sok gene encodes an antisense RNA, which is complementary to the hok mRNA leader sequence. This selectable marker is known to one skilled in the art and is described in more detail by Gerdes, K. et al., *Genetic Engineering*, 19:49-61, 1997.

A wide variety of suitable recombinant host cells is encompassed by the present invention and includes, but is not limited to, gram-negative prokaryotic host organisms. Suitable strains of *E. coli* include W3110, K12-derived strains MM294, TG-1, JM-107, BL21, and UT5600. Other suitable strains include: BL21(DE3), BL21(DE3)pLysS, BL21(DE3) pLysE, DH1, DH4I, DH5, DH5I, DH5IF', DH5IMCR, DH10B, DH10B/p3, DH11S, C600, HB101, JM101, JM105, JM109, JM110, K38, RR1, Y1088, Y1089, CSH18, ER1451, ER1647, *E. coli* K12, *E. coli* K12 RV308, *E. coli* K12 C600, *E. coli*HB101, *E. coli* K12 C600 R.sub.k-M.sub.k-, *E. coli* K12 RR1 (see, for example, Brown (ed.), *Molecular Biology Labfax* (Academic Press 1991)). Other gram-negative prokaryotic hosts can include *Serratia, Pseudomonas, Caulobacter*. Prokaryotic hosts can include gram-positive organisms such as *Bacillus*, for example, *B. subtilis* and *B. thuringienesis*, and *B. thuringienesis* var. *israelensis*, as well as *Streptomyces*, for example, *S. lividans, S. ambofaciens, S. fradiae*, and *S. griseofuscus*. Suitable strains of *Bacillus subtilus* include BR151, YB886, MI119, MI120, and B170 (see, for example, Hardy, "Bacillus Cloning Methods," in *DNA Cloning: A Practical Approach*, Glover (ed.) (RL Press 1985)). Standard techniques for propagating vectors in prokaryotic hosts are well-known to those of skill in the art (see, for example, Ausubel et al. (eds.), *Short Protocols in Molecular Biology*, 3$^{rd}$ Edition (John Wiley & Sons 1995); Wu et al., *Methods in Gene Biotechnology* (CRC Press, Inc. 1997)). For an overview of protease deficient strains in prokaryotes, see, Meerman et al., *Biotechnology* 12:1107-1110, 1994. The present invention is exemplified using the W3110 strain, which has been deposited at the American Type Culture Collection (ATCC) as ATCC # 27325.

Techniques for manipulating cloned DNA molecules and introducing exogenous DNA into a variety of host cells are disclosed by Sambrook et al., Molecular Cloning: *A Laboratory Manual*, 2nd ed., Cold Spring Harbor Laboratory Press, Cold Spring Harbor, N.Y., 1989, and Ausubel et al., eds., *Current Protocols in Molecular Biology*, John Wiley and Sons, Inc., NY, 1987. Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient that is complemented by the selectable marker carried on the expression vector or co-transfected into the host cell. Liquid cultures are provided with sufficient aeration by conventional means, such as shaking of small flasks or sparging of fermentors. Transformed cells can be selected and propagated to provide recombinant host cells that express the gene of interest. FGF18 or trFGF18 can be expressed in *E. coli* using the MBP (maltose binding protein) fusion system (New England Biolabs (NEB; Beverly, Mass.)). In this system, the FGF18 or trFGF18 cDNA is attached to the 3' end of the malE gene to form an MBP-FGF18 or MBP-trFGF18 fusion protein. Fusion protein expression is driven by the tac promoter and is "off" until the promoter is induced by addition of 1 mmol IPTG. The constructs can be built as in-frame fusions with MBP in accordance with the Multiple Cloning Site (MCS) of the pMAL-c2 vector (NEB), and according to the manufacturer's specifications.

Fermentation

In one embodiment of the present invention a batch fermentation can be used, particularly when a large scale production of FGF18 or trFG18 using the expression system of the present invention is required. Generally, batch fermentation comprises that a first stage seed flask is prepared by growing *E. coli* strains expressing FGF18 or trFGF18 in a suitable medium in shake flask culture to allow for growth to an optical density (OD) of 5 to 20 at 600 nm. A suitable medium would contain nitrogen from a source(s) such as ammonium sulfate, ammonium phosphate, ammonium chloride, yeast extract, hydrolyzed animal proteins, hydrolyzed plant proteins or hydrolyzed caseins. Phosphate will be supplied from potassium phosphate, ammonium phosphate, phosphoric acid or sodium phosphate. Other components would be magnesium chloride or magnesium sulfate, ferric sulfate or ferric chloride, and other trace elements. Growth medium can be supplemented with carbohydrates, such as fructose, glucose, galactose, lactose, and glycerol, to improve growth. In certain embodiments, carbohydrate additions would be glycerol or glucose added from 1 to 20 g/L medium. In certain embodiments, the glycerol or glucose is 5-10 g/L. Growth is started by inoculating a shake flask (baffled flask from 500 ml to 2000 ml) containing a preferred growth medium with *E. coli* from an agar medium containing antibiotic, for example kanamycin at 10-50 μg/ml, at the appropriate concentration or from a frozen stock culture. Growth in the shake flasks is at a temperature between 28 and 40° C. In certain embodiments, the shake flasks are grown at 30 to 37° C. The flasks are incubated with agitation set at 200 to 300 rpm.

Fermentation vessels are prepared with a suitable growth medium and sterilized. The pH of the medium is adjusted to a pH 6.5 to 7.5. In certain embodiments, the pH is 6.8, 6.9, 7.0, 7.1 or 7.2. The vessels are set to the proper aeration and agitation levels and inoculated from a first stage seed flask culture that has been grown 10 to 20 hours and has an OD of 5 to 20 at 600 nm. The inoculation level is between 1% and 12% volume/volume (v/v). In certain embodiments, the inoculation level is at 3%, 4%, 5%, 6%, 7%, 8%, 9% or 10% v/v. The dissolved oxygen level is maintained above 20% saturation by increasing agitation speed, increasing the aeration rate, sparging in oxygen, or various combinations. The culture is grown until the OD 600 reaches 2 to 20 OD units. IPTG is then added to the culture to a concentration 0.1 to 2.0 mM. The IPTG induces the tac promoter to express the FGF18 or trFGF18. Alternatively, lactose at 30% solution can be added at 10 g/l at 24 hours for induction. The culture is then allowed to grow for an additional time between 2 and 8 hours. In certain embodiments, the culture is grown for 3-4 hours.

In another embodiment, a fed batch culture is used to generate a high yield of FGF18 or trFGF18 protein. The FGF18- or trFGF18-producing *E. coli* strains are grown in a suitable medium in shake flask culture to allow for growth to an OD of 5 to 20 at 600 nm. A suitable medium would contain nitrogen from a source(s) such as ammonium sulfate, ammonium phosphate, ammonium chloride, yeast extract, hydrolyzed animal proteins, hydrolyzed plant proteins or hydrolyzed caseins. Phosphate will be supplied from potassium phosphate, ammonium phosphate, phosphoric acid or sodium phosphate. Other components would be magnesium chloride or magnesium sulfate, ferric sulfate or ferric chloride, and other trace elements. Growth medium can be supplemented with carbohydrates such as fructose, glucose, galactose, lactose and glycerol, to improve growth. In certain embodiments, carbohydrate additions would be glycerol or glucose added from 1 to 40 g/L medium. In one embodiment, the glycerol or glucose is 5-10 g/L. Growth is started by inoculating a shake flask (baffled flask from 500 ml to 2000 ml) containing a preferred growth medium with *E. coli* from an agar medium containing kanamycin (10-50 µg/ml) or from a frozen stock culture. Growth in the shake flasks is at a temperature of 28 to 40° C. In certain embodiments, growth temperature is 30 to 37° C. The flasks are incubated with agitation set at 200 to 300 rpm.

A second stage vessel is prepared with a suitable growth medium and sterilized. A suitable medium would be, for example, Super Broth II (Becton Dickenson, Franklin Lakes, N.J.), APS-Super Broth, Luria Broth, or ZSM (see, Tables 1-4) and kanamycin. Growth medium can be supplemented with carbohydrates to improve growth. Certain embodiments provide carbohydrate additions that have glycerol or glucose added from 1 to 40 g/L medium. In one embodiment, glycerol or glucose is 5-10 g/L. The pH of the medium is adjusted to a pH of 6.5 to 7.5. In certain embodiments, the pH is 6.8, 6.9, 7.0, 7.1 or 7.2. The vessels are set to the proper aeration and agitation levels. Growth is started by inoculating the vessel from a first stage seed flask culture that has been grown 10 to 20 hours and has an OD of 5 to 20 at 600 nm. The inoculation level is 1% to 12% v/v. In certain embodiments, the induction level will be 3%, 4%, 5%, 6%, 7%, 8%, 9% or 10% v/v. The dissolved oxygen level is maintained above 20% saturation by increasing agitation speed, increasing the aeration rate, sparging in oxygen or various combinations thereof.

Fermentation vessels are prepared with a suitable growth medium (as described above) and sterilized. The pH of the medium is adjusted to a pH between 6.2, 6.3, 6.4, 6.5, 6.6, 6.7, 6.8, 6.9, 7.0, 7.1 or 7.2. In one embodiment, the medium is adjusted to pH 6.8. Growth medium can be supplemented with carbohydrates to improve growth. In some embodiments, carbohydrate additions are glycerol or glucose added from 5 to 40 g/L medium with certain embodiments having glycerol or glucose at 15-20 g/L. The vessels are set to the proper aeration and agitation levels and inoculated from a first stage seed flask culture or second stage seed vessel that has been grown to 10 to 20 hours and has an OD of 5 to 20 at 600 nm. The inoculation level is between 1% and 12% v/v. In certain embodiments, the inoculation level is 5%, 6%, 7%, 8%, 9% or 10% v/v. The dissolved oxygen level is maintained above 20% saturation by increasing agitation speed, increasing the aeration rate, sparging in oxygen or various combinations thereof.

A carbohydrate solution is fed into the fermentor at a pre-determined rate starting at the beginning of the fermentation run, but generally after 6 hours elapsed fermentation time (EFT), and no longer than 12 hours EFT. The feed is continued until the end of the fermentation. The feed solution can be glycerol prepared at 40-70% v/v or glucose prepared at 40-70% weight/volume (w/v). In certain embodiments, glycerol or glucose are prepared at 70% v/v glycerol and 60% w/v glucose. Feed rates can vary between 5-15 grams of glucose or glycerol per liter per hour. In one embodiment the feed rate is 8, 9, or 10 g/L/hr. At a time of 20 to 30 hours EFT, for example at 24 hours, IPTG is added to the culture to a concentration of 0.5 to 2 mM. Alternatively, lactose at 30% solution can be added at 10 g/l at 24 hours for induction. At a time of 48 to 56 hours EFT, the fermentation is harvested. Alternatively, an additional 0.5 to 2 mmol/L of IPTG is added to the fermentor culture. The fermentation is then harvested at 52 to 56 hours EFT.

At the end of the fermentation run the temperature is adjusted downward to from 4° to 20° C., and the pH is either maintained or adjusted to 5.0 to 9.0. In certain embodiments, the range is 6.0 to 8.0 pH units. The fermentation broth is harvested by over-pressurization of the vessel and collection of the broth through the sample port. Alternatively, the broth can be pumped out through one of the sample ports. The fermentation broth can contain 10%-30% w/v solids.

FGF18 or TRFGF18 Recovery

Following fermentation the cells are harvested by centrifugation, re-suspended in homogenization buffer and homogenized, for example, in an APV-Gaulin homogenizer (Invensys APV, Tonawanda, N.Y.) or other type of cell disruption equipment, such as bead mills and sonicators. Alternatively, the cells are taken directly from the fermentor and homogenized in an APV-Gaulin homogenizer. Alternatively, the fermentation broth may be diluted with water or buffer prior to homogenization.

In one embodiment, the cells are homogenized directly in the fermentation broth. For example, an APV-Gaulin 1000 or APV-Gaulin 2000 homogenizer is chilled to 4°-15° C. for at least 30 minutes. The fermentation broth is passed through the homogenizer and the cell suspension is collected. The homogenizer pressure should be set at 6000 to 14,000 psi for maximum cell disruption. In one embodiment, the pressure is set for 10,000 psi. The suspension is passed through the homogenizer between 1-5 times, for example, for 3 passes. In another embodiment, the broth is diluted with an equal volume of water prior to homogenization. The amount of DNA may be decreased by the addition of PEI, spermine or benzonase during or after the homogenization step.

The homogenate is centrifuged, and the pellet containing the inclusion bodies is obtained after decanting the supernatant. The inclusion body pellet is washed in water, or Tris buffers with or without varying levels of the following compounds: sodium chloride, urea, Triton X-100, zinc chloride, sodium lauryl sulfate, sucrose.

In another embodiment, the cells are harvested by transferring the fermentation broth to centrifuge bottles and centrifuging at 2-8° C. for 20-60 minutes. For example, a Beckman J6MI centrifuge with KompSpin KAJ7.100 rotor (Beckman Coulter, Fullerton, Calif.) at 7500×G can be used to harvest cells. A Beckman Avanti JHC centrifuge with a Beckman JLA-8.1 fixed angle rotor (8,000-15,800×G) or an Aries JS 5.0 Swinging Bucket rotor with 2.25 L bottles at 7500×G can be used as well. A continuous centrifuge such as those supplied by Carr Separations, Inc. (Franklin, Mass.) or Westfalia Separator, Inc. (Northvale, N.J.) can also be used.

The culture broth or supernatant is removed from the centrifuge bottles. The cell pellets are resuspended in homogenization buffer (100 mM Tris, 5 mM $ZnCl_2$, pH 7.5) at 10-30% w/v solids. The fermentation broth is passed through the APV-Gaulin homogenizer and the cell suspension is collected. The homogenizer pressure should be set at 6000-14,000 psi for maximum cell disruption. In one embodiment, the pressure is 10,000 psi. The suspension is passed through the homogenizer for 1-5 passes, for example, 3 passes.

Additionally, the methods of recovering FGF18 or trFGF18 can comprise a further step of precipitating, washing, and resolubilizing the FGF18 or trFGF18. The washed inclusion bodies are solubilized in 6 M guanidine or 8 M urea, diluted 6-10 fold in water or buffer, incubated 30 minutes, and centrifuged or filtered. Alternatively, ultrafiltration or macrofiltration can be used wash inclusion bodies after homogenization. The resulting precipitate is washed in 2-6 M urea, and contains the FGF18 or trFGF18 protein. The precipatate is then washed with water prior to solublization. Addition of $Al^{3+}$ or $Fe^{3+}$ or anionic and cationic polymers or agents such as spermine, PEI and benzonase may be added to precipitate cell debris, soluble proteins, DNA, RNA, and carbohydrates.

Solubilization of Inclusion Bodies

The washed inclusion body prep can be solubilized using guanidine hydrochloride (5-8 M), guanidine thiocyanate (5-6 M), or urea (7-8 M) containing a reducing agent such as beta mercaptoethanol (10-100 mM), or dithiothreitol (5-50 mM). The solutions can be prepared in Tris, phopshate, HEPES or other appropriate buffers. Inclusion bodies can also be solubilized with urea (2-4 M) containing sodium lauryl sulfate (0.1-2%). Inclusion bodies from 1 liter of fermentation broth can be solubilized using 50-200 ml of the described solutions. The one method provides solubilizing the inclusion body pellets from 1 liter of fermentation broth in 150 ml of 6 M GuHCl prepared in 100 mM Tris, pH 8.0, containing 40 mM DTT. In another embodiment, an inclusion body slurry is mixed with 50-100 ml 8 M GuHCL. The slurry is re-suspended by mixing with a spatula followed by homogenization with an Omni EZ homogenizer (Omni International, Warrenton, Va.) or mixing with a mechanical device. The suspension is mixed for 30-120 minutes, at 3-37° C. In one embodiment, the suspension is mixed at 15-25° C., to finish the solubilization process. The sample is then centrifuged at 7,500-16,000×G at 4° C. for 10-30 minutes using an appropriate centrifuge. The supernatant sample containing the solubilized FGF18 or trFGF18 is decanted and retained.

The concentration of the FGF18 or trFGF18 in the solubilized fraction is determined by reversed phase HPLC. A Jupiter C5 column (Phenomenex, Torrance, Calif.) is used with acetonitrile/trifluoroacetic acid as the mobile phase. FGF18 or trFGF18 standard is diluted in a guanidine/DTT/Tris-containing buffer and different amounts are injected onto the column. The area under the FGF18 or trFGF18 peak is used to construct a standard curve. The solubilized FGF18 or trFGF18 sample is microfuged to remove particulates prior to injection on the HPLC column. Determination of the area under the FGF18 or trFGF8 peak allows quantification of the FGF18 or trFGF18 concentration from the standard curve.

Additionally, the solubilized FGF18 or trFGF18 may be purified at this stage using tangential flow filtration, reverse phase HPLC of immobilized metal affinity chromatography.

Refolding

In one aspect of the invention, the process for recovering purified FGF18 or trFGF18 from transformed *E. coli* host strains in which the FGF18 or trFGF18 is expressed as refractile inclusion bodies, the cells are disrupted and the inclusion bodies are recovered by centrifugation.

The inclusion bodies are then solubilized and denatured in 50 mM TRIS pH 8 and 6 M guanidine hydrochloride containing a reducing agent. The reduced FGF18 or trFGF18 is then oxidized in a controlled renaturation step. This step involves dilution in a refold buffer comprising 50 mM Tris and 120 mM NaCL. This buffer can also comprise arginine hydrochloride, additional salts, and an oxido-shuffling system, although these components are not necessary for successful refolding of either FGF18 or trFGF18. The oxido-shuffling system is used to initiate disulfide bonding of the FGF18 or trFGF18 molecule, and is based on mixtures of reduced and oxidized molecules such as cysteine and cystine, DTT and cystine, reduced glutathione and oxidized glutathione, and DTT and oxidized glutathione. The ratio of reduced to oxidized glutathione can range from 1:1 to 6:1 with a concentration range of 0.5 and 8 mM. In one embodiment, the optimal concentration is 4 mM reduced glutathione: 2 mM oxidized glutathione. The ratio of cysteine to cystine can range from 2:1 to 1:1 with a concentration range of 4 mM to 1 mM of either reagent. In one embodiment, the optimal concentration is 4 mM cysteine, with 2 mM cystine. Optimal refolding may also be achieved using 4 mM cystine and 2 mM DTT which form 4 mM cysteine and 2 mM cystine. Refolding may also be done by sulfitolysis in the presence of reagents such as sodium sulfite and sodium tetrathionate. This process "caps" free cysteines. Because FGF18 or trFGF18 contains only one disufide bond, this step is not generally necessary for successful refolding of FGF18 or trFGF18. The renatured FGF18 or trFGF18 is captured from the dilute refold buffer using cation exchange chromatography, and is purified using hydrophobic interaction chromatography and high performance cation exchange chromatography.

The solute containing FGF18 or trFGF18 is added rapidly (1-5 minutes), or slowly (0.5-5 hours) to the refolding buffer with mixing. The refolding buffer contains Tris and NaCl but can also comprise arginine (0.5 to 1.25 M), PEG, and other salts. It may also include glycerol, guanidine HCl, urea, EDTA, protease inhibitors and chaperones, alcohol, detergents, glycerol and copper sulfate. The FGF18 or trFGF18 can be added in one addition, in multiple additions, or fed in over time. The FGF18 or trFGF18 is added to the refolding mixture to a final concentration of 0.05 to 1.2 mg/ml. The temperature range is 4-30° C. The pH is 7.3 to 8.5. The vessel containing the refold mixture is left open to the atmosphere or can be sparged with air or nitrogen during renaturation. The refolding is allowed to take place 1 to 26 hours. In particular, in specific embodiements of the invention, the refolding time is 5 to 20 hours, 10 to 20 hours, 15 to 18 hours, or about 18 hours.

Refolding can also be done in the presence of EDTA to decrease methionine oxidation, or on a size exclusion column, or using tangential flow filtration, or electrodialysis.

Clarification and Concentration of Refolded FGF18 or TRFGF18

Refolded FGF18 or trFGF18 is passed through a 1.2 μm filter for clarification and removal of insoluble protein. Because FGF18 and trFGF18 have a high PI, a drop in pH is general not necessary to clarify and concentrate the proteins. The filtered solution is concentrated 10-30 fold using tangential flow filtration on a plate and frame system or with a hollow fiber cartridge. The concentrate is then diluted 3-10 fold with buffer or water to allow unfolded and aggregated proteins to precipitate. The solution is then passed through a filter for clarification and removal of insoluble protein.

Surprisingly, FGF18 or trFG18 can be refolded without the use of arginine, although its presense would not be expected to adversely effect the process.

Capture of FGF18 or TRFGF18

In another aspect of the present invention, after the FGF18 or trFGF18 protein is refolded and concentrated, the methods of the present invention comprise capturing the refolded FGF18 or trFGF18 protein is captured in dilute buffer on a cation exchange column and purifying FGF18 or trFGF18 protein using hydrophobic interaction chromatography and high performance cation exchange chromatography.

The capture step is designed to capture the diluted, folded FGF18 or trFGF18 and carry out initial purification. The clarified, diluted FGF18 or trFGF18 is captured on a cation exchange column at pH 8.0. Typically, SP Sepharose XL (Amersham Biosciences, Piscataway, N.J.) or TOYOPEARL SP 550C (Tosoh Biosep, Montgomery, Pa.) is used. The equilibration buffer is the same as the refolding buffer described above and the bound FGF18 or trFGF18 is eluted with an increasing salt gradient. FGF18 or trFGF18 elutes from the SP Sepharose XL using a NaCl step or NaCl gradient.

Expanded bed chromatography can also be used for FGF18 or trFGF18 capture following refolding. In that case the dilution step is carried out in-line while loading the FGF18 or trFGF18 onto the column. Streamline SP XL (Amersham Biosciences) is equilibrated with refolding buffer. FGF18 or trFGF18 is then loaded in upflow mode onto the equilibrated Streamline SP XL resin, which is maintained at twice the settled bed height, while diluting 1:3 inline with water. Following washing in both upflow and downflow modes, FGF18 or trFGF18 is eluted in downflow mode with a NaCl step or a NaCl gradient.

The methods of the present invention provide the use of many different cation exchange resins for this step, including weak cation exchangers such as carboxymethyl, different types of solid supports such as agarose or cellulose, and different particle sizes. The methods of the present invention can also provide running the columns at different pHs in the range from 5.0 to 9.0, and with different buffers and salts. Alternatively, other chromatographic methods such as hydrophobic interaction, anion exchange, and metal chelate maybe used to capture the refolded FGF18 or trFGF18.

Purification

In one aspect of the present invention, there is an intermediate purification of FGF18 or trFGF18 protein. This step is designed to achieve further purification of the FGF18 or trFGF18 using hydrophobic interaction chromatography. Typically Butyl Sepharose FF (Amersham Biosciences) or TOYOPEARL butyl 650M (Tosoh Biosep) are resins used for this step. The resin is equilibrated with 50 mM Tris, 1M NaCl, 1M $(NH_4)_2SO_4$, pH 8.0. FGF18 or trFGF18 that has been purified by cation exchange chromatography is adjusted to 1.5 M $(NH_4)_2SO_4$ and then passed through a 0.45 μm nominal filter. The adjusted and filtered FGF18 or trFGF18 is then loaded onto the equilibrated resin, which is then washed with equilibration buffer to remove unbound material. FGF18 or trFGF18 is eluted with a linear gradient of PBS (7 mM $Na_2HPO_4$, 1.5 mM $KH_2PO_4$, 137 mM NaCl, 2.7 mM KCl, pH 7.5) and equilbration buffer. FGF18 or trFGF18 elutes from the column at approximately 120 mS/cm.

Other hydrophobic interaction chromatography resins that can be used for this step include, for example, those substituted with phenyl or hexyl, different types of solid supports such as agarose or cellulose, and different particle sizes. The present invention also provides running the columns at different pHs in the range from 5.0 to 9.0, and with different buffers and salts. The present invention also provides running the column in such a manner that FGF18 or trFGF18 does not bind.

The final column eluate pool is concentrated using a 5 kDa molecular weight cut-off tangential flow filtration plate and frame membrane, diafiltered against PBS, pH 7.3, described above. Other membranes can be used, such as a 3 kDa or 8 kDa molecular weight cut-off plate and frame membrane or a 10 kDa molecular weight cut-off hollow fiber system to achieve this ultrafiltration/diafiltration step. The purity of the FGF18 or trFGF18 following these procedures is at least 95%, and typically greater than 98%, by sodium dodecyl sulfate polyacrylamide gel electrophoresis. The endotoxin level in the FGF18 or trFGF18 preparation following cation exchange chromatography capture, hydrophobic interaction chromatography purification, and buffer exchange, is generally <10 endotoxin units per mg FGF18 or trFGF18 protein, and typically <2 endotoxin units per mg FGF18 or trFGF18 protein. The endotoxin level following high performance cation exchange chromatography is generally <1 endotoxin unit per mg FGF18 or trFGF18.

Further purification of FGF18 or trFGF18 to remove the remaining impurities and contaminants may be desirable. For example, an anion exchange column can be used to reduce the endotoxin level. FGF18 or trFGF18 is diluted to a conductivity level of <10 mS/cm and the pH is adjusted to 8.0. It is applied to a Q Sepharose FF column (Amersham Biosciences) which has been equilibrated to 20 mM Tris, pH 8.0. The FGF18 or trFGF18 passes through the column and has an approximately 80% reduction in endotoxin compared to the load. Mustang Q or Mustang E (Pall, Port Washington, N.Y.) membranes can also be used to reduce endotoxin levels between pH 5.0 and 9.0.

Other purification steps that could potentially be used to further purify FGF18 or trFGF18 include metal chelate chromatography, anion exchange chromatography, or hydrophobic interaction chromatography on a phenyl column. It is also possible to carry out purification prior to refolding the FGF18 or trFGF18, using for example reversed phase HPLC, ion exchange chromatography or metal chelate chromatography. Thus, the present invention further provides methods comprising the additional steps of purification disclosed herein.

Characterization of Purified FGF18 or TRFGF18

Assays measuring cell proliferation or differentiation are well known in the art. Specifically, biological activity of FGF18 or trFGF18 can be measured using a BaF3 or CCC4 assay, described in detail below. Additional well know assays include assays measuring proliferation include such assays as chemosensitivity to neutral red dye (Cavanaugh et al., *Investigational New Drugs* 8:347-354, 1990, incorporated herein by reference), incorporation of radiolabeled nucleotides (Cook et al., *Analytical Biochem.* 179:1-7, 1989, incorporated herein by reference), incorporation of 5-bromo-2'-deoxyuridine (BrdU) in the DNA of proliferating cells (Porstmann et al., *J. Immunol. Methods* 82:169-179, 1985, incorporated herein by reference), and use of tetrazolium salts (Mosmann, *J. Immunol. Methods* 65:55-63, 1983; Alley et al., *Cancer Res.* 48:589-601, 1988; Marshall et al., *Growth Reg.* 5:69-84, 1995; and Scudiero et al., *Cancer Res.* 48:4827-4833, 1988; all incorporated herein by reference). Assays measuring differentiation include, for example, measuring cell-surface markers associated with stage-specific expression of a tissue, enzymatic activity, functional activity or morphological changes (Watt, *FASEB*, 5:281-284, 1991; Francis, *Differentiation* 57:63-75, 1994; Raes, *Adv. Anim. Cell Biol. Technol.*

Bioprocesses, 161-171, 1989; all incorporated herein by reference). FGF18 or trFGF18 produced by the methods described herein is capable of stimulating proliferation of BaF3/FGF18R cells.

Purified FGF18 or trFGF18 can be characterized by a number of physical methods. Optimally, amino acid analysis indicates the amino acid composition of all residues is within 10% of the expected values. N-terminal sequencing gives a single sequence beginning with methionine and corresponding to the sequence predicted from the FGF18 or trFGF18 expression vector. Endoproteinase Lys C digestion followed by liquid chromatography-mass spectrometry can be used to generate a peptide map in which all peaks correspond in mass to predicted tryptic peptides in FGF18 or trFGF18, and in which all predicted tryptic peptides from FGF18 or trFGF8 are identified.

The invention is further illustrated by the following non-limiting examples.

EXAMPLES

Example 1

Construction of Expression Vector, pTAP237

Plasmid pTAP237 was generated by inserting a PCR-generated linker into the SmaI site of pTAP186 by homologous recombination. Plasmid pTAP186 was derived from the plasmids pRS316 (a *Saccharomyces cerevisiae* shuttle vector) and pMAL-c2, an *E. coli* expression plasmid derived from pKK223-3 and comprising the tac promoter and the rrnB terminator. Plasmid pTAP186 contains a kanamycin resistance gene in which the Sma I site has been destroyed and has NotI and SfiI sites flanking the yeast ARS-CEN6 and URA3 sequences, facilitating their removal from the plasmid by digestion with NotI. The PCR-generated linker replaced the expression coupler sequence in pTAP186 with the synthetic RBS II sequence. It was prepared from 100 pmoles each of oligonucleotides zc29,740 and zc29,741, as shown in SEQ ID NOS: 19 and 20, respectively, and approximately 5 pmoles each of oligonucleotides zc29,736 and zc29,738, as shown in SEQ ID NOS: 21 and 22, respectively. These oligonucleotides were combined by PCR for ten cycles of 94° C. for 30 seconds, 50° C. for 30 seconds, and 72° C. for 30 seconds, followed by 4° C. soak. The resulting PCR products were concentrated by precipitation with two times the volume of 100% ethanol. Pellet was resuspended in 10 µL water to be used for recombining into the recipient vector pTAP186 digested with SmaI to produce the construct containing the synthetic RBS II sequence. Approximately 1 µg of the PCR-generated linker and 100 ng of pTAP186 digested with SmaI were mixed together and transformed into competent yeast cells (*S. cerevisiae*). The yeast was then plated onto -URA D plates and left at room temperature for about 72 hours. Then the Ura+ transformants from a single plate were resuspended in 1 mL H$_2$O and spun briefly to pellet the yeast cells. The cell pellet was resuspended in 0.5 mL of lysis buffer. DNA was recovered and transformed into *E. coli* MC1061. Clones were screened by colony PCR as disclosed above using 20 pmoles each of oligonucleotides zc29,740 and zc29,741, as shown in SEQ ID NOS: 19 and 20, respectively. Clones displaying the correct size band on an agarose gel were subject to sequence analysis. The correct plasmid was designated pTAP237.

Example 2

Codon Optimization

Test expression of human FGF18 in *E. coli* produced lower than ideal levels, as well as truncated products, specifically truncation of 11 amino acids from the C-terminal end of the protein. To address the low level of expression, examination of the codons used in the FGF18 coding sequence indicated that it contained an excess of the least frequently used codons in *E. coli* with a CAI value equal to 0.248. The CAI is a statistical measure of synonymous codon bias and can be used to predict the level of protein production (Sharp et al., *Nucleic Acids Res.* 15(3):1281-95, 1987). Genes coding for highly expressed proteins tend to have high CAI values (>0.6), while proteins encoded by genes with low CAI values (<0.3) are generally inefficiently expressed. This suggested a reason for the poor production of FGF18 in *E. coli*.

The production of truncated products was a second inefficiency in the process, requiring isolation of the truncated portion from the produced proteins. Once it was determined that the truncated protein had similar, if not identical biological activity to the full-length protein, a construct that deliberately produced the shorter product was constructed. Specifically, the protein was stopped after amino acid 196 (Lys).

This left the codon issue. Thus, an attempt was made to resynthesizing the gene coding for FGF18 and trFGF18 with more appropriate codon usage provides an improved vector for expression of large amounts of FGF18 or trFGF18.

The codon optimized trFGF18 coding sequence was constructed from twelve overlaping oligonucleotides: zc44,349 (SEQ ID NO:7), zc44,350 (SEQ ID NO:8), zc44,351 (SEQ ID NO:9), zc44,352 (SEQ ID NO:10), zc44,355 (SEQ ID NO:11), zc44,356 (SEQ ID NO:12), zc44,357 (SEQ ID NO:13), zc44,358 (SEQ ID NO:14), zc44,359 (SEQ ID NO:15), zc44,360 (SEQ ID NO:16), zc44,361 (SEQ ID NO:17), zc44,362 (SEQ ID NO:18). Primer extension of these overlapping oligonucleotides followed by PCR amplification produced a full length trFGF18 gene with codons optimized for expression in *E. coli*. The final PCR product was inserted into expression vector pTAP237 by yeast homologous recombination. The expression construct was extracted from yeast and transformed into competent *E. coli* DH10B. Clones resistance to kanamycin were identified by colony PCR. A positive clone was verified by sequencing and subsequently transformed into three production host strains BL21, W3110, and zGold1. The expression vector with the optimized trFGF18 sequence was named pSDH174.

Example 3

Construction of pSDH170 and pSDH174

The human FGF18 coding sequence was generated by PCR amplification using a CD3+ cDNA library pool as template and oligonucleotide primers. To optimize the translation process in *E. coli*, a primer was used to add an ATG initiation codon to the 5' end of the mature FGF18 coding sequence. The resulting gene sequence encoded the mature FGF18 with one extra methionine at the N-terminus. The final PCR product was inserted into expression vector pTAP237 (described in Example 1) by yeast homologous recombination (Raymond et al., *Biotechniques*. 26(1):134-8, 140-1, 1999; U.S. Pat. No. 6,027,442, incorporated herein by reference). The expression construct, pSDH170 (SEQ ID NO:1), was extracted from yeast and transformed into a competent *E. coli* DH10B. Kanamycin resistant clones were identified by colony PCR. A positive clone was verified by sequencing and subsequently transformed into either production host strains BL21, W3110, and zGOLD1 (described below).

Example 4

Expression of trFGF18

*E. coli* were inoculated into 100 mL Superbroth II medium (Becton Dickinson, Franklin Lakes, N.J.) containing 0.01% Antifoam 289 (Sigma-Aldrich, St. Louis, Mo.) and 30 µg/ml kanamycin, and cultured overnight at 37° C. A 10 mL inoculum was added to 500 mL of same medium in a 2 L culture flask that was shaken at 275 rpm at 37° C. until the culture attained an $OD_{600}$ of 4. IPTG was then added to a final concentration of 1 mM and shaking was continued for another 2.5 hours. The cells were centrifuged at 4,000×g for 10 min at 4° C. The cell pellets were frozen at −80° C. for use at a later time.

Expression of trFGF18 was performed on a larger scale in a 25 mL culture at 37° C. One mL of culture was collected 2 hours after IPTG induction. *E. coli* cells were resuspended in an equal volume BugBuster® Protein Extraction Reagent (Novagen, Madison, Wis.) at 4° C. and incubated for 20 min. The soluble and insoluble fractions were separated by centrifugation at 16,000×g for 10 min at 4° C.

Recombinant trFGF18 accumulated as insoluble inclusion bodies. The recovery yield of trFGF18 from most of the *E. coli* strains was considered low. About 80 to 90% of trFGF18 in the inclusion bodies was lost within 20 min after cell lysis and incubation at 4° C. Lysing bacteria with 8 M urea did not improve recovery. However, including protease inhibitors, such as 5 mM $ZnCl_2$ and 0.5 mM Benzamidine, in the cell lysis buffer prevented the loss of trFGF18 from strain E104 (W3110 arabinose⁻). This indicated that a bacterial protease capable of cleaving trFGF18 under denaturing conditions was co-purifying with the inclusion bodies. It was observed that trFGF18 was stable in cells lysates from strain UT5600, but not in E104 cell lysates. This suggested that the protease was present in E104 but not UT5600. Comparison of the genotypes of these strains revealed that OmpT, which cleaves between dibasic residues, was present in E104 but not in UT5600. OmpT is heat stable and active even under denaturing conditions (White et al., ibid. 1995). Examination of the amino acid sequence of FGF18 indicated that it contained at least eight potential OmpT cleavage sites. trFGF18 also demonstrated excellent stability in BL21, another OmpT deficient *E. coli* strain. These data suggested that OmpT protease activity was critical for the stability and recovery of FGF18. The use of *E. coli* strain UT5600 as the production host significantly improves the recovery of trFGF18. Overall the yields of trFGF18 were increased from 2 mg/L to 50-100 mg/L with the combination of construct and host strain improvement.

Example 5

Characterization of FGF18

The protein produced by the processes described above can be analyzed for polypeptide integrity and biological activity using methods well known in the art. For example, the protein can be examined using Western analysis.

For Western analysis, protein samples were separated on a 4-20% MES-SDS NuPAGE gel (Invitrogen) under reducing conditions and transferred to nitrocellulose membrane (Invitrogen) at 30 V for 1 hour. The membrane was blocked with 5% non-fat milk in TTBS buffer (20 mM Tris pH 7.4, 160 mM NaCl, 0.1% Tween 20). Polyclonal antibody specific for human FGF18 was added in TTBS Buffer with 5% non-fat milk and incubated for 1 hour. After washing with TTBS, the blot was probed with HRP conjugated goat-anti rabbit IgG (Bio-Rad) for 1 hour. The blot was subsequently washed three times with TTBS before chemiluminescent detection with ECL reagent from Pierce.

The activity of the FGF18 or trFGF18 protein can be examined using the BaF3 assay as described in Ellsworth et al., *Osteoarthritis Cartilage*, 10:308(2002). A second assay is the osteoblast cell line CCC4 assay.

A high throughput in vitro bioassay for FGF18 was developed using an immortalized osteoblast cell line (CCC4) derived from P53 knockout mice. A P53 osteoblast line expressing the serum response element (SRE)-luciferase reporter system was established. The clonal cell line used was derived by transfecting the immortalized P53 osteoblast cell line CCC4 with a SRE-luciferase/puromycin reporter construct KZ125 and selecting for clones with high luciferase inducibility by serum, PDGF, and bFGF. The assay in its current format is sensitive, reproducible, and results can be generated within one day. CCC4/KZ125 is used in all experiments.

| Growth Medium: | alpha-MEM | 500 ml |
|---|---|---|
| | 15% HIA-FBS | 75 ml |
| | 1 mM Na Pyruvate | 5 ml |
| | 2 mM L-Glutamine | 5 ml |
| | 2 ug/ml puromycin | 20 ul of 50 mg/ml stock |

| Plating Medium: | alpha-MEM | 500 ml |
|---|---|---|
| | 1% HIA-FBS | 5 ml |
| | 1 mM Na Pyruvate | 5 ml |
| | 2 mM L-Glutamine | 5 ml |

| Assay Medium: | DMEM | 500 ml |
|---|---|---|
| | 1% BSA | 66.6 ml of 7.5% BSA |
| | 20 mM HEPES | 10 ml |
| | 1 mM Na Pyruvate | 5 ml |
| | 2 mM L-Glutamine | 5 ml |
| | (the BSA was tissue culture grade) | |

Maintenance of Cell CCC4 cells: Cells are passaged twice weekly using split ratios of 1:10 (confluent in 2 days), 1:20 (confluent in 3 days), 1:40 (confluent in 4 days).

Preparation of Assay Plates: Cells are trypsinized, resuspended in growth medium, then centrifuged at 1000 rpm for 5 min. The cell pellet is resuspended in plating medium, counted on a hemacytometer, adjusted to $2\times10^5$ cells/ml, and plated at 100 ul/well in Dynatech Microlite opaque white microtiter plates (Dynatech, #011-010-7418 and Linbro lids, ICN Biomedical, #76-205-05) and allowed to grow overnight at 37° C., 5% $CO_2$.

Assay of SRE-Luciferase Induction:

Test substances, bFGF and serum controls are diluted in assay medium to a concentration that twice (2×) the final desired assay concentration (FAC) and added (100 ul/well) to assay plates for a final assay volume of 200 ul/well. If test samples are in DMSO then samples are diluted such that the FAC of DMSO does not exceed 1% (or 0.25% DMF). Assay medium, without test substances or control compounds, is added to 4 wells/assay plate to determine the basal (uninduced) luciferase expression on each plate. bFGF at 3 ng/ml FAC is added to 4 wells/plate to determine the maximum possible luciferase induction for each plate. On at least one plate in each assay set a full bFGF (0.001-10 ng/ml FAC) dose response curve is run. If test substance stocks are in DMSO (or DMF), then DMSO (or DMF) is added to the basal and bFGF controls at a final assay concentration (FAC) equal to that in the test substances.

Plates are incubated for 4 hours at 37° C., 5% $CO_2$. Assay medium is dumped from plates and 1× lysis buffer (25 μl/well) is added (Promega, #1501). Plates are then incubated for 15 min. at room temperature. (Plates may be frozen at this point for later assay of luciferase activity). Luciferase substrate (Promega, #E1501) is added, 50 ul/well, using the Labsystems Luminoskan luminometer to do the substrate addition. Luciferase signal (RLU) is read for 2 seconds/well following a 1 second delay.

Data Calculation: Average basal (uninduced) signal is subtracted from all readings and results are expressed as a percentage of the maximum induction produced by 3 ng/ml bFGF. The concentration of test substance (in ug/ml for crude extracts or uM for pure compounds) that produces 50% of the maximum possible luciferase induction is calculated (EC50).

Figure 2:
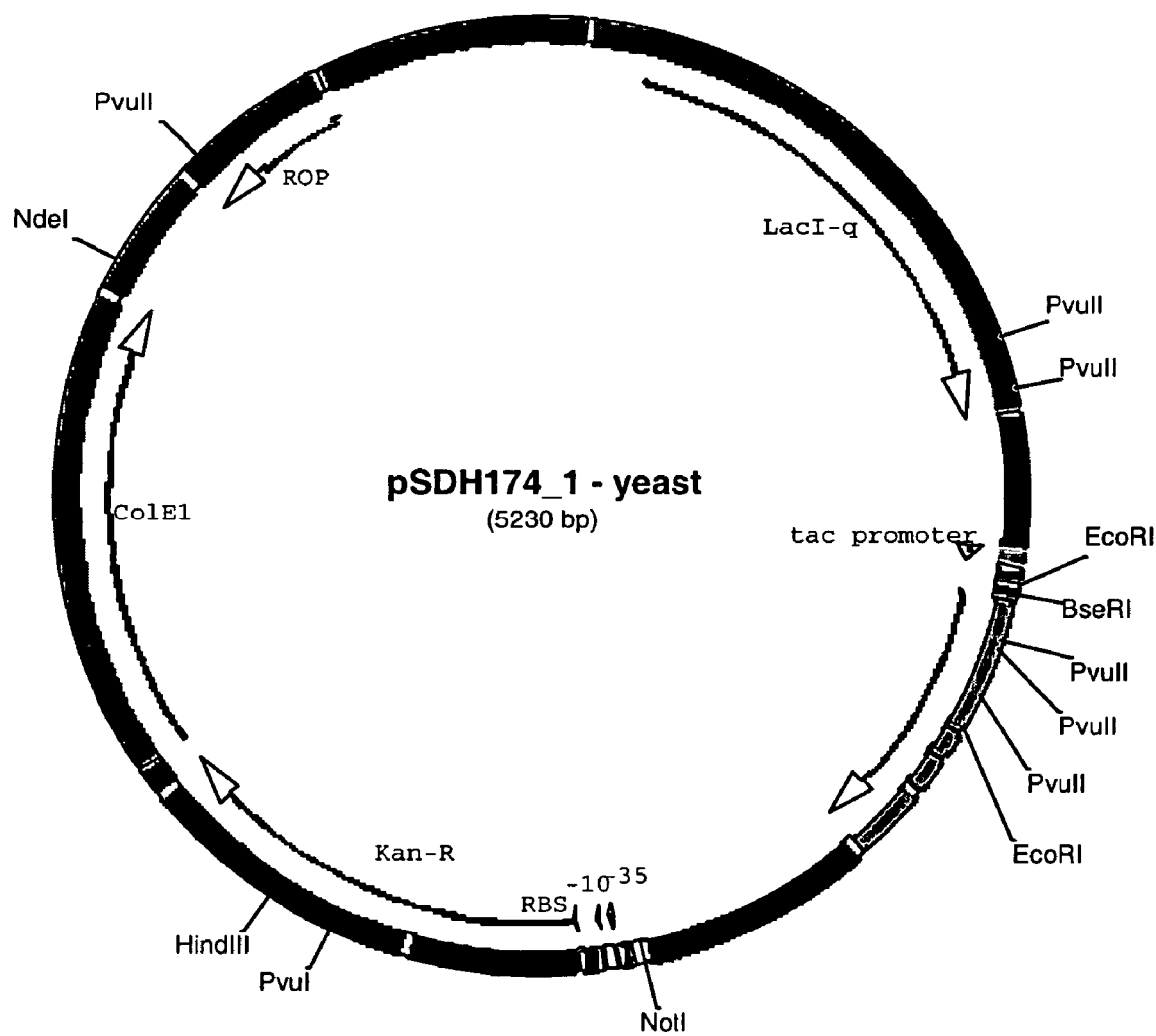
FIG. 2 is illustration of expression plasmid pSDH174, which comprises the codon optimized nucleotide sequence for trFGF18.

Typical standard curves for *E. coli*-derived recombinant human FGF18 spiked into assay medium are shown in FIGS. 1 and 2. The linear range and lower limit of detection of the assay are 0-3 ng/mL and −0.2 ng/mL, respectively.

Example 6

Plasmid Stability Analysis

*E. coli* was inoculated into 25 mL Superbroth II medium (Becton Dickinson) containing 0.01% Antifoam 289 (Sigma) and 30 μg/ml kanamycin, and cultured overnight at 37° C. A 25 μL inoculum was added to 25 mL of same medium without kanamycin in a 25 mL culture flask which was shaken at 275 rpm at 37° C. 100 μL of culture were collected at four different time points (when the culture reached $OD_{600}$ values of 2, 4, 6 and 8). The samples were diluted and plated on LB agar plates without any additives. After overnight incubation at 37° C., 100 *E. coli* colonies were replica plated onto a LB agar plate and a LB agar plate containing 30 μg/ml kanamycin. After overnight incubation at 37° C., the number of colonies that formed on each plate was counted and compared. The number of colonies that grew on LB plus kanamycin relative to the number that grew on the plate without antibiotic reflected the percentage of cells still harboring the expression vector.

When clones of W3110 or zGOLD1 carrying the pSDH170 or pSDH174 expression vector were cultured for 12 hours in medium that did not contain kanamycin, more than 90% retained the plasmid. Clones carrying the expression vector without the FGF18 gene showed similar retention of the plasmid. These data demonstrate that the pSDH170 or pSDH174 expression vector carrying FGF18 or trFGF18 is stable in these production strains.

*E. coli* strains, TG1 and MM294, were not selected as the production host due to low productivity of FGF18 and serious plasmid instability. The most encouraging results came from the studies using *E. coli* strain W3110 (ATCC #27325) to produce FGF18. The productivity of W3110 was comparable to that of UT5600. Plasmid stability studies demonstrated that the expression vector, pTAP337, was maintained in W3110 as well. UT5600 is an auxotrophic strain and more difficult to grow at large scale. These considerations led to selection of W3110 as the preferred host strain for production of FGF18.

Example 7

Batch Fermentation

A first stage seed flask (baffled 500 ml flask with 100 ml medium) was prepared with Difco APS Super Broth (Difco Laboratories, Detroit, Mich.), supplemented with glycerol at 5 g/L and kanamycin at 25 ug/ml. Growth was started by inoculating the shake flask with a loop full of *E. coli* W3110 or zGOLD1 containing the expression vector pSDH170 or pSDH174 from a 24 hour old agar plate (Luria agar (Difco Laboratories) containing kanamycin 25 μg/ml). Growth in the shake flask was at an appropriate temperature (generally, 37° C.). The flask was incubated with agitation set at 250 rpm.

A 2 L fermentation vessel was prepared with 2.0 L of Difco APS Super Broth and sterilized. The growth medium was supplemented with glycerol at 50 g/L and kanamycin at 25 μg/ml plus 5 mL/L 1 M $MgSO_4$. Aeration of the vessel was set to 1 vvm and agitation was set at 350 rpm. The temperature was set to 37° C. The fermentor was inoculated from a first stage seed flask culture grown for 16 hours to an optical density (OD) of 10-20 at 600 nm. The inoculation was 5% v/v. Dissolved oxygen was maintained above 20% saturation by increasing agitation speed or utilizing $O_2$ supplementation if necessary, as is well known in the art.

The culture was grown until the $OD_{600}$ reached 2.5 (approx 2.5 hours). IPTG was added to the culture to a concentration of 1.0 mM. The culture was then allowed to grow for an additional 2.5 hours.

Example 8

A. Fed Batch Fermentation

A first stage seed flask (baffled 500 ml flask with 100 ml medium) was prepared with Difco APS Super Broth, supplemented with glycerol at 5 g/L and kanamycin at 25 ug/ml. Growth was started by inoculating the shake flask with a loop full of *E. coli* W3110 or zGOLD1 (described below) containing the expression vector pSDH170 or pSDH174 (described above) from a 24 hour old agar plate (Luria agar containing kanamycin 25 μg/ml). The shake flask was incubated at 30° C. with agitation set at 250 rpm.

A 6 L fermentation vessel was prepared with 3.0 L of ZymoM growth medium and sterilized. The growth medium was supplemented with glycerol at 20 g/L and kanamycin at 25 μg/ml. The pH of the medium was adjusted to pH 6.4. Aeration was set to 1 vvm, agitation to 350 rpm, and temperature to 32° C. The fermentor was inoculated from a first stage seed flask culture that had been grown for 16 hours to an $OD_{600}$ of 10-20. Inoculation was 5% v/v and dissolved oxygen was maintained above 20% saturation by increasing agitation speed.

A carbohydrate solution was fed into the fermentor starting at 10 hours EFT. The feed was continued until the end of the fermentation. The feed solution was glycerol prepared at 70% v/v. The feed rate was 6 grams of glycerol per liter per hour based on the initial starting volume. At 24 hours EFT, IPTG was added to the culture to a concentration of 2 mM. At 48 hours EFT, the fermentation was harvested.

In an alternative fed batch process, a first stage seed flask (baffled 500 ml flask with 100 ml medium) was prepared with ZSM, supplemented with glucose at 20 g/L and kanamycin at 25 μg/ml. Growth was started by inoculating the shake flask with 300 μl E. coli W3110 frozen in 20% glycerol and containing the expression vector pTAP337. The culture was incubated at 30° C. with agitation at 250 rpm.

A 6 L fermentation vessel was prepared with 3.0 L of ZymoM growth medium and sterilized. The growth medium was supplemented with glucose at 20 g/L and kanamycin at 25 μg/ml. The pH of the medium was adjusted to 6.8. Aeration was set to 1 vvm, agitation to 350 rpm, and temperature to 37° C. The fermentor was inoculated from a first stage seed flask culture that had been grown for 16 hours to an $OD_{600}$ of 16. Inoculation was 5% volume/volume and the dissolved oxygen level was maintained above 20% saturation by increasing agitation speed.

A carbohydrate solution was fed into the fermentor starting at 10 hours EFT. The feed was continued until the end of the fermentation. The feed solution was glucose prepared at 60% v/v and the feed rate was 9.5 grams of glucose per liter per hour based on the initial starting volume. At 24 hours EFT, IPTG was added to the culture to a concentration of 2 mM. At 48 hours EFT, 2 mmol/l of IPTG was added to the culture bringing the IPTG concentration to 4 mM. The fermentation was harvested at 56 hours.

TABLE 1

ZSM medium (shake flask and seed fermentor)

| Ingredient | Amt g/L or ml/L |
| --- | --- |
| Yeast Extract | 5.0 |
| Sodium Sulfate dibasic | 2.0 |
| Ammonium Sulfate dibasic | 2.5 |
| Ammonium Chloride | 0.5 |
| Potassium Phosphate dibasic | 14.6 |
| Potassium Phosphate monobasic | 3.6 |
| Di water | 1.0 L |
| After autoclaving add: | |
| 60% Glucose | 20 g/L (33 mL) |
| Trace D sol. | 3 mL |
| 1M MgSO4 | 3 mL |
| Kanamycin (25 mg/mL stock concentration) | 1.0 mL |

TABLE 2

60% glucose solution for fed batch

| Ingredient | Amt g/L |
| --- | --- |
| H2O | 800 mL |
| Glucose | 1200 g |
| Adjust volume with H2O to: | 2.0 L |
| After autoclaving add: | |
| 1M MgSO4 (30 mL/L) | 60 mL |

TABLE 3

ZymoM - (fed batch fermentation medium)

| Ingredient | Amount g/L or ml/L |
| --- | --- |
| (NH4)2SO4 | 14.0 |
| KH2PO4 | 2.0 |
| K2HPO4 | 16.5 |
| Yeast Extract | 5.5 |
| Glycerol | 20.0 |
| Antifoam AF208 | 0.1 mL |
| Conc. H3PO4 | 1.5 |
| DI water | 1.0 L |
| After autoclaving add: | |
| 1M MgSO4 | 10 mL |
| Trace D Solution* | 17.0 mL |
| Kanamycin (25 mg/mL stock concentration) | 1 mL |

TABLE 4

Trace "D" Solution (for ZymoM and ZSM media)

| Ingredient | Amt. g/L |
| --- | --- |
| FeCl3.6H2O | 6.48 |
| ZnSO4.7H2O | 1.68 |
| MnCl2.4H2O | 1.20 |
| Na2MoO4.2H2O | 0.50 |
| CuSO4.5H2O | 0.24 |
| H3BO3 | 0.72 |
| Conc. H3PO4 | 48.0 mL |
| dH2O | 1.0 L |

B. Fed Batch Fermentation with PCOL22 Medium

A first stage seed flask (baffled 500 ml flask with 100 ml medium) was prepared with ZSM medium, supplemented with glucose at 20 g/L and kanamycin at 25 ug/ml. Growth was started by inoculating the flask with 300 ul of material from a thawed frozen vial of W3110 or zGOLD1 stably tranformed with pSDH170 or pSDH174. The shake flask was incubated at 32 C with agitation set to 250 rpm.

A 2 L fermentation vessel was prepared with 1.2 L of PCOL22 medium (ZSM plus the Trace D solution as described below) and sterilized. After cooling the growth medium was supplemented with, glucose at 20 g/L, magnesium sulfate, calcium chloride, and kanamycin at 25 μg/ml. The pH of the medium was adjusted to 6.8 with 5N ammonium hydroxide. Aeration was set to 1 vvm, agitation was set to 350 rpm, and temperature to 37 C. The fermentor was inoculated from a first stage seed flask culture of EE410 that had been grown for 16 hours to an $OD_{600}$ nm of 10-16. Inoculation was 5% v/v and dissolved oxygen was maintained above 20% saturation by increasing agitation speed plus $O_2$ supplementation. pH was controlled at 6.8 by addition of 5 N $NH_4OH$.

A glucose solution (60% w/v) was fed into the fermentor starting at 8 hours EFT. A constant feed rate of 10 g of glucose/L starting volume per hour was maintained throughout the fermentation. At 24 hours EFT, IPTG was added to the culture to a concentration of 1 mM. The fermentation was harvested at 48 hours EFT.

| Trace "D" Solution (PCOL22 medium) | |
| --- | --- |
| Ingredient | Amt. g/L |
| FeCl3.6H2O | 3.36 |
| ZnSO4.7H2O | 0.84 |
| MnCl2.4H2O | 0.51 |
| Na2MoO4.2H2O | 0.25 |
| CuSO4.5H2O | 0.12 |
| H3BO3 | 0.36 |
| Conc. H3PO4 | 48.0 mL |
| dH2O | 1.0 L |

C. Fed Batch Fermentation with PCOL22 Medium Minus Kanamycin

A first stage seed flask (baffled 500 ml flask with 100 ml medium) was prepared with ZSM medium, supplemented with glucose at 20 g/L and kanamycin at 25 ug/ml. Growth was started by inoculating the flask with 300 ul of material from a thawed frozen vial containing the production strain. The shake flask was incubated at 32 C with agitation set to 250 rpm.

A 6 L fermentation vessel was prepared with 2.7 L of PCOL22 medium and sterilized. After cooling the growth medium was supplemented with, glucose at 20 g/L, magnesium sulfate, and calcium chloride. No kanamycin was added. The pH of the medium was adjusted to 6.8 with 5N ammonium hydroxide. Aeration was set to 1 vvm, agitation was set to 350 rpm, and temperature to 37 C. The fermentor was inoculated from a first stage seed flask culture of EE410 that had been grown for 16 hours to an $OD_{600}$ nm of 16. Inoculation was 5% v/v and dissolved oxygen was maintained above 20% saturation by increasing agitation speed. pH was controlled at 6.8 by addition of 5 N $NH_4OH$.

A glucose solution (60% w/v) was fed into the fermentor starting at 8 hours EFT. A constant feed rate of 9.5 g of glucose/L starting volume per hour was maintained throughout the fermentation. At 24 hours EFT, IPTG was added to the culture to a concentration of 0.5 mM. The fermentation was harvested at 48 hours EFT.

D. Fed Batch Fermentation with PCOL22-L Medium

A first stage seed flask (baffled 500 ml flask with 100 ml medium) was prepared with ZSM medium, supplemented with glucose at 20 g/L and kanamycin at 25 ug/ml. Growth was started by inoculating the flask with 300 ul of material from a thawed frozen vial containing the production strain. The shake flask was incubated at 32 C with agitation set to 250 rpm.

A 6 L fermentation vessel was prepared with 2.7 L of PCOL22-L medium and sterilized. This medium contains citric acid and has one-third less-salts to prevent precipitation. After cooling the growth medium was supplemented with, glucose at 20 g/L, magnesium sulfate, calcium chloride, and kanamycin at 25 ug/ml. The pH of the medium was adjusted to 6.8 with 5N ammonium hydroxide. Aeration was set to 1 vvm, agitation was set to 350 rpm, and temperature to 37 C. The fermentor was inoculated from a first stage seed flask culture of EE410 that had been grown for 16 hours to an $OD_{600}$ nm of 16. Inoculation was 5% v/v and dissolved oxygen was maintained above 20% saturation by increasing agitation speed. pH was controlled at 6.8 by addition of 5 N $NH_4OH$.

A glucose solution (60% w/v) minus magnesium sulfate was fed into the fermentor starting at 8 hours EFT. A constant feed rate of 9.5 g of glucose/L starting volume per hour was maintained throughout the fermentation. At 24 hours EFT, IPTG was added to the culture to a concentration of 0.5 mM. The fermentation was harvested at 48 hours EFT.

E. Fed Batch Fermentation with PCOL12-L Medium

A first stage seed flask (baffled 500 ml flask with 100 ml medium) was prepared with ZSM medium, supplemented with glucose at 20 g/L and kanamycin at 25 ug/ml. Growth was started by inoculating the flask with 300 ul of material from a thawed frozen vial containing the production strain. The shake flask was incubated at 32 C with agitation set to 250 rpm.

A 6 L fermentation vessel was prepared with 2.7 L of PCOL22-L medium and sterilized. This medium contains ¼ th less-salts to prevent precipitation. After cooling the growth medium was supplemented with, glucose at 20 g/L, magnesium sulfate, calcium chloride, and kanamycin at 25 ug/ml. The pH of the medium was adjusted to 6.8 with 5N ammonium hydroxide. Aeration was set to 1 vvm, agitation was set to 350 rpm, and temperature to 37 C. The fermentor was inoculated from a first stage seed flask culture of EE410 that had been grown for 16 hours to an $OD_{600}$ nm of 16. Inoculation was 5% v/v and dissolved oxygen was maintained above 20% saturation by increasing agitation speed. pH was controlled at 6.8 by addition of 5 N $NH_4OH$.

A glucose solution (60% w/v) minus magnesium sulfate was fed into the fermentor starting at 8 hours EFT. A constant feed rate of 9.5 g of glucose/L starting volume per hour was maintained throughout the fermentation. At 24 hours EFT, IPTG was added to the culture to a concentration of 0.5 mM. The fermentation was harvested at 48 hours EFT.

F. Fed Batch Fermentation with PCOL12-R Medium

A first stage seed flask (baffled 500 ml flask with 100 ml medium) was prepared with ZSM medium, supplemented with glucose at 20 g/L and kanamycin at 25 ug/ml. Growth was started by inoculating the flask with 300 ul of material from a thawed frozen vial containing the production strain. The shake flask was incubated at 32 C with agitation set to 250 rpm.

A 6 L fermentation vessel was prepared with 2.7 L of PCOL22-R medium and sterilized. This medium contains increased levels of yeast extract and glucose to increase the growth of the host strain before glucose feeding is initiated. After cooling the growth medium was supplemented with, glucose at 40 g/L, magnesium sulfate, calcium chloride, and kanamycin at 25 ug/ml. The pH of the medium was adjusted to 6.8 with 5N ammonium hydroxide. Aeration was set to 1 vvm, agitation was set to 350 rpm, and temperature to 37 C. The fermentor was inoculated from a first stage seed flask culture of EE410 that had been grown for 16 hours to an $OD_{600}$ nm of 16. Inoculation was 5% v/v and dissolved oxygen was maintained above 20% saturation by increasing agitation speed.

A glucose solution (60% w/v) was fed into the fermentor starting at 8 hours EFT. A constant feed rate of 9.5 g of glucose/L starting volume per hour was maintained throughout the fermentation. At 24 hours EFT, IPTG was added to the culture to a concentration of 0.5 mM. The fermentation was harvested at 48 hours EFT.

G. Fed Batch Fermentation in 20 L vessel

In an alternative fed batch process, a first stage seed vessel (6 l) was prepared with 3.0 L of ZSM medium, supplemented with glucose at 20 g/L and kanamycin at 25 ug/ml. Growth was started by inoculating the vessel with 3.0 ml of material from a thawed frozen vial containing the production strain. Aeration was set to 1 vvm, agitation was set to 350 rpm, and temperature to 32 C.

A 20 L fermentation vessel was prepared with 10.8 L of PCOL22 medium and sterilized. After cooling the growth medium was supplemented with, glucose at 20 g/L, magnesium sulfate, calcium chloride, and kanamycin at 25 ug/ml. The pH of the medium was adjusted to 6.8 with 5N ammonium hydroxide. Aeration was set to 1 vvm, agitation was set to 350 rpm, and temperature to 37 C. The fermentor was inoculated from the first stage seed vessel culture of EE410 that had been grown for 16 hours to an $OD_{600}$ nm of 16. Inoculation was 5% v/v and dissolved oxygen was maintained above 20% saturation by increasing agitation speed. Culture pH was controlled at 6.8 through addition of 5N ammonium hydroxide.

A glucose solution (60% w/v) was fed into the fermentor starting at 8 hours EFT. A constant feed rate of 9.5 g of glucose/L starting volume per hour was maintained throughout the fermentation. At 24 hours EFT, IPTG was added to the culture to a concentration of 0.5 mM. The fermentation was harvested at 48 hours EFT.

H. Fed Batch Fermentation with 2 Stage Seed

A first stage seed flask (baffled 500 ml flask with 100 ml medium) was prepared with ZSM medium, supplemented with glucose at 20 g/L and kanamycin at 25 ug/ml. Growth was started by inoculating the flask with 300 ul of material from a thawed frozen vial containing the production strain. The shake flask was incubated at 32 C with agitation set to 250 rpm.

A second stage seed vessel (6 l) was prepared with 3.0 L of ZSM medium, supplemented with glucose at 20 g/L and kanamycin at 25 ug/ml. Growth was started by inoculating the vessel with 100 ml of material from a first stage seed flask containing the production strain EE410 (*E. coli* W3110 containing the expression vector pTAP337). Aeration was set to 1 vvm, agitation was set to 350 rpm, and temperature to 32 C.

A 20 L fermentation vessel was prepared with 10.8 L of PCOL22 medium and sterilized. After cooling the growth medium was supplemented with, glucose at 20 g/L, magnesium sulfate, calcium chloride, and kanamycin at 25 ug/ml. The pH of the medium was adjusted to 6.8 with 5N ammonium hydroxide. Aeration was set to 1 vvm, agitation was set to 350 rpm, and temperature to 37 C. The fermentor was inoculated from a second stage seed vessel that had been grown for 12 hours to an $OD_{600}$ nm of 16. Inoculation was 5% v/v and dissolved oxygen was maintained above 20% saturation by increasing agitation speed. Culture pH was controlled at 6.8 through addition of 5N ammonium hydroxide.

A glucose solution (60% w/v) was fed into the fermentor starting at 8 hours EFT. A constant feed rate of 9.5 g of glucose/L starting volume per hour was maintained throughout the fermentation. At 24 hours EFT, IPTG was added to the culture to a concentration of 0.5 mM. The fermentation was harvested at 48 hours EFT.

I. Fed Batch Fermentation with zGOLD1

Construction of the expression vector zGOLD1 is described in Example 19. A first stage seed flask (baffled 500 ml flask with 100 ml medium) was prepared with ZSM medium, supplemented with glucose at 20 g/L and kanamycin at 25 ug/ml. Growth was started by inoculating the flask with 300 ul of material from a thawed frozen vial containing the production strain *E. coli* W3110 ompT—(zGOLD1) containing the expression vector pSDH170 or pSHD174. The shake flask was incubated at 32 C with agitation set to 250 rpm.

A 6 L fermentation vessel was prepared with 2.7 L of PCOL22 medium and sterilized. After cooling the growth medium was supplemented with, glucose at 20 g/L, magnesium sulfate, calcium chloride, and kanamycin at 25 ug/ml. The pH of the medium was adjusted to 6.8 with 5N ammonium hydroxide. Aeration was set to 1 vvm, agitation was set to 350 rpm, and temperature to 37 C. The fermentor was inoculated from a first stage seed flask culture of EE410 that had been grown for 16 hours to an $OD_{600}$ nm of 16. Inoculation was 5% v/v and dissolved oxygen was maintained above 20% saturation by increasing agitation speed. Culture pH was controlled at 6.8 through addition of 5N ammonium hydroxide.

A glucose solution (60% w/v) was fed into the fermentor starting at 8 hours EFT. A constant feed rate of 9.5 g of glucose/L starting volume per hour was maintained throughout the fermentation. At 24 hours EFT, IPTG was added to the culture to a concentration of 0.5 mM. The fermentation was harvested at 48 hours EFT.

TABLE 5

| Ingredient | Amt. g/L or ml/L |
| --- | --- |
| $(NH_4)_2SO_4$ | 14.0 |
| $KH_2PO_4$ | 2.0 |
| $K_2HPO_4$ | 16.5 |
| Antifoam AF208 | 0.1 mL |
| DI water | 0.920 L |
| yeast extract (optional) | 5.0 |
| After autoclaving add: | |
| 1M $MgSO_4$ | 10 mL |
| Trace D Solution* | 34.0 mL |
| Kanamycin (25 mg/mL stock concentration) | 1 mL |
| 1 M $CaCl_2$—$2H_2O$ | 2 mL |
| Glucose (60% w/v) | 33.0 ml |

TABLE 6

| Ingredient | Amt. G/L or ml/L |
| --- | --- |
| $(NH_4)_2SO_4$ | 9.25 |
| $KH_2PO_4$ | 1.32 |
| $K_2HPO_4$ | 10.90 |
| Citric Acid | 1.0 g |
| Antifoam AF204 | 0.1 mL |
| DI water | 0.920 L |
| After autoclaving add: | |
| 1M $MgSO_4$ | 10 mL |
| Trace D Solution* | 34.0 mL |
| Kanamycin (25 mg/mL stock concentration) | 1 mL |
| 1 M $CaCl_2$—$2H_2O$ | 2 mL |
| Glucose (60% w/v) | 33.0 ml |

TABLE 7

| Ingredient | Amt g/L |
| --- | --- |
| $H_2O$ | 800 ml |
| Glucose (60% w/v) | 1200 g |

TABLE 7-continued

| Ingredient | Amt g/L |
|---|---|
| Adjust volume with H2O to: Autoclave | 2.0 L |

TABLE 8

| Ingredient | Amt. G/L or ml/L |
|---|---|
| (NH4)2SO4 | 14.0 |
| KH2PO4 | 2.0 |
| K2HPO4 | 16.5 |
| Yeast Extract | 20.0 |
| Antifoam AF204 | 0.1 mL |
| DI water | 0.920 L |
| After autoclaving add: | |
| 1M MgSO4 | 10 mL |
| Trace D Solution* | 34.0 mL |
| Kanamycin (25 mg/mL stock concentration) | 1 mL |
| 1 M CaCl$_2$—2H$_2$O | 2 mL |
| Glucose (60% w/v) | 66.0 ml |

TABLE 9

| Ingredient | Amt. g/L or ml/L |
|---|---|
| (NH4)2SO4 | 10.5 |
| KH2PO4 | 1.50 |
| K2HPO4 | 12.4 |
| Yeast Extract | 5.0 |
| Antifoam AF204 | 0.1 mL |
| DI water | 0.920 L |
| After autoclaving add: | |
| 1M MgSO4 | 10 mL |
| Trace D Solution* | 34.0 mL |
| Kanamycin (25 mg/mL stock concentration) | 1 mL |
| 1 M CaCl$_2$—2H$_2$O | 2 mL |
| Glucose (60% w/v) | 33.0 ml |

Example 9

FGF18 Recovery

A. Disruption of Harvested Cells

The harvested *E. coli* pellet was produced by fed-batch fermentation, and contained approximately 5-6 g/L of FGF18 or trFGF18 in inclusion body form. The fermentation broth (1 L) was pelleted by centrifugation at 8000×g for 30 minutes The pellet was resuspended in 850 ml of breakage buffer (100 mM Tris, pH 7.2, 5 mM ZnCl$_2$) and chilled on ice. The broth was passed through the APV homogenizer three times at 10,000 psi. The broth was then centrifuged at 8000×g for 30 minutes. The supernatant was discarded, taking care to retain the loose pellet. The pellet was washed twice by resuspension in 800 ml of DI water and centrifugation at 8000×g for 40 minutes. The supernatant was discarded, taking care to retain the loose pellet. The inclusion body pellet was stored at −80° C. or refolded without freezing.

B. Direct Disruption of Harvested Broth

The harvested *E. coli* broth was produced by fed-batch fermentation, and contained approximately 6-7 g/L of FGF18 or trFGF18 in inclusion body form. The fermentation broth (0.5 L) was diluted to 1.0 L with deionized water and passed through the APV homogenizer three times at 10,000 psi. The broth was then centrifuged at 15,000×g for 30 minutes. The supernatant was discarded, taking care to retain the loose pellet. The pellet was resuspended in 500 ml of DI water and centrifuged at 15,000×g for 30 minutes. The supernatant was discarded, taking care to retain the loose pellet. The washing step was repeated and the inclusion body pellet was stored at −80° C. or refolded without freezing.

C. Solublization and Precipitation

1. Solubilization was achieved by suspension of the washed inclusion body pellet in 200 mL of 100 mM Tris, 6 M Guanidine hydrochloride, 5 mM ZnCl$_2$, pH 7.2 at room temperature for one hour. The suspension was then centrifuged at 12000 g for 30 minutes. The supernatant was kept at 4° C. The supernatant was diluted 1:8 (v/v) into 100 mM Tris, 5 mM ZnCl$_2$, pH 7.2. The suspension was centrifuged at 12000 g for 10 minutes. The supernatant was discarded. The pellet was resuspended in 200 ml of 100 mM Tris, 8 M Urea, pH 7.2. The suspension was centrifuged at 12000 g for 30 minutes. The supernatant was discarded. The washing procedure was repeated two more times. Resolubilization was achieved by suspension of the washed pellet in 200 mL of 100 mM Tris, 6 M Guanidine hydrochloride, 10 mM DTT, pH 7.2. The suspension was centrifuged at 12000 g for 30 minutes. The protein concentration in the supernatant as measured by HPLC protein assay was 10 mg/mL. The FGF18 sample was then stored at 4° C.

2. The solublization of FGF18 or trFGF18 was achieved by suspending the washed inclusion body body pellet in 6 M Guanidine hydrochloride, 40 mM dithiothreitol (DTT) prepared in 100 Mm Tris, pH 8.0 (GDT40). Approximately 150 ml of GDT40 was used per liter of original fermentation broth. The solublization took place at room temperature for one hour. The suspension was then centrifuged. The supernatant from dissolved inclusion bodies was refolded by dilution (20-30×) into a refolding buffer containing a 0.75 M arginine plus DTT/cystine oxidation-reduction pair. Refolding was allowed to take place for 5-16 hours after which the pH of the mixture was adjusted to pH 5.5 and filtered prior to delivery to purification.

D. Direct Disruption of Harvested Broth from zGOLD1

The harvested *E. coli* zGOLD1 broth was produced by fed-batch fermentation in PCOL22 medium (described above), and contained approximately 9-10 g/L of trFGF18 in inclusion body form. The fermentation broth (0.5 L) was diluted to 1.0 L with dionized water and passed through the APV homogenizer three times at 10,000 psi. The broth was then centrifuged at 15,000×g for 30 minutes. The supernatant was discarded, taking care to retain the loose pellet. The pellet was resuspended in 500 ml of DI water and centrifuged at 15,000×g for 30 minutes. The supernatant was discarded, taking care to retain the loose pellet. The pellet was resuspended in 500 ml of DI water and centrifuged at 15,000×g for 30 minutes. The supernatant was discarded, taking care to retain the loose pellet. The inclusion body pellet was stored at −80° C. or refolded without freezing.

Example 10

A. Solublization of Washed Inclusion bodies

Solubilization was achieved by suspension of the washed inclusion body pellet in 150 mL of 100 mM Tris, 6 M Guanidine hydrochloride, 20 mM dithiothreitol, pH 7.5 at room temperature for one hour. The suspension was then centrifuged at 12000 g for 30 minutes. The protein concentration in the supernatant as measured by HPLC protein assay was 21 mg/mL. The FGF18 sample was then stored at 4° C.

B. Solublization of Washed Inclusion Bodies from zGOLD1

Solubilization was achieved by suspension of a washed inclusion body pellet from 1 liter of fermentation broth in 150 mL of 100 mM Tris, 6 M Guanidine hydrochloride, 40 mM dithiothreitol, pH 8.0 at room temperature for one hour. The suspension was then centrifuged at 15,000×g for 30 minutes. The protein concentration in the supernatant as measured by HPLC protein assay was 29 mg/mL. The IL21 sample was then stored at 4° C.

C. Clarification of Solubilized Inclusion Bodies

Immobilized metal affinity chromatography (IMAC) resin was used to clarify solubilized FGF18 inclusion body pellets. In one example, washed inclusion body pellets were solubilized for 1 hour at room temperature in 6M guanidine HCl containing 10 mM Imidazole, pH 7.5, 1.0 ml His-trap columns (Amersham Biosciences) were charged with 0.5 ml of 0.1M NiSO4. After charging and water washing, 5.0 ml of binding buffer consisting of 6M GuHCl, 20 mM Imidazole, 0.5M NaCl, and 20 mM phosphate was used to equilibrate the column.

The solute sample (1.0 ml) was applied to the column, and the column was washed with 5.0 ml of the binding buffer. FGF18 was eluted by applying 2.5 ml of elution buffer (6M GuHCl, 0.5M Imidazole, 0.5M NaCl, and 20 mM phosphate) to the column. The elution step was repeated, and the samples were analyzed for purity and clarification using SDS-Page gels.

Example 11

Refolding

A. Renaturation

The concentration of FGF18 in the solubilized fraction was determined by reverse phase HPLC to be 21 mg/ml. Determination of the refolding buffer volume was based on the amount of solute and the concentration of FGF18 present in the solute. The refolding buffer (50 mM Tris pH 8 and 120 mM NaCl) was added followed by 0.5M CuSO$_4$ (1:1000 v/v) and stirred for 30 minutes.

Example 12

Capture of Refolded FGF18

A. Cation Exchange Using TOYOPEARL SP 550 C Resin

Following concentration, FGF18 is captured on a cation exchange column. In one example, the concentrated FGF18 is diluted 3-fold with water or 25 mM sodium acetate, pH 5.5. A precipitate is formed which is removed by filtration after 30 minutes incubation at room temperature. A Millipore 1.2 µm Polysep II filter (Millipore) or a 1.2-0.8 µm Cuno Zeta Plus A30MO3 membrane (Cuno, Meriden, Conn.) is used. The filtered FGF18 is loaded onto a column of TOYOPEARL_SP550C resin (Tosoh Biosep) equilibrated to equilibration buffer (25 mM sodium acetate, 0.2 M NaCl, pH 5.5). The column is loaded at a capacity of 6-10 g FGF18 per L resin, the bed height is 15 cm, UV absorbance at 280 nm and 215 nm is monitored, and a flow rate of 150 cm/hr is used. Following loading the column is washed with equilibration buffer until the UV absorbance returns to baseline. The column is then washed with 4 column volumes of 50% equilibration buffer, 50% elution buffer (25 mM sodium acetate, 1.0 M NaCl, pH 5.5). FGF18 is eluted from the column with 25% equilibration buffer, 75% elution buffer. Alternatively, following loading of FGF18 onto the column and washing with equilibration buffer, FGF18 is eluted from the column with a 10 column volume linear gradient from 100% equilibration buffer to 100% elution buffer.

Alternatively, following pH adjustment, dilution, hold step, and filtration using depth filtration, the FGF18 is captured on cation exchange chromatography. The filtered solution is loaded onto a column of TOYOPEARL SP 550 C resin (Tosoh Biosep) and equilibrated to equilibration buffer conditions (25 mM sodium acetate, pH 5.5, 0.4 M NaCl). The column is loaded at a capacity of 6 to 15 g FGF18 per L resin. UV absorbance at 280 nm and 215 nm is monitored, and a flow rate of 150 cm/hr is used. Following loading, the column is washed with equilibration buffer until the UV absorbance returns to baseline. FGF18 is eluted from the column using a step gradient to 100% elution buffer (25 mM sodium acetate, pH 5.5, 0.75 M NaCl).

B. Cation Exchange Chromatography Using SP Sepharose XL Resin

The concentrated FGF18 is diluted 10-fold with 25 mM sodium acetate, pH 5.5. A precipitate is formed which is removed by filtration after 30 minutes incubation at room temperature. A Millipore 1.2 µm Polypro XL filter (Millipore) is followed by a 0.45 µm Whatman Polycap 75 AS filter (Maidstone, Kent, UK). The filtered FGF18 is loaded onto a column of Amersham Biosciences SP Sepharose XL resin equilibrated to equilibration buffer (25 mM sodium acetate, 0.2 M NaCl, pH 5.5). The column is loaded at a capacity of 3-6 g FGF18 per L resin, the bed height is 15 cm, UV absorbance at 280 nm and 215 nm is monitored, and a flow rate of 150 cm/hr is used. Following loading the column is washed with equilibration buffer until the UV absorbance returns to baseline. The column is then washed with 4 column volumes of 25% equilibration buffer, 75% elution buffer (25 mM sodium acetate, 1.0 M NaCl, pH 5.5). FGF18 is eluted from the column with 50% equilibration buffer, 50% elution buffer.

C. Cation Exchange Chromatography Using Streamline SP XL Resin

In another example, FGF18 is not concentrated by tangential flow filtration prior to capture by cation exchange chromatography. Following refolding, the pH is adjusted to 5.5 and the material is filtered through a 1.2 µm nominal cut off filter. An Amersham Biosciences Streamline column packed with Amersham Biosciences Streamline SP XL is equilibrated to equilibration buffer (25 mM sodium acetate, 0.2 M NaCl, pH 5.5). Following equilibration, the filtered, pH-adjusted, refolded FGF18 is loaded onto the column using in-line dilution, i.e. 30% filtered, pH-adjusted, refolded FGF18 and 70% water is loaded using the chromatography system to generate the correct ratio. The FGF18 is loaded onto the column in an upflow direction using a flow rate that causes a 2-fold expansion of the resin compared to the settled bed height. Once the filtered, pH-adjusted refolded FGF18 has been loaded it is replaced with equilibration buffer. Pumping onto the column is then continued with 30% equilibration buffer and 70% water until the conductivity recorded at the column inlet is <10 mS/cm. The column is then washed with equilibration buffer in upflow mode with a 2-fold settled bed height expansion until the UV absorbance at 280 nm returns to baseline. The flow is then stopped and the resin bed allowed to settle. The plunger of the Streamline column is lowered to the settled bed height and the column is washed with equilibration buffer in downflow mode for 2 column volumes at a flow rate of 150 cm/hr. FGF18 is then eluted with 50% elution buffer (25 mM sodium acetate, 1.0 M NaCl, pH 5.5) and 50% equilibration buffer in downflow mode at 150 cm/hr.

Example 13

Intermediate Purification of FGF18 by Hydrophobic Interaction Chromatography

A. Hydrophobic Interaction Chromatography (HIC) using butyl Sepharose resin

FGF18 is adjusted to 1.5 M ammonium sulfate by adding 198 gr solid ammonium sulfate per liter FGF18 solution. The solution is stirred until the ammonium sulfate is dissolved and then solid material is removed by filtration through a 0.45 μm nominal cut-off filter. In one example a 15 cm high column of Amersham Biosciences butyl Sepharose 4 FF is equilibrated to equilibration buffer (25 mM sodium acetate, 50 mM sodium chloride, 1.5 M ammonium sulfate, pH 5.5). The adjusted, filtered FGF18 solution is loaded onto the column at a capacity of 1.0-2.5 g FGF18 per L resin at a flow rate of 150 cm/hr. UV absorbance at 280 nm and 215 nm is monitored. Following loading the column is washed with equilibration buffer until the UV absorbance returns to baseline. FGF18 is eluted from the column with 50% equilibration buffer and 50% elution buffer (25 mM sodium acetate, 50 mM sodium chloride, pH 5.5). Alternatively, following loading of FGF18 onto the column and washing with equilibration buffer, FGF18 is eluted from the column with a 10 column volume linear gradient from 100% equilibration buffer to 100% elution buffer.

B. HIC Using TOYOPEARL 650M Resin In another example a different resin, Tosoh Biosep TOYOPEARL butyl 650M, is used to purify the FGF18. The method is the same as that used for the butyl Sepharose FF resin with the following exceptions: the cation exchange eluate is adjusted to 1.5 M $(NH_4)_2SO_4$ using a 3.5 M $(NH_4)_2SO_4$ stock solution; the adjusted, filtered FGF18 solution is loaded onto the column at a capacity of 10-12 g FGF18 per L resin; following loading, the column is washed with equilibration buffer until UV absorbance returns to baseline; FGF18 is eluted from the column with 100% elution buffer (25 mM sodium acetate, pH 5.5, 0.05 M NaCl, 0.15 M $(NH_4)_2SO_4$).

Example 14

A. Concentration and Buffer Exchange of Purified FGF18 to Phosphate Buffered Saline Following purification FGF18 is subject to ultrafiltration and diafiltration to concentrate it and exchange it to a buffer suitable for storage. A tangential flow filtration apparatus and membranes (Millipore Pellicon Biomax 5 kDa molecular weight cut-off plate and frame system) are sanitized using 0.5 M NaOH and rinsed with water. For purified FGF18 from 1 L of fermentation broth, 0.1 m² or less of membrane area is used with a cross-flow rate of approximately 20-25 L/hr and a transmembrane pressure of 10 psi to 15 psi. FGF18 is concentrated to approximately 15-20 mg/mL and then diafiltered against approximately 5-10 diavolumes of phosphate buffered saline, pH 6.0. The concentrated, buffer exchanged FGF18 is stored at −80° C.

B. Concentration and Buffer Exchange of Purified FGF18 to Histidine/Mannitol Buffer Following purification by SP HP Sepharose, FGF18 is subject to ultrafiltration and diafiltration to concentrate and exchange purified FGF18 into a buffer suitable for storage. A tangential flow filtration apparatus and membranes (Millipore Pellicon Biomax 5 kDa molecular weight cut-off plate and frame system) are sanitized using 0.5 M NaOH and rinsed with water. For purified FGF18, from 1 L of fermentation broth, 0.1 m² or less of membrane area is used with a cross-flow rate of approximately 30 L/hour at a transmembrane pressure of 25. FGF18 is concentrated to approximately 10-15 mg/ml, and then diafiltered against approximately 5-10 diavolumes of 10 mM histidine, 4.72% (w/v) mannitol, pH 5.0-5.3. The resulting solution is sterile filtered.

Example 15

Additional Purification of FGF18

A. Cation Exchange Chromatography Using SP HP Sepharose Resin for Polishing

Further purification using SP HP Sepharose is performed to further improve overall purity. The TOYOPEARL butyl 650M elutate is diluted to 30 mS/cm with water, and then adjusted to pH 6.0 using a dibasic sodium phosphate stock solution. The adjusted solution is then filtered using a 0.22 μm filter. The filtered material is loaded onto the column at 10-15 g FGF18 per L resin on a column equilibrated with 50 mM phosphate, pH 6.0, 0.3 M NaCl. UV 280 nm and UV 215 nm are used to monitor the chromatography. After loading, the column is washed with equilibration buffer until UV reaches baseline. FGF18 is eluted from the column using a 20-column volume gradient to 100% elution buffer (50 mM phosphate, pH 6.0, 0.7 M NaCl).

B. Anion Exchange Chromatography

FGF18 is passed through an anion exchange column to remove endotoxin. A column of Amersham Biosciences Q Sepharose FF is equilibrated with equilibration buffer (20 mM Tris, pH 8.0). The FGF18 solution is adjusted to a conductivity of <10 mS/cm with equilibration buffer. The adjusted FGF18 solution is loaded onto the column at a flow rate of 150 cm/hr. FGF18 does not bind to the column and is collected in the flow-through. In other examples, Amersham Biosciences DEAE Sepharose FF resin or Pall Mustang Q membranes can be used instead of Q Sepharose FF to purify FGF18. In still other examples, pH values in the range from 5.0 to 9.0 have been shown to result in FGF18 passing through anion exchange media.

C. Hydrophobic Interaction Chromatography

In other examples, hydrophobic interaction chromatography, using conditions different than those described above with butyl resin, has been used to purify FGF18. Amersham Biosciences phenyl Sepharose FF high sub, Amersham Biosciences Phenyl Sepharose HP and Amersham Biosciences butyl Sepharose 4 FF can be used as resin in both binding and flow through modes. To bind FGF18, the columns are equilibrated to 25 mM sodium acetate, 50 mM sodium chloride, 1.5 M ammonium sulfate, pH 5.5. FGF18 is adjusted to 1.5 M ammonium sulfate by adding solid ammonium sulfate and stirring until it is dissolved. The adjusted FGF18 solution is loaded onto the equilibrated column at a flow rate of 150 cm/hr. UV absorbance at 280 nm and 215 nm is monitored. Following washing, the FGF18 is eluted from the column with a 10 column volume linear gradient from 100% equilibration buffer to 100% elution buffer (25 mM sodium acetate, 50 mM NaCl, pH 5.5). In flow through mode the FGF18 containing solution is adjusted to 1.0 M or less ammonium sulfate, and loaded onto a column equilibrated with 25 mM sodium acetate, 50 mM NaCl, 1.0 M ammonium sulfate, pH 5.5. The flow through is collected.

In other examples, hydrophobic interaction chromatography using sodium sulfate as salt, rather than ammonium sulfate, has been used to purify FGF18. Amersham Biosciences phenyl Sepharose FF high sub, Amershan Biosciences Phenyl Sepharose HP and Amersham Biosciences butyl Sepharose 4 FF can be used as resin. The columns are equilibrated to 25 mM sodium acetate, 50 mM sodium chloride, 1.5 M sodium sulfate, pH 5.5. FGF18 is adjusted to 1.5 M sodium sulfate by adding solid sodium sulfate and stirring until the sodium sulfate is dissolved. The adjusted FGF18 solution is loaded onto the equilibrated column at a flow rate of 150 cm/hr. UV absorbance at 280 nm and 215 nm is monitored. Following washing, the FGF18 is eluted from the column with a 10 column volume linear gradient from 100% equilibration buffer to 100% elution buffer (25 mM sodium acetate, 50 mM NaCl, pH 5.5).

In another example, HIC FPLC flow-through was performed on a BIOCAD 700E FPLC system (Perseptive Biosystems, Framingham, Mass.) equipped with Butyl Sepharose 4 FF column (Amersham Biosciences). The column was conditioned with 25 mM NaOAc, 600 mM NaCl, 1 M $(NH_4)_2SO_4$. pH 5.5. Solid $(NH_4)_2SO_4$ was added to the cation-exchange eluate to a final concentration of 1 M. The solution was loaded onto the column and FGF18 was collected in the flow-through.

D. IMAC Using Metal Chelating Sepharose

Amersham Biosciences Chelating Sepharose (Amersham) is used to further purify FGF18. Captured FGF18 CIE eluate is loaded onto a column charged with copper, zinc, or nickel ions then equilibrated with 25 mM sodium acetate, pH 5.5; 0.8 M NaCl. UV 280 nm and UV 215 nm are used to monitor the chromatography. The column is then washed with equilibration buffer to baseline, and eluted using a 10 CV gradient to 100% elution buffer (25 mM sodium acetate, pH 5.5; 0.8 M NaCl, 0.5 M imidizole).

Example 16

A. Reversed phase HPLC analysis of solubilized FGF18 in acetonitrile buffer

The method described here is used to quantify FGF18 in solubilized inclusion body samples and purified samples. A 4.6×50 mm Jupiter C5 column (300 Å, 5 μm, Phenomenex) is used on an Agilent Technologies 1100 series HPLC system with thermostated autosampler and thermostatted column compartment. A 0.2 μm pre-column filter is placed before the column. Mobile phase A is 0.1% TFA in HPLC grade water and mobile phase B is 0.1% TFA in acetonitrile.

The elution gradient/time table for purified samples is as follows:

TABLE 10

| Time | % B |
| --- | --- |
| 0 | 5 |
| 3.5 | 5 |
| 4 | 41 |
| 14 | 48 |
| 14.5 | 95 |
| 17 | 95 |
| 17.5 | 5 |
| 20 | 5 |

The elution gradient/time table for solubilized inclusion body samples is:

TABLE 11

| Time | % B |
| --- | --- |
| 0 | 5 |
| 4.0 | 5 |
| 5.5 | 40 |
| 20.0 | 50 |
| 21.0 | 95 |
| 22.0 | 95 |
| 23.0 | 5 |
| 30.0 | 5 |

The column is equilibrated to the initial conditions of the elution gradient/time table until a stable baseline is achieved.

Method parameters are as follows:
1. Flow rate: 1 ml/min.
2. Total run time: 20 minutes
3. Column temperature: 40° C.
4. Autosampler temperature: 8° C.
5. Maximum column pressure: 240 bar
6. Injector draw speed: 100 μL/minute
7. Injector eject speed: 100 μL/minute
8. Diode array detector data collection wavelength: Signal A: 280 nm, 25 nm bandwidth
9. Diode array detector data monitoring wavelength: Signal B: 215 nm, 10 nm bandwidth
10. Diode array detector data reference wavelength: Signal A: 350 nm, 25 nm bandwidth; Signal B: 350 nm, 25 nm bandwidth
11. Diode Array Detector autobalance: Prerun/Postrun mode
12. Peak width response time: >0.1 min.
13. Slit width: 4 nm
14. Needle wash function: programmed to reduce the build-up of guanidine on the needle and needle seat.

For quantitation of unfolded FGF18, FGF18 reference standard is diluted to 0.5 mg/mL with 50 mM Tris, pH 7.5, 6 M guanidine HCl, 10 mM DTT and heated at 40° C. for 20 minutes. Diluted reference standard is injected onto the column at least five levels between 10 μg and 50 μg (for example, 10, 20, 30,40 and 50 μg injections). Solubilized FGF18 samples are spun in a microfuge and diluted 1:10 in 50 mM Tris, pH 7.5, 6 M guanidine HCl prior to injection of 25 μl of sample.

For quantitation of folded FGF18, FGF18 reference standard is diluted to 1.0 mg/ml with phosphate buffered saline, pH 6.0. Folded FGF18 samples are injected to the HPLC without any treatment. Following chromatography the area under the FGF18 peaks is integrated. A standard curve is constructed and the concentration of FGF18 in the samples is read off the standard curve.

B. Methanol-Based RP-HPLC for Quantitation of FGF18

A fifteen-minute methanol-based RP-HPLC method may also be used to evaluate FGF18 preparations ranging from solubilized inclusion bodies through final product.

Method Parameters for FGF18 Methanol-based RP-HPLC Analysis are as follows:

Column: Zorbax 300SB-CN (4.6×50 mm), 3.5 micron
Mobile Phase A: 0.154% TFA, HPLC grade Water
Mobile Phase B: 0.154% TFA, Methanol Elution Gradient/Time Table

TABLE 12

| Time | % B | Flow Rate (mL/minute) |
|---|---|---|
| 0 | 50 | 1.0 |
| 1.0 | 50 | 1.0 |
| 11.0 | 100 | 1.0 |
| 12.0 | 100 | 1.0 |
| 12.5 | 50 | 1.5 |
| 15.0 | 50 | 1.5 |

Total Run-Time: 15 minutes
Column Temperature: 40° C.
Autosampler Temperature: 5° C.
Injector Draw Speed: 90 µL/minute
Injector Eject Speed: 90 µL/minute
DAD Monitoring Wavelength: Signal A: 280 nm, 8 nm bandwidth
Signal B: 215 nm, 8 nm bandwidth
Signal C: 280 nm, 6 nm bandwidth (Reference Wavelength OFF)
DAD Data Collection Wavelength: Signal A: 280 nm, 8 nm bandwidth
DAD Reference Wavelengths: Signals A and B, 360 nm, 16 nm bandwidth
DAD Autobalance: Prerun/Postrun mode
Peak Width Response Time: >0.1 min.
Slit Width: 4 nm
Margin for Negative Absorbance: 100 mAu
Standard Curve Load Amount Range: 1-20 µg
Minimal Injection Volume: 5 µL
Maximum Injection Volume: 100 µL
Pressure Limit: 350 bar
Normal Running Pressure: 130-200 bar

Example 17

OmpT Deficient Strain for Expressing FGF18

A. Construction of a New Host Strain for Production of Heterologous Genes

The current process for production of FGF18 includes expression in the *E. coli* host W3110 [F- mcrA mcrB IN(rrnD-rrnE)1 λ-]. While W3110 is a robust host, it is not ideal for downstream processing. Upon cell lysis, FGF18 is cleaved at amino acid 196 (Lys) (as shown in SEQ ID NO:6) by the OmpT protease present in the outer membrane. This protease is known to cleave other heterologous recombinant proteins, including FGF-18. Proteolysis of FGF18 does not occur in strains lacking OmpT, such as BL21 [F- ompT hsdSB (rB- mB-) gal dcm lon]. While OmpT activity can be minimized during cell lysis with the addition of $ZnSO_4$ or $CuSO_4$, the purification scheme had to be designed to remove truncated FGF18 from the final product. In an effort to streamline the process for production of FGF18 and other heterologous genes, the OmpT protease was removed from W3110 to create a new production strain. The construction of this new *E. coli* host strain is described below.

B. Construction of Plasmid pCHAN1 for Expression of the Red Recombinase Operon

A strategy based on homologous recombination was used to remove the OmpT protease from W3110. In order to delete genes efficiently from the *E. coli* chromosome by homologous recombinantion, certain enzymes with recombinase activity must be present within the cells. To accomplish this, a plasmid was constructed harboring the Red recombinase operon from bacteriophage λ. A fragment containing the Red recombinase genes was synthesized from bacteriophage λ DNA (New England Biolab) by PCR using recombination-specific primers ZC43,586 (SEQ ID NO:23) and ZC43,587 (SEQ ID NO:24) The reaction contained 100 pmol each of primers ZC43,586 and ZC43,587, 10 µl of 10×PCR buffer (Boehringer Mannheim), 1 µl Pwo Polymerase (Boehringer Mannheim), 10 µl of 0.25 mM nucleotide triphosphate mix (Perkin Elmer), and $dH_2O$ in a final volume of 100 µl. The PCR reaction consisted of a single 5 minute cycle at 94° C., followed by 30 cycles of 1 minute at 94° C., 1 minute at 50° C. and 1 minute at 72° C. The last of the 30 cycles was followed by a 5-minute extension at 72° C. and the reaction concluded with an overnight hold at 4° C. The resulting 1964 base pair (bp) fragment contained the Red recombinase operon (SEQ ID NO: 25). The nucleotide sequence as shown in SEQ ID NO:25 encodes for three genes, Gam(γ) as shown from nucleotides 41-454, Bet(β) as shown from nucleotides 463-1245, and Exo as shown from nucleotides 1245-1922.

The Red recombinase operon was incorporated into a plasmid by homologous recombination in yeast. Competent yeast cells (100 µl of *S. cerevisiae* SF838-9Dα) were combined with 100 ng of SmaI-digested pTAP399, an expression vector for the production of IL-21), acceptor vector and 1 µg of the PCR fragment from above. The yeast/DNA mixture was transferred to a 0.2 cm electroporation cuvette and pulsed at 0.75 kV (5 kV/cm), infinite Ω, 25 µF capacitor. The transformation mixture was then added to 1 ml of 1.2 M sorbitol and incubated at 30 C for 1 hour. The cells were plated in 500 µl aliquots onto two URA DS plates (2% dextrose, 2% sorbitol) and incubated at 30° C. for 2 days. After about 48 hours the $Ura^+$ yeast transformants from the plates were suspended in 2 ml $H_2O$ and pelleted by centrifugation. The cell pellet was resuspended in 1 ml of Qiagen P1 lysis buffer (Qiagen) and transferred to a fresh tube containing 1 ml of 0.5 mm zirconia/silica beads (Biospec Products Inc.). The cells were lysed, samples were allowed to settle, 250 µl of lysate were transferred to a fresh tube, and plasmid DNA was isolated using the Qiagen Spin Miniprep kit according to the manufacturer's instructions.

Electrocompetent *E. coli* DH10B cells (Invitrogen) were transformed with 1 µl of the yeast DNA prep. The cells were pulsed in 0.1 cm cuvettes at 2.0 kV, 25 µF and 100Ω. Following electroporation, 250 µl SOC (2% Bacto Tryptone (Difco, Detroit, Mich.), 0.5% yeast extract (Difco), 10 mM NaCl, 2.5 mM KCl, 10 mM $MgCl_2$, 10 mM $MgSO_4$, 20 mM glucose) was added to each sample. Cells were allowed to recover at 37° C. for 2 hours. The entire 250 µl sample was plated in one aliquot on an LB plate (LB broth (Lennox), 1.8% Bacto Agar (Difco)) containing 25 mg/L kanamycin (Sigma). Plates were incubated at 37 C overnight. Individual clones harboring the Red recombinase operon were identified by restriction digest to verify the presence of insert. The inserts of positive clones were subjected to sequence analysis. A plasmid containing the correct insert was designated pCHAN1.

The yeast sequence was then removed from the vector backbone of pCHAN1. 3.0 µl of plasmid DNA were incubated overnight with 24.3 µl $H_2O$, 2.7 µl buffer H (Roche) and 2.0 µl NotI (New England Biolabs) at 37° C. 5 µl of the overnight digest were mixed with 1 µl of 6×DNA sample dye (25% Ficoll Type 400 (Sigma), 0.25% Bromophenol blue (EM Science), 0.25% Xylene Cyanol (Kodak Biomedicals Inc.)), and 4 µl of this solution were run on a 1% agarose gel (EM Science) to verify complete digestion. To recircularize the plasmid, 14 µl of the overnight NotI digest was mixed with 4 µl of 5× ligation buffer (Invitrogen) and 2 µl ligase (Invitrogen). The ligation was incubated overnight at 25° C.

The religated pCHAN1 was transformed into W3110. Electrocompetent W3110 cells (50 µl) were transformed with 1 µl pCHAN1 DNA using the electroportation protocol for *E. coli* described above. After recovery, the entire 250 µl transformation mixture was plated in one aliquot on an LB plate containing 25 mg/L kanamycin. Plates were incubated at 37° C. overnight and ten of the resulting clones were picked for further analysis. They were grown at 37° C. overnight in 2.0 ml Superbroth II (Becton Dickinson) containing 25 µg/ml kanamycin. The following day, 1.0 ml of the overnight digest was used to confirm the presence of pCHAN1. The Qiagen Spin Miniprep Kit was used to make plasmid DNA, following the manufacturer's instructions. The identity of the plasmid was confirmed by restriction digest using EcoRI (Gibco BRL) and NotI (New England Biolabs). Isolate #3 was selected for subsequent experimentation and named EE670.

Generation of a Tetracycline Fragment for Gene Replacement in W3110

The tetracycline gene was chosen as a suitable marker for homologous recombination into the OmpT locus, rendering the OmpT gene inactive. The tetracycline promoter::tetracycline (tet$^P$::tet) fragment was generated by PCR from pBR322 DNA (New England Biolabs) using recombination-specific primers ZG45,112 (SEQ ID NO:26) and ZG45,171 (SEQ ID NO:27). The reaction mixture contained 100 pmol each of primers, ZG45,112 and ZG45,171, 10 µl of 10×PCR buffer (Boehringer Mannheim), 1 µl Pwo Polymerase (Boehringer Mannheim), 10 µl of 0.25 mM nucleotide triphosphate mix (Perkin Elmer), and dH$_2$O in a final volume of 100 µl. The conditions for the PCR reaction were 1 cycle at 2 minutes at 94° C., followed by 30 cycles of 30 seconds at 94° C., 1 minute at 50° C. and 2 minutes at 72° C. This was followed by a 7-minute extension at 72° C. and an overnight hold at 4° C. The resulting 1590 bp fragment carries tet$^P$::tet (SEQ ID NO:28).

The PCR reaction was loaded onto a 1% agarose preparative gel to purify the tet$^P$::tet fragment. The tet$^P$::tet fragment was cut out of the gel and placed in a 0.5 ml eppendorf tube with a small hole in the bottom that was lined with aquarium filter floss (Finny Products, Inc., Cincinnati, Ohio). The tube was inserted into a 1.5 ml eppendorf tube and spun in a tabletop centrifuge at 14,000 rpm for 10 minutes at 25° C. The liquid in the bottom of the 1.5 ml tube was mixed with 10% (vol/vol) 3M NaOAc and 2 volumes of 100% Ethanol. The sample was incubated at −20° C. for 10 minutes and centrifuged for 10 minutes at 4° C. in a tabletop centrifuge to precipitate the PCR fragment. The supernatant was aspirated and the pellet resuspended in 50 µl H$_2$O. The tet$^P$::tet fragment was at a working concentration of 50 ng/µl.

The PCR fragment was ligated into the pCR4.0-BLUNT TOPO® vector (Invitrogen) to use as a positive control for the gene replacement experiments. The ligation was performed according to manufacturer's instructions. *E. coli* DH10B cells (Invitrogen) were transformed with 2 µl of the tet$^P$::tet DNA fragment using the electroporation protocol for *E. coli* described above. Following recovery, the entire 250 µl transformation mixture was plated on an LB plate containing 100 mg/L Ampicillin (Sigma). Plates were incubated at 37° C. overnight.

Ten clones were picked for further analysis. They were grown overnight in 2.0 ml Superbroth II (Becton Dickinson) containing 100 µg/ml ampicillin at 37° C. The following day, 1.0 ml of the overnight culture was used to confirm the presence of plasmid DNA. The Qiagen Spin Miniprep Kit was used to make plasmid DNA, following the manufacturer's instructions. Plasmid DNA was subjected to restriction analysis using SalI (New England Biolabs) and PstI (New England Biolabs) to verify plasmid identity and insert orientation. Isolate #1 was picked for subsequent experimentation. The plasmid was named pSDH185 and the clone, EE686.

Gene Replacement in W3110: Deletion of the OmpT Gene

A 500 ml culture of W3110/pCHAN1 was grown at 37° C. in SOB media [20 g/L tryptone, 5 g/L yeast extract, 0.5 g/L NaCl, 10 ml/L of 250 mM KCl, 5 ml/L of 2 M MgCl$_2$, pH7.0] to an OD$_{600}$ of 0.6. The culture was split into four 125 ml cultures. One culture was left as an uninduced control, while the other three were induced with 1 mM IPTG for 15 minutes, 30 minutes, or 60 minutes. At the end of their respective incubations, competent cells were made from all four cultures in the following manner. Cells were pelleted by centrifugation at 5000 rpm for 10 minutes. The supernatants were drained and each pellet was resuspended in 62.5 ml ice cold H$_2$O. The cultures were pelleted again, the supernatant was drained, and each pellet was resuspended in 31.25 ml cold 10% glycerol. The cultures were then centrifuged at 8000 rpm for 5 minutes. The pellets were drained well and resuspended in residual 10% glycerol.

All four cultures were divided into six 50 µl aliquots which were transformed in the following ways: 1) no DNA negative control, 2) 1 µl (1 µg/µl) pBR322 (New England Biolabs) positive control, 3) 1 µl (1 µg/µl) pTAP279 positive control, 4) 1 µl pSDH185 positive control, 5) 2 µl (50 ng/µl) tetp::tet fragment, and 6) 4 µl (50 ng/µl) tet$^P$::tet fragment. The cells were transformed by electroporation as described above for *E. coli*. Entire transformation mixtures were plated on LB plates containing 10 mg/L tetracycline (Sigma) except for the pTAP279 controls, which were plated on LB plates containing 35 mg/L chloramphenicol (Sigma). Plates were incubated at 37° C. overnight. In addition, 10$^{-6}$ and 10$^{-7}$ dilutions (in H$_2$O) of each four culture were plated on LB plates to evaluate overall efficiency of the recombination process by determining the cell number.

The following day, control plates were taken out of the incubator and assessed. Samples transformed with the tet$^P$::tet fragments were allowed to incubate for an additional 24 hours prior to assay. Twenty-six of the largest clones were identified for further analysis.

Characterization of ompT Deficient Clones

Each of the 26 selected clones was grown overnight at 37° C. in 1 ml of LB with 5 µg/ml tetracycline. The following day, genomic DNA was generated from all 26 clones using the Genomic Prep DNA Isolation Kit (Amersham Pharmacia) according to the manufacturer's instructions.

The genomic DNA from each clone was diluted 1:100 in dH$_2$O to use as a template for PCR analysis. Each diluted sample was assayed using three different sets of PCR primers (three PCR reactions per clone). The reactions contained 100 pmol each of primer set #1: ZG45,357 (SEQ ID NO:29) and ZG45,350 (SEQ ID NO:30), or primer set #2: ZG45,353 (SEQ ID NO:31) and ZG45,355 (SEQ ID NO:32), or primer set #3: ZG45,354 (SEQ ID NO:33) and ZG45,359 (SEQ ID NO:34). The remainder of the 100 µl final volume was made up of 10 µl of 10×PCR buffer (Boehringer Mannheim), 1 µl Pwo Polymerase (Boehringer Mannheim), 10 µl of 0.25 mM nucleotide triphosphate mix (Perkin Elmer) and dH$_2$O. The reaction conditions were: 1 cycle for 5 minutes at 94° C., followed by 30 cycles of 30 seconds at 94° C., 1 minute at 50° C. and 2 minutes at 72° C. The PCR concluded with a 7-minute extension at 72° C. and an overnight hold at 4° C. If the OmpT gene in W3110 was successfully replaced with the tetracycline gene, primer set #1 should amplify a 1584 bp band (SEQ ID NO:35), primer set #2 should amplify an 1190 bp band (SEQ ID NO:42). The results demonstrated that 25 of the 26 clones screened were ompT⁻. W3110 ompT⁻ clones #1 and #3 were selected for subsequent analysis.

To confirm loss of proteolytic activity, Il-21 was incubated with cell lysates from the newly derived ompT⁻ strains and the W3110 parent. Lysate from the ompT⁻ strain, BL21, was included as a positive control. Cells were inoculated into Superbroth II and grown overnight at 37° C. Four 1 ml aliquots of each overnight culture were pelleted at room temperature and the cells were lysed using BugBuster® (Novagen) according to the manufacturer's instructions. Cell lysates were incubated at 25° C. for 4 hours with either: 1) 0.332 mg/ml of IL-21, or 2) 0.332 mg/ml of IL-21 in the presence of 5 mM $ZnCl_2$. Each sample was mixed with an equal volume of NuPAGE 4× Sample Buffer (Invitrogen) containing 2% β-mercaptoethanol (Sigma). The reduced samples were heated for 5 min at 100° C. and 10 μL were loaded onto a 10% NuPAGE polyacrylamide gel (Invitrogen). Electrophoresis was conducted at 130v under denaturing conditions (SDS-PAGE) using 1×MES running buffer (Invitrogen). Gels were stained with Simply Blue Safestain (Invitrogen) following the manufacturer's instructions.

The results indicated that the OmpT protease was inactivated through gene replacement. IL-21 was completely intact after a 4-hour incubation in lysates from BL21, W3110 ompT⁻ #1 and W3110 ompT⁻ #3, but was completely degraded in a lysate from the W3110 parent. The activity of the OmpT protease was inhibited by zinc. In incubations containing 5 mM $ZnCl_2$ the FGF18 remained intact, supporting that OmpT was responsible for the degradation. The newly constructed W3110 ompT⁻ strains were named zGOLD1 (W3110 ompT⁻ #1; and zGOLD3 (W3110 ompT⁻ #3).

Characterization of zGOLD1 and zGOLD3 zGOLD1 and zGOLD3 were grown alongside the W3110 parent for assessment of growth. Cultures of all three strains were grown at 37° C. in LB to an $OD_{600}$ of 1.0. Cell density was measured hourly to assess growth. Dilutions ($10^{-6}$, $10^{-7}$ and $10^{-8}$ in $H_2O$) of each culture were plated on LB kanamycin plates (see above) to determine cell number. The results indicate that the growth of the zGOLD strains is equivalent to that of the W3110 parent strain.

To assess transformation efficiency, cells were harvested and made competent for transformation as described above. Aliquots from each strain were transformed with either: 1) 1 μl pTAP337 (IL-21 expression plasmid;), or 2) no DNA (negative control). Electroporation was carried out as described above. Following recovery, each transformation mixture was plated on an LB plate containing 25 mg/L kanamycin and incubated overnight at 37° C. The data indicate that transformation efficiency of W3110 was not affected by the removal of opmT.

Ten clones of each zGOLD strain transformed with the FGF18 expression vector were selected to evaluate protein production. The clones were grown at 37° C. overnight in Superbroth II (containing 25 μg/ml kanamycin. The overnight cultures were used to inoculate roller drums containing Superbroth II with 25 μg/ml kanamycin. Cells were grown at 37° C. A second culture of one of the clones was grown and served as an uninduced control. When the $OD_{600}$ of each culture was 1.5-2.0, they were induced with 1 mM IPTG (ICN Biomedicals Inc.). Incubation of the cultures continued for another 5 hours. Samples of each culture were analyzed by SDS-PAGE on 4-12% gradient NuPAGE gel (Invitrogen) under reducing conditions as described above. The results indicate that FGF18 production by zGOLD1 and zGOLD3 is equivalent to that of the W3110 parent strain. zGOLD1/pTAP337 is an example of zGOLD1 transformed with an expression vector.

Example 18

It was determined that a further modification of the zGOLD1 strain was desired to increase the amount of heterologous protein by rendering the strain resistant to infection by particular bacteriophage. Using equivalent methods to those described above, the fhuA gene was identified in the zGOLD1 strain and disrupted. This gene was originally identified by Fecker and Braun, J. Bacterio., 156:1301 (1983). fhuA⁻ strains are well known in the art and convey resistence to infection by T-odd phages. Such strains are described, for example, in Boheivers et al. Biochem., 40:2606 (2001). The doubly disrupted strain (ompT⁻, fhuA⁻) was named zGOLD5.

Generation of Chloramphenicol Actyltransferase Gene Fragment

Oligos zc48544 (SEQ ID NO: 37) and zc48545 (SEQ ID NO: 38) were used to amplify the cat gene, coding for chloramphenicol acetyltransferase. zc48544, the sense oligo, consists of two parts. At the 5' end, the oligo is made up of 70 bases that flank the fhuA coding sequence. This sequence ends just 5' to the initial methionine codon. The second half of the oligo consists of 23 bases homologous to the promoter region of the cat gene. zc48545, the antisense oligo, is designed much like the sense oligo. The 5' end of the oligo consists of 73 bases that flank the 3' end of the fhuA coding sequence, including the stop codon. The next 23 bases are homologous to the 3' end of the cat gene.

To amplify the cat gene with the fhuA flanking sequence, the following final concentrations of reagents were used in a total reaction volume of 100 μL: 0.2 pM of each oligo; 0.2 mM dNTPs; 1× reaction buffer; 10% DMSO; and 0.05 U/μL Pwo (Roche). The template used for amplification of the cat gene was pRARE (Novagen). The reaction consisted of 25 cycles of the following: 94° C. for 30 seconds, 55° C. for 30 seconds, and 72° C. for 1 minute. This was done in duplicate. The resulting DNA fragment was analyzed by electrophoresis on a 1% 1×TBE agarose gel. The size of the fragment was approximately 1 kb, as expected. The DNA fragment was cut from the gel and purified from the agarose using a QIAquick Gel Extraction Kit (Qiagen). The concentration of the recovered DNA was determined to be 110 ng/μL by spectrophotometric analysis.

Gene Replacement: Deletion of the fhuA Gene in ZGOLD1

Electrocompetent ZGOLD1 cells containing pCHAN1 were prepared. One hundred microliters of the overnight culture were used to inoculate 50 mL of LB media, containing 25 μg/mL kanamycin, in a shake flask. The cultures were grown at 37° C. with agitation until the $OD_{600}$ was approximately 0.6. At this point the cultures were induced using 1 mM IPTG and were allowed to grow for 15 minutes. The cultures were centrifuged for 10 minutes at 5000×g. The supernatant was discarded, and the pellet was resuspended in a half volume of ice-cold water. The cells were centrifuged again, the supernatant was discarded, and the resulting pellet was resuspended in a quarter volume of ice-cold 10% glycerol. The cells were centrifuged one last time, the supernatant was discarded, and the pellet was resuspended in the residual glycerol.

Two hundred nanograms of the purified PCR product were transformed into the electrocompetent cells in 0.1 cm cuvettes pulsed at 2.0 kV, 25 μF and 400Ω. Following electroporation, the cells were allowed to recover in 0.6 mL of SOC [2% Bacto Tryptone (Difco, Detroit, Mich.), 0.5% yeast extract (Difco), 10 mM NaCl, 2.5 mM KCl, 10 mM $MgCl_2$, 10 mM $MgSO_4$, 20 mM glucose] for one hour at 37° C. The cells were plated as 10 μL and 100 μL aliquots onto LB Cm plates [LB broth (Lennox), 1.8% Bacto Agar (Difco), 10 μg/mL chloramphenicol (Sigma)]. In addition, the remaining cells were plated. The plated cells were incubated at 37° C. overnight.

Thus, this approach was used to inactivate the fhuA gene in ZGOLD1. The cat gene with the fhuA flanking sequence was generated by PCR. After gel purification, 200 ng of the purified PCR product were transformed into electrocompetent ZGOLD1 cells containing pCHAN1. The cells were plated on LB agar containing chloramphenicol at 10 μg/mL. The plated cells were incubated at 37° C. overnight. Six colonies were picked for further analysis. A PCR screen for the presence of the cat gene in the transformed bacteria was performed using oligos zc46,701 (SEQ ID NO: 39) and zc46,702 (SEQ ID NO: 40). These two primers anneal to the genomic DNA flanking the fhuA coding sequence. Therefore, either fhuA or cat would be amplified. If fhuA were present, the resulting PCR product would be about 2.3 kb, but if cat were present, the resulting PCR product would be about 1.1 kb. A ZGOLD1 culture was included as a control. All the screened clones produced a band of approximately 1.1 kb, the size of the cat gene. The results indicate that fhuA is absent from the ZGOLD1 genomic background.

The clones lacking the fhuA gene were challenged with T-odd bacteriophage. W3110 is a phage sensitive strain and was chosen as a negative control. 27C7 (ATCC) is resistant to T-odd bacteriophage and was selected as a positive control. T5 bacteriophage, obtained from ATCC, were resuspended in LB and diluted 1:10, 1:100, 1:1000, and 1:10,000. Five microliters of phage and each phage dilution were spotted on solidified top agar containing bacteria. The plates were allowed to dry and were incubated at 37° C. for 24 hours. The T5 bacteriophage formed plaques on the plates inoculated with W3110. In contrast, no plaques were formed on the plates inoculated with 27C7 and the six fhuA-deleted clones. The results indicate that all six fhuA-deleted clones are resistant to T-odd bacteriophage.

The six fhuA-deleted clones were cultured overnight at 37° C. in the absence of selection. Each clone was streaked onto LB agar containing chloramphenicol at 10 μg/mL. Each clone was re-streaked onto LB agar with and without kanamycin at 25 μg/mL. The E. coli cells were cultured overnight at 37° C. All clones grew on LB agar and no clone grew on LB agar containing kanamycin. The results demonstrate that all of the clones have lost the pCHAN1 plasmid. One isolate was chosen and saved as a glycerol stock. This isolate was designated ZGOLD5.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. An expression vector for producing FGF18 protein comprising the following operably linked elements:
   (a) a prokaryotic origin of replication;
   (b) a transcriptional initiation DNA element;
   (c) a polynucleotide sequence comprising SEQ ID NO:3; and
   (d) a transcriptional terminator.

2. The expression vector of claim 1 which further comprises a selectable marker.

3. The expression vector of claim 2 wherein said selectable marker is selected from the group consisting of tetracycline resistance, ampicillin resistance kanamycin resistance, neomycin resistance, chloramphenicol resistance, and the hok/sok system.

4. The expression vector of claim 1 wherein the polynucleotide sequence encoding the FGF18 protein is operably linked to the Tac promoter, the vector comprises at least one of the Lacl-q gene, the ROP gene, and kanamycin resistence, and the origin of replication of the vector is ColE1.

5. An expression vector consisting of the pSDH170 vector of SEQ ID NO:1.

6. A prokaryotic host cell transformed with the expression vector as in-any one of claims 1-5.

7. The prokaryotic host cell of claim 6 wherein the host cell is an *E. coli* OmpT protease deficient strain.

8. The host cell of claim 6, wherein the host cell is an *E. coli* strain selected from the group consisting of W3110, MM294, TG-1, JM-107, UT5600, and BL21.

9. A method for producing FGF18 proteins comprising:
   (a) culturing a host cell according to claim 6 in growth medium under conditions wherein FGF18 is expressed;
   (b) recovering the host cells from the growth medium; and
   (c) isolating the FGF18 protein from the host cells.

10. A method for producing FGF18 proteins comprising:
    (a) culturing a host cell according to claim 6 in growth medium fed by batch fermentation;
    (b) recovering the host cells from the growth medium; and
    (c) isolating the FGF18 protein from the host cells.

11. A method for producing an FGF18 protein comprising:
    (a) culturing a host cell according to claim 6 in a shake flask to an $OD_{600}$ of 5 to 20 in a growth medium;
    (b) inoculating a fermentation vessel with 1 to 12% v/v of shake flask medium containing host cells;
    (c) culturing the host cells in a growth medium at a pH of 6.2 to 7.2, wherein a feed solution is fed into the fermentation vessel before 15 hours elapsed fermentation time (EFT);
    (d) adding an inducing agent to the fermentation vessel at 20 to 30 hours EFI';
    and (e) harvesting the host cells at 48 to 56 hours EFT.

12. The method of claim 11, wherein the inducing agent is isopropyl β-D thiogalactopyranoside (IPTG) at 0.5 to 2 mM.

13. The method of claim 11, wherein the feed solution comprises a carbohydrate selected from the group consisting of glycerol and glucose at a concentration of growth medium, and a feed rate of 5-15 grams of carbohydrate per hour.

14. The method of claim 13, wherein the glycerol is 40 to 70% v/v glycerol or the glucose is 40 to 70% w/v glucose.

15. The method of claim 13, wherein the glycerol is about 70% v/v or the glucose is about 60% w/v.

16. A method for isolating insoluble FGF18 protein comprising a SEQ ID NO:4 comprising the steps of:
    (a) separating from a fermentation broth a cell pellet or cell slurry comprising water insoluble FGF18 protein material:
    (b) homogenizing the cell pellet or cell slurry to collect inclusion bodies;
    (c) dissolving the insoluble FGF18 protein material in a chaotropic solvent comprising a guanidine salt;
    (d) diluting the chaotropic solvent by addition of a refolding buffer comprising arginine salts and a mixture of reducing and oxidizing components;
    (e) isolating the FGF18 protein by removing unfolded and aggregated proteins by filtering; and
    (f) purifying the FGF18 refolded protein on a cation exchange column; wherein the isolated and purified FGF18 protein is biologically active and at least 90% pure.

17. The method of claim 16 wherein the guanidine salt is selected from the group consisting of guanidine hydrochloride and guanidine thiocyanate.

18. A method for isolating insoluble FGF18 protein comprising SEQ ID NO:4 comprising the steps of:
    (a) separating from a fermentation broth a cell pellet or cell slurry comprising water insoluble FGF18 protein material;
    (b) homogenizing the cell pellet or cell slurry to collect inclusion bodies:
    (c) dissolving the insoluble FGF18 protein material in a chaotropic solvent comprising a guanidine salt; and
    (d) diluting the chaotropic solvent by addition of a refolding buffer comprising arginine salts and a mixture of reducing and oxidizing components;
    (e) isolating the FGF18 protein by removing unfolded and aggregated proteins by filtering;
    (f) purifying the FGF18 refolded protein on a cation exchange column; and
    (g) purifying the FGF18 eluate from step (f) on a hydrophobic interaction column, wherein the isolated and purified FGF18 protein is biologically active.

19. The method of claim 18, wherein the isolated FGF18 protein has an endotoxin level of less than 10 endotoxin units per mg FGF18 protein.

20. An expression vector for producing trFGF18 protein comprising the following operably linked elements:
    (a) a prokaryotic origin of replication;
    (b) a transcriptional initiation DNA element;
    (c) a polynucleotide sequence comprising SEQ ID NO: 5; and
    (d) a transcriptional terminator.

21. The expression vector of claim 20 which further comprises a selectable marker.

22. The expression vector of claim 21 wherein said selectable marker is selected from the group consisting of tetracycline resistance, ampicillin resistance, kanamycin resistance, neomycin resistance, chloramphenicol resistance, and the hok/sok system.

23. The expression vector of claim 20 wherein the polynucleotide sequence encoding the trFGF18 protein is operably linked to the Tac promoter, the vector comprises at least one of the Lacl-q gene, the ROP gene, and kanamycin resistence, and the origin of replication of the vector is ColE1.

24. A pSDH174 expression vector consisting of SEQ ID NO:2.

25. A prokaryotic host cell transformed with the expression vector as in any one of claims 20-24.

26. The prokaryotic host cell of claim 25 wherein the host cell is an *E. coli* OmpT protease deficient strain.

27. The host cell of claim 25 wherein the host cell is an *E. coli* strain selected from the group consisting of W3110, MM294, TG-1, JM-107, UT5600, and BL-21.

28. A method for producing trFGF18 proteins comprising:
 (a) culturing a host cell according to claim 25 in growth medium under conditions wherein trFGF18 is expressed:
 (b) recovering the host cells from the growth medium; and
 (c) isolating the trFGF18 protein from the host cells.

29. A method for producing trFGF18 proteins comprising:
 (a) culturing a host cell according to claim 25 in growth medium by fed batch fermentation;
 (b) recovering the host cells from the growth medium; and
 (c) isolating the trFGF18 protein from the host cells.

30. A method for producing trFGF18 protein comprising:
 (a) culturing a host cell according to claim 25 in a shake flask to an $OD_{600}$ of 5 to 20 in a growth medium;
 (b) inoculating a fermentation vessel with 1 to 12% v/v of shake flask medium containing host cells;
 (c) culturing the host cells in a growth medium at a pH of 6.2 to 7.2, wherein a feed solution is fed into the fermentation vessel before 15 hours elapsed fermentation time (EFT);
 (d) adding an inducing agent to the fermentation vessel at 20 to 30 hours EFT; and
 (e) harvesting the host cells at 48 to 56 hours EFT.

31. The method of claim 30, wherein the inducing agent is isopropyl β-D thiogalactopyranoside (IPTG) at 0.5 to 2 mM.

32. The method of claim 30, wherein the feed solution comprises a carbohydrate selected from the group consisting of glycerol and glucose at a concentration of growth medium, and a feed rate of 5-15 grams of carbohydrate per hour.

33. The method of claim 32, wherein the glycerol is 40 to 70% v/v glycerol or the glucose is 40 to 70% w/v glucose.

34. The method of claim 32, wherein the glycerol is about 70% v/v or the glucose is about 60% w/v.

35. A method of preparing a cell pellet or cell slurry comprising trFGF18 protein comprising:
 (a) seeding a flask with an inoculum comprising an *E. coli* W3110 host cell expressing an trFGF18 polypeptide comprising SEQ ID NO:6, or an *E. coli* W3110 host cell comprising a pSDH174 vector comprising SEQ ID NO:2 wherein trFGF18 polypeptide is expressed, and with growth medium comprising about 5 g/L glycerol;
 (b) culturing the inoculum in growth medium for 16-20 hours at about 30° C.;
 (c) transferring the cultured inoculum in growth medium to a batch fermentor at a concentration of 0.5-5% v/v inoculum;
 (d) fermenting the batch fermentation at about 37° C. and about pH 6.8; with about 2% glycerol;
 (e) introducing a glucose feed at about 8 hours elapsed fermentation time (EFT) of about 9.5 g glucose/liter/hour and continuing until end of a fermentation run;
 (f) adding IPTG at about 24 hour EFT to final concentration of 0.5 m to 2 mM:
 (g) fermenting about 28 hours after addition of IPTG;
 (h) harvesting fermentation broth from the fermenter;
 (i) adding an equal volume of water to the fermentation broth; and
 (j) homogenizing and centrifuging the fermentation broth to collect a cell pellet or cell slurry comprising FGF18 protein material.

36. A method for isolating insoluble trFGF18 protein comprising SEQ ID NO:6 comprising the steps of:
 (a) separating from a fermentation broth a cell pellet or cell slurry comprising water insoluble trFGF18 protein material;
 (b) homogenizing the cell pellet or cell slurry to collect inclusion bodies;
 (c) dissolving the insoluble trFGF18 protein material in a chaotropic solvent comprising a guanidine salt;
 (d) diluting the chaotropic solvent by addition of a refolding buffer comprising arginine salts and a mixture of reducing and oxidizing components;
 (e) isolating the trFGF18 protein by removing unfolded and aggregated proteins by filtering; and
 (f) purifying the trFGF18 refolded protein on a cation exchange column; wherein the isolated and purified trFGF18 protein is biologically active and at least 90% pure.

37. A method for isolating insoluble trFGF18 protein comprising SEQ ID NO:6 comprising the steps:
 (a) separating from a fermentation broth a cell pellet or cell slurry comprising water insoluble trFGF18 protein material;
 (b) homogenizing the cell pellet or cell slurry to collect inclusion bodies;
 (c) dissolving the insoluble trFGF18 protein material in a chaotropic solvent comprising a guanidine salt; and
 (d) diluting the chaotropic solvent by addition of a refolding buffer comprising arginine salts and a mixture of reducing and oxidizing components:
 (e) isolating the trFGF18 protein by removing unfolded and aggregated proteins by filtering;
 (f) purifying the trFGF18 refolded protein on a cation exchange column; and
 (g) purifying the trFGF18 eluate from step (f) on a hydrophobic interaction column, wherein the isolated and purified trFGF18 protein is biologically active.

38. The method of claim 37 wherein the guanidine salt is selected from the group consisting of guanidine hydrochloride and guanidine thiocyanate.

39. The method of claim 37, wherein the isolated trFGF18 protein has an endotoxin level of less than 10 endotoxin units per mg trFGF18 protein.

40. An isolated polynucleotide molecule comprising SEQ ID NO:3.

41. An isolated polynucleotide molecule comprising SEQ ID NO:5.

* * * * *

UNITED STATES PATENT AND TRADEMARK OFFICE
CERTIFICATE OF CORRECTION

PATENT NO. : 7,858,341 B2  
APPLICATION NO. : 11/301383  
DATED : December 28, 2010  
INVENTOR(S) : Brian J. Reardon et al.

Page 1 of 1

It is certified that error appears in the above-identified patent and that said Letters Patent is hereby corrected as shown below:

<u>Title Page</u>
   Item (56) References Cited
   OTHER PUBLICATIONS
   Hu et al. reference, delete "Fibroblash" and insert --Fibroblast-- therefor.
Column 77, line 21; after "ampicillin resistance" insert --,--.
Column 77, lines 22-23; italicize "*hok/sok*".
Column 77, line 27; delete "resistence" and insert --resistance-- therefor.
Column 77, line 32; delete "in-any" and insert --in any-- therefor.
Column 77, line 59; delete "EFI';" and insert --EFT;-- therefor.
Column 78, line 14; delete "a".
Column 78, line 17; delete ":" and insert --;-- therefor.
Column 78, line 28; delete ";" and insert --,-- therefor.
Column 78, line 40; delete ":" and insert --;-- therefor.
Column 78, line 42; delete "and".
Column 79, line 3; italicize "*hok/sok*".
Column 79, lines 7-8; delete "resistence" and insert --resistance-- therefor.
Column 79, line 21; delete ":" and insert --;-- therefor.
Column 79, line 54; delete "an" and insert --a-- therefor.
Column 79, line 60; delete "C.;" and insert --C;-- therefor.
Column 80, line 1; delete "C." and insert --C-- therefor.
Column 80, line 2; delete ";" and insert --,-- therefor.
Column 80, line 6; delete "hour" and insert --hours-- therefor.
Column 80, line 7; delete ":" and insert --;-- therefor.
Column 80, line 9; delete "fermenter" and insert --fermentor-- therefor.
Column 80, line 30; delete ";" and insert --,-- therefor.
Column 80, line 41; delete "and".
Column 80, line 44; delete ":" and insert --;-- therefor.

Signed and Sealed this
Twenty-second Day of February, 2011

David J. Kappos
*Director of the United States Patent and Trademark Office*

SEQUENCE LISTING

<160> NUMBER OF SEQ ID NOS: 40

<210> SEQ ID NO 1
<211> LENGTH: 5262
<212> TYPE: DNA
<213> ORGANISM: Artificial Sequence
<220> FEATURE:
<223> OTHER INFORMATION: Expression vector

<400> SEQUENCE: 1

```
ccgacaccat cgaatggtgc aaaacctttc gcggtatggc atgatagcgc ccggaagaga      60
gtcaattcag ggtggtgaat gtgaaaccag taacgttata cgatgtcgca gagtatgccg     120
gtgtctctta tcagaccgtt tcccgcgtgg tgaaccaggc cagccacgtt tctgcgaaaa     180
cgcgggaaaa agtggaagcg gcgatggcgg agctgaatta cattcccaac cgcgtggcac     240
aacaactggc gggcaaacag tcgttgctga ttggcgttgc cacctccagt ctggccctgc     300
acgcgccgtc gcaaattgtc gcggcgatta aatctcgcgc cgatcaactg ggtgccagcg     360
tggtggtgtc gatggtagaa cgaagcggcg tcgaagcctg taaagcggcg gtgcacaatc     420
ttctcgcgca acgcgtcagt gggctgatca ttaactatcc gctggatgac caggatgcca     480
ttgctgtgga agctgcctgc actaatgttc cggcgttatt tcttgatgtc tctgaccaga     540
cacccatcaa cagtattatt ttctcccatg aagacggtac gcgactgggc gtggagcatc     600
tggtcgcatt gggtcaccag caaatcgcgc tgttagcggg cccattaagt tctgtctcgg     660
cgcgtctgcg tctggctggc tggcataaat atctcactcg caatcaaatt cagccgatag     720
cggaacggga aggcgactgg agtgccatgt ccggttttca acaaaccatg caaatgctga     780
```

```
atgagggcat cgttcccact gcgatgctgg ttgccaacga tcagatggcg ctgggcgcaa    840
tgcgcgccat taccgagtcc gggctgcgcg ttggtgcgga tatctcggta gtgggatacg    900
acgataccga agacagctca tgttatatcc cgccgttaac caccatcaaa caggattttc    960
gcctgctggg gcaaaccagc gtggaccgct tgctgcaact ctctcagggc caggcggtga   1020
agggcaatca gctgttgccc gtctcactgg tgaaaagaaa aaccaccctg cgcccaata    1080 cgcaaaccgc ctctccccgc gcgttggccg attcattaat gcagctggca cgacaggttt   1140
cccgactgga aagcgggcag tgagcgcaac gcaattaatg tgagttagct cactcattag   1200
gcacaattct catgtttgac agcttatcat cgactgcacg gtgcaccaat gcttctggcg   1260
tcaggcagcc atcggaagct gtggtatggc tgtgcaggtc gtaaatcact gcataattcg   1320
tgtcgctcaa ggcgcactcc cgttctggat aatgtttttt gcgccgacat cataacggtt   1380
ctggcaaata ttctgaaatg agctgttgac aattaatcat cggctcgtat aatgtgtgga   1440
attgtgagcg ataacaatt tcacacagaa ttcattaaag aggagaaatt aactatggaa   1500
gaaaacgttg atttccgtat tcacgttgag aaccagactc gcgcacgcga cgacgtatct   1560
cgtaagcagc tgcgtctgta ccagctgtac tcccgtactt ccggtaagca cattcaggtt   1620
ctgggtcgtc gcatctctgc gcgcggcgaa gatggcgaca atacgctca gctgctggtt   1680 gagaccgaca ccttcggctc ccaggtacgc attaaaggca aagagactga attctacctg   1740
tgcatgaacc gcaaaggtaa gctggttggt aagccggatg gtacctccaa gaatgcgtt   1800 ttcatcgaga aagttctgga gaacaactac accgctctga tgtctgcgaa atacagcggc   1860
tggtacgttg gtttcaccaa gaaaggtcgt ccgcgtaaag gtccgaagac ccgtgagaac   1920
cagcaggacg tgcacttcat gaacgttac ccgaaaggcc agccggagct gcagaagccg   1980
ttcaaataca ccaccgtgac caaacgttct cgtcgtattc gtccgactca tccagcataa   2040
tgttttggcg atgagataag attttcagcc tgatacagat taaatcagaa cgcagaagcg   2100
gtctgataaa acagaatttg cctggcggca gtagcgcggt ggtcccacct gaccccatgc   2160
cgaactcaga agtgaaacgc cgtagcgccg atggtagtgt ggggtctccc catgcgagag   2220
tagggaactg ccaggcatca ataaaaacga aaggctcagt cgaaagactg gcctttcgt   2280 tttatctgtt gtttgtcggt gaacgctctc ctgagtagga caaatccgcc gggagcggat   2340
ttgaacgttg cgaagcaacg gcccggaggg tggcgggcag gacgcccgcc ataaactgcc   2400
aggcatcaaa ttaagcagaa ggccatcctg acggatggcc ttttttgcgtt tctacaaact   2460 cttttgcggcc gcaatggccg ccacgttgtg tctcaaaatc tctgatgtta cattgcacaa   2520
gataaaaata tatcatcatg aacaataaaa ctgtctgctt acataaacag taatacaagg   2580
ggtgttatga gccatattca acgggaaacg tcttgctcga ggccgcgatt aaattccaac   2640
atggatgctg atttatatgg gtataaatgg ctcgcgata atgtcgggca atcaggtgcg   2700
acaatctatc gattgtatgg gaagcccgat gcgccagagt tgtttctgaa acatggcaaa   2760
ggtagcgttg ccaatgatgt tacagatgag atggtcagac taaactggct gacggaattt   2820
atgcctcttc cgaccatcaa gcattttatc cgtactcctg atgatgcatg gttactcacc   2880
actgcgatcc cagggaaaac agcattccag gtattagaag aatatcctga ttcaggtgaa   2940
aatattgttg atgcgctggc agtgttcctg cgccggttgc attcgattcc tgtttgtaat   3000
tgtcctttta acagcgatcg cgtatttcgt ctcgctcagg cgcaatcacg aatgaataac   3060
ggtttggttg atgcgagtga ttttgatgac gagcgtaatg gctggcctgt tgaacaagtc   3120
```

```
tggaaagaaa tgcataagct tttgccattc tcaccggatt cagtcgtcac tcatggtgat    3180
ttctcacttg ataaccttat ttttgacgag gggaaattaa taggttgtat tgatgttgga    3240
cgagtcggaa tcgcagaccg ataccaggat cttgccatcc tatggaactg cctcggtgag    3300
ttttctcctt cattacagaa acggcttttt caaaaatatg gtattgataa tcctgatatg    3360
aataaattgc agtttcattt gatgctcgat gagttttttct aatcagaatt ggttaattgg    3420
ttgtaacact ggcagagcat tacgctgata aaggatctaa ggtgaagatc cttttttgata   3480 atctcatgac caaaatccct taacgtgagt tttcgttcca ctgagcgtca gaccccgtag    3540
aaaagatcaa aggatcttct tgagatcctt ttttttctgcg cgtaatctgc tgcttgcaaa    3600
caaaaaaacc accgctacca gcggtggttt gtttgccgga tcaagagcta ccaactcttt    3660
ttccgaaggt aactggcttc agcagagcgc agataccaaa tactgtcctt ctagtgtagc    3720
cgtagttagg ccaccacttc aagaactctg tagcaccgcc tacatacctc gctctgctaa    3780
tcctgttacc agtggctgct gccagtggcg ataagtcgtg tcttaccggg ttggactcaa    3840
gacgatagtt accggataag gcgcagcggt cgggctgaac ggggggttcg tgcacacagc    3900
ccagcttgga gcgaacgacc tacaccgaac tgagatacct acagcgtgag ctatgagaaa    3960
gcgccacgct tcccgaaggg agaaaggcgg acaggtatcc ggtaagcggc agggtcggaa    4020
caggagagcg cacgagggag cttccagggg gaaacgcctg gtatctttat agtcctgtcg    4080
ggtttcgcca cctctgactt gagcgtcgat ttttgtgatg ctcgtcaggg gggcggagcc    4140
tatgaaaaaa cgccagcaac gcggccttttt tacggttcct ggcctttttgc tggcctttttg   4200 ctcacatgtt ctttcctgcg ttatccctg attctgtgga taaccgtatt accgcctttg    4260
agtgagctga taccgctcgc cgcagccgaa cgaccgagcg cagcgagtca gtgagcgagg    4320
aagcggaaga gcgcctgatg cggtatttttc tccttacgca tctgtgcggt atttcacacc    4380
gcatatggtg cactctcagt acaatctgct ctgatgccgc atagttaagc cagtatacac    4440
tccgctatcg ctacgtgact gggtcatggc tgcgccccga cacccgccaa cacccgctga    4500
cgcgccctga cgggcttgtc tgctcccggc atccgcttac agacaagctg tgaccgtctc    4560
cgggagctgc atgtgtcaga ggttttcacc gtcatcaccg aaacgcgcga ggcagctgcg    4620
gtaaagctca tcagcgtggt cgtgcagcga ttcacagatg tctgcctgtt catccgcgtc    4680
cagctcgttg agtttctcca gaagcgttaa tgtctggctt ctgataaagc gggccatgtt    4740
aagggcggtt ttttcctgtt tggtcacttg atgcctccgt gtaagggggga atttctgttc    4800 atgggggtaa tgataccgat gaaacgagag aggatgctca cgatacgggt tactgatgat    4860
gaacatgccc ggttactgga acgttgtgag ggtaaacaac tggcggtatg gatgcggcgg    4920
gaccagagaa aaatcactca gggtcaatgc cagcgcttcg ttaatacaga tgtaggtgtt    4980
ccacagggta gccagcagca tcctgcgatg cagatccgga acataatggt gcagggcgct    5040
gacttccgcg tttccagact ttacgaaaca cggaaaccga agaccattca tgttgttgct    5100
caggtcgcag acgttttgca gcagcagtcg cttcacgttc gctcgcgtat cggtgattca    5160
ttctgctaac cagtaaggca accccgccag cctagccggg tcctcaacga caggagcacg    5220
atcatgcgca cccgtggcca ggacccaacg ctgcccgaaa tt                       5262
```

<210> SEQ ID NO 2
<211> LENGTH: 5230
<212> TYPE: DNA
<213> ORGANISM: Artificial Sequence
<220> FEATURE:
<223> OTHER INFORMATION: Expression vector trFGF18

<400> SEQUENCE: 2

```
ccgacaccat cgaatggtgc aaaacctttc gcggtatggc atgatagcgc ccggaagaga      60
gtcaattcag ggtggtgaat gtgaaaccag taacgttata cgatgtcgca gagtatgccg     120
gtgtctctta tcagaccgtt tcccgcgtgg tgaaccaggc cagccacgtt tctgcgaaaa     180
cgcgggaaaa agtggaagcg gcgatggcgg agctgaatta cattcccaac cgcgtggcac     240
aacaactggc gggcaaacag tcgttgctga ttggcgttgc cacctccagt ctggccctgc     300
acgcgccgtc gcaaattgtc gcggcgatta aatctcgcgc cgatcaactg ggtgccagcg     360
tggtggtgtc gatggtagaa cgaagcggcg tcgaagcctg taaagcggcg gtgcacaatc     420
ttctcgcgca acgcgtcagt gggctgatca ttaactatcc gctggatgac caggatgcca     480
ttgctgtgga agctgcctgc actaatgttc ggcgttatt tcttgatgtc tctgaccaga     540
cacccatcaa cagtattatt ttctcccatg aagacggtac gcgactgggc gtggagcatc     600
tggtcgcatt gggtcaccag caaatcgcgc tgttagcggg cccattaagt tctgtctcgg     660
cgcgtctgcg tctggctggc tggcataaat atctcactcg caatcaaatt cagccgatag     720
cggaacggga aggcgactgg agtgccatgt ccggttttca acaaaccatg caaatgctga     780
atgagggcat cgttcccact gcgatgctgg ttgccaacga tcagatgcg ctgggcgcaa     840
tgcgcgccat taccgagtcc gggctgcgcg ttggtgcgga tatctcggta gtgggatacg     900
acgataccga agacagctca tgttatatcc cgccgttaac caccatcaaa caggattttc     960
gcctgctggg gcaaaccagc gtggaccgct tgctgcaact ctctcagggc caggcggtga    1020
agggcaatca gctgttgccc gtctcactgg tgaaaagaaa aaccaccctg gcgcccaata    1080
cgcaaaccgc ctctcccgc gcgttggccg attcattaat gcagctggca cgacaggttt    1140
cccgactgga agcgggcag tgagcgcaac gcaattaatg tgagttagct cactcattag    1200
gcacaattct catgtttgac agcttatcat cgactgcacg gtgcaccaat gcttctggcg    1260
tcaggcagcc atcggaagct gtggtatggc tgtgcaggtc gtaaatcact gcataattcg    1320
tgtcgctcaa ggcgcactcc cgttctggat aatgtttttt gcgccgacat cataacggtt    1380
ctggcaaata ttctgaaatg agctgttgac aattaatcat cggctcgtat aatgtgtgga    1440
attgtgagcg gataacaatt tcacacagaa ttcattaaag aggagaaatt aactatggaa    1500
gaaaacgttg atttccgtat tcacgttgag aaccagactc gcgcacgcga cgacgtatct    1560
cgtaagcagc tgcgtctgta ccagctgtac tcccgtactt ccggtaagca cattcaggtt    1620
ctgggtcgtc gcatctctgc gcgcggcgaa gatggcgaca aatacgctca gctgctggtt    1680
gagaccgaca ccttcggctc ccaggtacgc attaaaggca aagagactga attctacctg    1740
tgcatgaacc gcaaaggtaa gctggttggt aagccggatg gtacctccaa agaatgcgtt    1800
ttcatcgaga aagttctgga gaacaactac accgctctga tgtctgcgaa atacagcggc    1860
tggtacgttg gtttcaccaa gaaaggtcgt ccgcgtaaag gtccgaagac ccgtgagaac    1920
cagcaggacg tgcacttcat gaaacgttac ccgaaaggcc agccggagct gcagaagccg    1980
ttcaaataca ccaccgtgac caaataatgt tttggcggat gagataagat tttcagcctg    2040
atacagatta aatcagaacg cagaagcggt ctgataaaac agaatttgcc tggcggcagt    2100
agcgcggtgg tcccacctga ccccatgccg aactcagaag tgaaacgccg tagcgccgat    2160
ggtagtgtgg ggtctcccca tgcgagagta gggaactgcc aggcatcaaa taaaacgaaa    2220
ggctcagtcg aaagactggg cctttcgttt tatctgttgt ttgtcggtga acgctctcct    2280
```

```
gagtaggaca aatccgccgg gagcggattt gaacgttgcg aagcaacggc ccggagggtg    2340
gcgggcagga cgcccgccat aaactgccag gcatcaaatt aagcagaagg ccatcctgac    2400
ggatggcctt tttgcgtttc tacaaactct ttgcggccgc aatggccgcc acgttgtgtc    2460
tcaaaatctc tgatgttaca ttgcacaaga taaaaatata tcatcatgaa caataaaact    2520
gtctgcttac ataaacagta atacaagggg tgttatgagc catattcaac gggaaacgtc    2580
ttgctcgagg ccgcgattaa attccaacat ggatgctgat ttatatgggt ataaatgggc    2640
tcgcgataat gtcgggcaat caggtgcgac aatctatcga ttgtatggga agcccgatgc    2700
gccagagttg tttctgaaac atggcaaagg tagcgttgcc aatgatgtta cagatgagat    2760
ggtcagacta aactggctga cggaatttat gcctcttccg accatcaagc attttatccg    2820
tactcctgat gatgcatggt tactcaccac tgcgatccca gggaaaacag cattccaggt    2880
attagaagaa tatcctgatt caggtgaaaa tattgttgat gcgctggcag tgttcctgcg    2940
ccggttgcat tcgattcctg tttgtaattg tccttttaac agcgatcgcg tatttcgtct    3000
cgctcaggcg caatcacgaa tgaataacgg tttggttgat gcgagtgatt ttgatgacga    3060
gcgtaatggc tggcctgttg aacaagtctg gaaagaaatg cataagcttt tgccattctc    3120
accggattca gtcgtcactc atggtgattt ctcacttgat aaccttattt ttgacgaggg    3180
gaaattaata ggttgtattg atgttggacg agtcggaatc gcagaccgat accaggatct    3240
tgccatccta tggaactgcc tcggtgagtt ttctccttca ttacagaaac ggctttttca    3300
aaaatatggt attgataatc ctgatatgaa taaattgcag tttcatttga tgctcgatga    3360 gttttttctaa tcagaattgg ttaattggtt gtaacactgg cagagcatta cgctgataaa    3420
aggatctagg tgaagatcct ttttgataat ctcatgacca aaatccctta acgtgagttt    3480
tcgttccact gagcgtcaga ccccgtagaa aagatcaaag gatcttcttg agatcctttt    3540
tttctgcgcg taatctgctg cttgcaaaca aaaaaaccac cgctaccagc ggtggtttgt    3600
ttgccggatc aagagctacc aactcttttt ccgaaggtaa ctggcttcag cagagcgcag    3660
ataccaaata ctgtccttct agtgtagccg tagttaggcc accacttcaa gaactctgta    3720
gcaccgccta catacctcgc tctgctaatc ctgttaccag tggctgctgc cagtggcgat    3780
aagtcgtgtc ttaccgggtt ggactcaaga cgatagttac cggataaggc gcagcggtcg    3840
ggctgaacgg ggggttcgtg cacacagccc agcttggagc gaacgaccta caccgaactg    3900
agatacctac agcgtgagct atgagaaagc gccacgcttc ccgaaggag aaaggcggac    3960 aggtatccgg taagcggcag ggtcggaaca ggagagcgca cgagggagct tccaggggga    4020
aacgcctggt atctttatag tcctgtcggg tttcgccacc tctgacttga gcgtcgattt    4080
ttgtgatgct cgtcaggggg gcggagccta tggaaaaacg ccagcaacgc ggcctttta    4140 cggttcctgg ccttttgctg gccttttgct cacatgttct ttcctgcgtt atccctgat    4200 tctgtggata accgtattac cgcctttgag tgagctgata ccgctcgccg cagccgaacg    4260
accgagcgca gcgagtcagt gagcgaggaa gcggaagagc gcctgatgcg gtattttctc    4320
cttacgcatc tgtgcggtat ttcacaccgc atatggtgca ctctcagtac aatctgctct    4380
gatgccgcat agttaagcca gtatacactc cgctatcgct acgtgactgg gtcatggctg    4440
cgccccgaca cccgccaaca cccgctgacg cgccctgacg gcttgtctg ctcccggcat    4500 ccgcttacag acaagctgtg accgtctccg ggagctgcat gtgtcagagg ttttcaccgt    4560
catcaccgaa acgcgcgagg cagctgcggt aaagctcatc agcgtggtcg tgcagcgatt    4620
cacagatgtc tgcctgttca tccgcgtcca gctcgttgag tttctccaga agcgttaatg    4680
```

```
tctggcttct gataaagcgg gccatgttaa gggcggtttt ttcctgtttg gtcacttgat    4740
gcctccgtgt aagggggaat tctgttcat gggggtaatg ataccgatga aacgagagag    4800
gatgctcacg atacgggtta ctgatgatga acatgcccgg ttactggaac gttgtgaggg    4860
taaacaactg gcggtatgga tgcggcggga ccagagaaaa atcactcagg gtcaatgcca    4920
gcgcttcgtt aatacagatg taggtgttcc acagggtagc cagcagcatc ctgcgatgca    4980
gatccggaac ataatggtgc agggcgctga cttccgcgtt tccagacttt acgaaacacg    5040
gaaaccgaag accattcatg ttgttgctca ggtcgcagac gttttgcagc agcagtcgct    5100
tcacgttcgc tcgcgtatcg gtgattcatt ctgctaacca gtaaggcaac cccgccagcc    5160
tagccgggtc ctcaacgaca ggagcacgat catgcgcacc cgtggccagg acccaacgct    5220
gcccgaaatt                                                           5230
```

<210> SEQ ID NO 3
<211> LENGTH: 546
<212> TYPE: DNA
<213> ORGANISM: Artificial Sequence
<220> FEATURE:
<223> OTHER INFORMATION: FGF18 optimized codons
<220> FEATURE:
<221> NAME/KEY: CDS
<222> LOCATION: (1)...(546)

<400> SEQUENCE: 3

```
atg gaa gaa aac gtt gat ttc cgt att cac gtt gag aac cag act cgc      48
Met Glu Glu Asn Val Asp Phe Arg Ile His Val Glu Asn Gln Thr Arg
 1               5                  10                  15 gca cgc gac gac gta tct cgt aag cag ctg cgt ctg tac cag ctg tac      96
Ala Arg Asp Asp Val Ser Arg Lys Gln Leu Arg Leu Tyr Gln Leu Tyr
            20                  25                  30 tcc cgt act tcc ggt aag cac att cag gtt ctg ggt cgt cgc atc tct     144
Ser Arg Thr Ser Gly Lys His Ile Gln Val Leu Gly Arg Arg Ile Ser
        35                  40                  45 gcg cgc ggc gaa gat ggc gac aaa tac gct cag ctg ctg gtt gag acc     192
Ala Arg Gly Glu Asp Gly Asp Lys Tyr Ala Gln Leu Leu Val Glu Thr
    50                  55                  60 gac acc ttc ggc tcc cag gta cgc att aaa ggc aaa gag act gaa ttc     240
Asp Thr Phe Gly Ser Gln Val Arg Ile Lys Gly Lys Glu Thr Glu Phe
65                  70                  75                  80 tac ctg tgc atg aac cgc aaa ggt aag ctg gtt ggt aag ccg gat ggt     288
Tyr Leu Cys Met Asn Arg Lys Gly Lys Leu Val Gly Lys Pro Asp Gly
                85                  90                  95 acc tcc aaa gaa tgc gtt ttc atc gag aaa gtt ctg gag aac aac tac     336
Thr Ser Lys Glu Cys Val Phe Ile Glu Lys Val Leu Glu Asn Asn Tyr
            100                 105                 110 acc gct ctg atg tct gcg aaa tac agc ggc tgg tac gtt ggt ttc acc     384
Thr Ala Leu Met Ser Ala Lys Tyr Ser Gly Trp Tyr Val Gly Phe Thr
        115                 120                 125 aag aaa ggt cgt ccg cgt aaa ggt ccg aag acc cgt gag aac cag cag     432
Lys Lys Gly Arg Pro Arg Lys Gly Pro Lys Thr Arg Glu Asn Gln Gln
    130                 135                 140 gac gtg cac ttc atg aaa cgt tac ccg aaa ggc cag ccg gag ctg cag     480
Asp Val His Phe Met Lys Arg Tyr Pro Lys Gly Gln Pro Glu Leu Gln
145                 150                 155                 160 aag ccg ttc aaa tac acc acc gtg acc aaa cgt tct cgt cgt att cgt     528
Lys Pro Phe Lys Tyr Thr Thr Val Thr Lys Arg Ser Arg Arg Ile Arg
                165                 170                 175 ccg act cat cca gca taa                                             546
Pro Thr His Pro Ala
```

-continued

```
Pro Thr His Pro Ala  *
            180

<210> SEQ ID NO 4
<211> LENGTH: 181
<212> TYPE: PRT
<213> ORGANISM: Artificial Sequence
<220> FEATURE:
<223> OTHER INFORMATION: FGF18 protein

<400> SEQUENCE: 4

Met Glu Glu Asn Val Asp Phe Arg Ile His Val Glu Asn Gln Thr Arg
1               5                   10                  15

Ala Arg Asp Asp Val Ser Arg Lys Gln Leu Arg Leu Tyr Gln Leu Tyr
            20                  25                  30

Ser Arg Thr Ser Gly Lys His Ile Gln Val Leu Gly Arg Arg Ile Ser
        35                  40                  45

Ala Arg Gly Glu Asp Gly Asp Lys Tyr Ala Gln Leu Leu Val Glu Thr
    50                  55                  60

Asp Thr Phe Gly Ser Gln Val Arg Ile Lys Gly Lys Glu Thr Glu Phe
65                  70                  75                  80

Tyr Leu Cys Met Asn Arg Lys Gly Lys Leu Val Gly Lys Pro Asp Gly
                85                  90                  95

Thr Ser Lys Glu Cys Val Phe Ile Glu Lys Val Leu Glu Asn Asn Tyr
            100                 105                 110

Thr Ala Leu Met Ser Ala Lys Tyr Ser Gly Trp Tyr Val Gly Phe Thr
        115                 120                 125

Lys Lys Gly Arg Pro Arg Lys Gly Pro Lys Thr Arg Glu Asn Gln Gln
    130                 135                 140

Asp Val His Phe Met Lys Arg Tyr Pro Lys Gly Gln Pro Glu Leu Gln
145                 150                 155                 160

Lys Pro Phe Lys Tyr Thr Thr Val Thr Lys Arg Ser Arg Arg Ile Arg
                165                 170                 175

Pro Thr His Pro Ala
            180

<210> SEQ ID NO 5
<211> LENGTH: 513
<212> TYPE: DNA
<213> ORGANISM: Artificial Sequence
<220> FEATURE:
<223> OTHER INFORMATION: trFGF18 optimized codons
<220> FEATURE:
<221> NAME/KEY: CDS
<222> LOCATION: (1)...(513)

<400> SEQUENCE: 5 atg gaa gaa aac gtt gat ttc cgt att cac gtt gag aac cag act cgc      48
Met Glu Glu Asn Val Asp Phe Arg Ile His Val Glu Asn Gln Thr Arg
1               5                   10                  15 gca cgc gac gac gta tct cgt aag cag ctg cgt ctg tac cag ctg tac      96
Ala Arg Asp Asp Val Ser Arg Lys Gln Leu Arg Leu Tyr Gln Leu Tyr
            20                  25                  30 tcc cgt act tcc ggt aag cac att cag gtt ctg ggt cgt cgc atc tct     144
Ser Arg Thr Ser Gly Lys His Ile Gln Val Leu Gly Arg Arg Ile Ser
        35                  40                  45 gcg cgc ggc gaa gat ggc gac aaa tac gct cag ctg ctg gtt gag acc     192
Ala Arg Gly Glu Asp Gly Asp Lys Tyr Ala Gln Leu Leu Val Glu Thr
    50                  55                  60 gac acc ttc ggc tcc cag gta cgc att aaa ggc aaa gag act gaa ttc     240
```

```
                Asp Thr Phe Gly Ser Gln Val Arg Ile Lys Gly Lys Glu Thr Glu Phe
                65                  70                  75                  80 tac ctg tgc atg aac cgc aaa ggt aag ctg gtt ggt aag ccg gat ggt         288
Tyr Leu Cys Met Asn Arg Lys Gly Lys Leu Val Gly Lys Pro Asp Gly
                    85                  90                  95 acc tcc aaa gaa tgc gtt ttc atc gag aaa gtt ctg gag aac aac tac         336
Thr Ser Lys Glu Cys Val Phe Ile Glu Lys Val Leu Glu Asn Asn Tyr
                100                 105                 110 acc gct ctg atg tct gcg aaa tac agc ggc tgg tac gtt ggt ttc acc         384
Thr Ala Leu Met Ser Ala Lys Tyr Ser Gly Trp Tyr Val Gly Phe Thr
            115                 120                 125 aag aaa ggt cgt ccg cgt aaa ggt ccg aag acc cgt gag aac cag cag         432
Lys Lys Gly Arg Pro Arg Lys Gly Pro Lys Thr Arg Glu Asn Gln Gln
        130                 135                 140 gac gtg cac ttc atg aaa cgt tac ccg aaa ggc cag ccg gag ctg cag         480
Asp Val His Phe Met Lys Arg Tyr Pro Lys Gly Gln Pro Glu Leu Gln
145                 150                 155                 160 aag ccg ttc aaa tac acc acc gtg acc aaa taa                             513
Lys Pro Phe Lys Tyr Thr Thr Val Thr Lys *
                165                 170

<210> SEQ ID NO 6
<211> LENGTH: 170
<212> TYPE: PRT
<213> ORGANISM: Artificial Sequence
<220> FEATURE:
<223> OTHER INFORMATION: trFGF18 protein

<400> SEQUENCE: 6

Met Glu Glu Asn Val Asp Phe Arg Ile His Val Glu Asn Gln Thr Arg
1               5                   10                  15

Ala Arg Asp Asp Val Ser Arg Lys Gln Leu Arg Leu Tyr Gln Leu Tyr
                20                  25                  30

Ser Arg Thr Ser Gly Lys His Ile Gln Val Leu Gly Arg Arg Ile Ser
            35                  40                  45

Ala Arg Gly Glu Asp Gly Asp Lys Tyr Ala Gln Leu Leu Val Glu Thr
        50                  55                  60

Asp Thr Phe Gly Ser Gln Val Arg Ile Lys Gly Lys Glu Thr Glu Phe
65                  70                  75                  80

Tyr Leu Cys Met Asn Arg Lys Gly Lys Leu Val Gly Lys Pro Asp Gly
                85                  90                  95

Thr Ser Lys Glu Cys Val Phe Ile Glu Lys Val Leu Glu Asn Asn Tyr
            100                 105                 110

Thr Ala Leu Met Ser Ala Lys Tyr Ser Gly Trp Tyr Val Gly Phe Thr
        115                 120                 125

Lys Lys Gly Arg Pro Arg Lys Gly Pro Lys Thr Arg Glu Asn Gln Gln
    130                 135                 140

Asp Val His Phe Met Lys Arg Tyr Pro Lys Gly Gln Pro Glu Leu Gln
145                 150                 155                 160

Lys Pro Phe Lys Tyr Thr Thr Val Thr Lys
                165                 170

<210> SEQ ID NO 7
<211> LENGTH: 69
<212> TYPE: DNA
<213> ORGANISM: Artificial Sequence
<220> FEATURE:
<223> OTHER INFORMATION: Construct Oligonucleotide

<400> SEQUENCE: 7
```

```
aaccagcagc tgagcgtatt tgtcgccatc ttcgccgcgc gcagagatgc gacgacccag    60
aacctgaat                                                            69

<210> SEQ ID NO 8
<211> LENGTH: 67
<212> TYPE: DNA
<213> ORGANISM: Artificial Sequence
<220> FEATURE:
<223> OTHER INFORMATION: Construct Oligonucleotide

<400> SEQUENCE: 8
taagcagctg cgtctgtacc agctgtactc ccgtacttcc ggtaagcaca ttcaggttct    60
gggtcgt                                                              67

<210> SEQ ID NO 9
<211> LENGTH: 60
<212> TYPE: DNA
<213> ORGANISM: Artificial Sequence
<220> FEATURE:
<223> OTHER INFORMATION: Construct Oligonucleotide

<400> SEQUENCE: 9
tacagacgca gctgcttacg agatacgtcg tcgcgtgcgc gagtctggtt ctcaacgtga    60

<210> SEQ ID NO 10
<211> LENGTH: 45
<212> TYPE: DNA
<213> ORGANISM: Artificial Sequence
<220> FEATURE:
<223> OTHER INFORMATION: Construct Oligonucleotide

<400> SEQUENCE: 10
atggaagaaa acgttgattt ccgtattcac gttgagaacc agact                    45

<210> SEQ ID NO 11
<211> LENGTH: 73
<212> TYPE: DNA
<213> ORGANISM: Artificial Sequence
<220> FEATURE:
<223> OTHER INFORMATION: Construct Oligonucleotide

<400> SEQUENCE: 11
tacgctcagc tgctggttga gaccgacacc ttcggctccc aggtacgcat taaaggcaaa    60
gagactgaat tct                                                       73

<210> SEQ ID NO 12
<211> LENGTH: 57
<212> TYPE: DNA
<213> ORGANISM: Artificial Sequence
<220> FEATURE:
<223> OTHER INFORMATION: Construct Oligonucleotide

<400> SEQUENCE: 12
ttaccaacca gcttaccttt gcggttcatg cacaggtaga attcagtctc tttgcct       57

<210> SEQ ID NO 13
<211> LENGTH: 55
<212> TYPE: DNA
<213> ORGANISM: Artificial Sequence
<220> FEATURE:
<223> OTHER INFORMATION: Construct Oligonucleotide

<400> SEQUENCE: 13
```
tctgatgtct gcgaaataca gcggctggta cgttggtttc accaagaaag gtcgt    55

<210> SEQ ID NO 14
<211> LENGTH: 52
<212> TYPE: DNA
<213> ORGANISM: Artificial Sequence
<220> FEATURE:
<223> OTHER INFORMATION: Construct Oligonucleotide

<400> SEQUENCE: 14
tgtatttcgc agacatcaga gcggtgtagt tgttctccag aactttctcg at    52

<210> SEQ ID NO 15
<211> LENGTH: 80
<212> TYPE: DNA
<213> ORGANISM: Artificial Sequence
<220> FEATURE:
<223> OTHER INFORMATION: Construct Oligonucleotide

<400> SEQUENCE: 15
aggacgtgca cttcatgaaa cgttacccga aaggccagcc ggagctgcag aagccgttca    60
aatacaccac cgtgaccaaa    80

<210> SEQ ID NO 16
<211> LENGTH: 72
<212> TYPE: DNA
<213> ORGANISM: Artificial Sequence
<220> FEATURE:
<223> OTHER INFORMATION: Construct Oligonucleotide

<400> SEQUENCE: 16
ttcatgaagt gcacgtcctg ctggttctca cgggtcttcg gacctttacg cggacgacct    60
ttcttggtga aa    72

<210> SEQ ID NO 17
<211> LENGTH: 70
<212> TYPE: DNA
<213> ORGANISM: Artificial Sequence
<220> FEATURE:
<223> OTHER INFORMATION: Construct Oligonucleotide

<400> SEQUENCE: 17
aaggtaagct ggttggtaag ccggatggta cctccaaaga atgcgttttc atcgagaaag    60
ttctggagaa    70

<210> SEQ ID NO 18
<211> LENGTH: 54
<212> TYPE: DNA
<213> ORGANISM: Artificial Sequence
<220> FEATURE:
<223> OTHER INFORMATION: Construct Oligonucleotide

<400> SEQUENCE: 18
ttatgctgga tgagtcggac gaatacgacg agaacgtttg gtcacggtgg tgta    54

<210> SEQ ID NO 19
<211> LENGTH: 50
<212> TYPE: DNA
<213> ORGANISM: Artificial Sequence
<220> FEATURE:
<223> OTHER INFORMATION: Construct Oligonucleotide

<400> SEQUENCE: 19
ttgacaatta atcatcggct cgtataatgt gtggaattgt gagcggataa    50

<210> SEQ ID NO 20
<211> LENGTH: 42
<212> TYPE: DNA
<213> ORGANISM: Artificial Sequence
<220> FEATURE:
<223> OTHER INFORMATION: Construct Oligonucleotide

<400> SEQUENCE: 20
tctgatttaa tctgtatcag gctgaaaatc ttatctcatc cg         42

<210> SEQ ID NO 21
<211> LENGTH: 62
<212> TYPE: DNA
<213> ORGANISM: Artificial Sequence
<220> FEATURE:
<223> OTHER INFORMATION: Construct Oligonucleotide

<400> SEQUENCE: 21
gtggaattgt gagcggataa caatttcaca cagaattcat aaagaggag aaattaactc     60 cc                                                                  62

<210> SEQ ID NO 22
<211> LENGTH: 63
<212> TYPE: DNA
<213> ORGANISM: Artificial Sequence
<220> FEATURE:
<223> OTHER INFORMATION: Construct Oligonucleotide

<400> SEQUENCE: 22
gctgaaaatc ttatctcatc cgccaaaaca cccgggagtt aatttctcct ctttaatgaa    60
ttc                                                                  63

<210> SEQ ID NO 23
<211> LENGTH: 64
<212> TYPE: DNA
<213> ORGANISM: Artificial Sequence
<220> FEATURE:
<223> OTHER INFORMATION: Construct Oligonucleotide

<400> SEQUENCE: 23
acaatttcac acagaattca ttaaagagga gaaattaact atggatatta atactgaaac    60
tgag                                                                 64

<210> SEQ ID NO 24
<211> LENGTH: 64
<212> TYPE: DNA
<213> ORGANISM: Artificial Sequence
<220> FEATURE:
<223> OTHER INFORMATION: Construct Oligonucleotide

<400> SEQUENCE: 24
tctgtatcag gctgaaaatc ttatctcatc cgccaaaaca tcatcgccat tgctccccaa    60
atac                                                                 64

<210> SEQ ID NO 25
<211> LENGTH: 1965
<212> TYPE: DNA
<213> ORGANISM: Artificial Sequence
<220> FEATURE:
<223> OTHER INFORMATION: Red recombinase operon

<400> SEQUENCE: 25

```
acaatttcac acagaattca ttaaagagga gaaattaact atggatatta atactgaaac    60
tgagatcaag caaaagcatt cactaacccc ctttcctgtt ttcctaatca gcccggcatt   120
tcgcgggcga tattttcaca gctatttcag gagttcagcc atgaacgctt attacattca   180
ggatcgtctt gaggctcaga gctgggcgcg tcactaccag cagctcgccc gtgaagagaa   240
agaggcagaa ctggcagacg catggaaaa aggcctgccc cagcacctgt ttgaatcgct    300
atgcatcgat catttgcaac gccacggggc cagcaaaaaa tccattaccc gtgcgtttga   360
tgacgatgtt gagtttcagg agcgcatggc agaacacatc cggtacatgg ttgaaaccat   420
tgctcaccac caggttgata ttgattcaga ggtataaaac gaatgagtac tgcactcgca   480
acgctggctg ggaagctggc tgaacgtgtc ggcatggatt ctgtcgaccc acaggaactg   540
atcaccactc ttcgccagac ggcatttaaa ggtgatgcca gcgatgcgca gttcatcgca   600
ttactgatcg ttgccaacca gtacggcctt aatccgtgga cgaaagaaat ttacgccttt   660
cctgataagc agaatggcat cgttccggtg gtgggcgttg atggctggtc cgcatcatc    720
aatgaaaacc agcagtttga tggcatggac tttgagcagg acaatgaatc ctgtacatgc   780
cggatttacc gcaaggaccg taatcatccg atctgcgtta ccgaatggat ggatgaatgc   840
cgccgcgaac cattcaaaac tcgcgaaggc agagaaatca cggggccgtg gcagtcgcat   900
cccaaacgga tgttacgtca taagccatg attcagtgtg cccgtctggc cttcggattt    960
gctggtatct atgacaagga tgaagccgag cgcattgtcg aaaatactgc atacactgca  1020
gaacgtcagc cggaacgcga catcactccg gttaacgatg aaaccatgca ggagattaac  1080
actctgctga tcgccctgga taaaacatgg gatgacgact tattgccgct ctgttcccag  1140
atatttcgcc gcgacattcg tgcatcgtca gaactgacac aggccgaagc agtaaaagct  1200
cttggattcc tgaaacagaa agccgcagag cagaaggtgg cagcatgaca ccggacatta  1260
tcctgcagcg taccgggatc gatgtgagag ctgtcgaaca gggggatgat gcgtggcaca  1320
aattacggct cggcgtcatc accgcttcag aagttcacaa cgtgatagca aaaccccgct  1380
ccggaaagaa gtggcctgac atgaaaatgt cctacttcca cccctgctt gctgaggttt   1440
gcaccggtgt ggctccggaa gttaacgcta aagcactggc ctggggaaaa cagtacgaga  1500
acgacgccag aaccctgttt gaattcactt ccggcgtgaa tgttactgaa tccccgatca  1560
tctatcgcga cgaaagtatg cgtaccgcct gctctcccga tggtttatgc agtgacggca  1620
acggccttga actgaaatgc ccgtttacct cccgggattt catgaagttc cggctcggtg  1680
gtttcgaggc cataaagtca gcttacatgg cccaggtgca gtacagcatg tgggtgacgc  1740
gaaaaaatgc ctggtacttt gccaactatg acccgcgtat gaagcgtgaa ggcctgcatt  1800
atgtcgtgat tgagcgggat gaaaagtaca tggcgagttt tgacgagatc gtgccggagt  1860
tcatcgaaaa aatggacgag gcactggctg aaattggttt tgtatttggg gagcaatggc  1920
gatgatgttt tggcggatga gataagattt tcagcctgat acaga                  1965
```

<210> SEQ ID NO 26
<211> LENGTH: 92
<212> TYPE: DNA
<213> ORGANISM: Artificial Sequence
<220> FEATURE:
<223> OTHER INFORMATION: Construct oligonucleotide

<400> SEQUENCE: 26

```
attgttacat tgaaatggct agttattccc cggggcgatt ttcacctcgg ggaaatttta    60
gttggcgttc tcaggtcgag gtggcccggc tc                                  92
```

<210> SEQ ID NO 27
<211> LENGTH: 99
<212> TYPE: DNA
<213> ORGANISM: Artificial Sequence
<220> FEATURE:
<223> OTHER INFORMATION: Construct oligonucleotide

<400> SEQUENCE: 27

```
taattgactc attaagttag atataaaaaa tacatattca atcattaaaa cgattgaatg      60
gagaactttt attattgaag catttatcag ggttattgt                            99
```

<210> SEQ ID NO 28
<211> LENGTH: 1591
<212> TYPE: DNA
<213> ORGANISM: Artificial Sequence
<220> FEATURE:
<223> OTHER INFORMATION: tetracycline resistence fragment

<400> SEQUENCE: 28

```
taattgactc attaagttag atataaaaaa tacatattca atcattaaaa cgattgaatg      60
gagaactttt attattgaag catttatcag ggttattgtc tcatgagcgg atacatattt    120
gaatgtattt agaaaaataa acaaataggg gttccgcgca catttccccg aaaagtgcca    180
cctgacgtct aagaaaccat tattatcatg acattaacct ataaaaatag gcgtatcacg    240 aggcctctc atgtttgaca gcttatcatc gataagcttt aatgcggtag tttatcacag    300
ttaaattgct aacgcagtca ggcaccgtgt atgaaatcta acaatgcgct catcgtcatc    360
ctcggcaccg tcaccctgga tgctgtaggc ataggcttgg ttatgccggt actgccgggc    420
ctcttgcggg atatcgtcca ttccgacagc atcgccagtc actatggcgt gctgctagcg    480
ctatatgcgt tgatgcaatt tctatgcgca cccgttctcg gagcactgtc cgaccgcttt    540
ggccgccgcc cagtcctgct cgcttcgcta cttggagcca ctatcgacta cgcgatcatg    600
gcgaccacac ccgtcctgtg gatcctctac gccggacgca tcgtggccgg catcaccggc    660
gccacaggtg cggttgctgg cgcctatatc gccgacatca ccgatgggga agatcgggct    720
cgccacttcg ggctcatgag cgcttgtttc ggcgtgggta tggtggcagg ccccgtggcc    780
gggggactgt tgggcgccat ctccttgcat gcaccattcc ttgcggcggc ggtgctcaac    840
ggcctcaacc tactactggg ctgcttccta atgcaggagt cgcataaggg agagcgtcga    900
ccgatgccct tgagagcctt caacccagtc agctccttcc ggtgggcgcg gggcatgact    960
atcgtcgccg cacttatgac tgtcttcttt atcatgcaac tcgtaggaca ggtgccggca   1020
gcgctctggg tcattttcgg cgaggaccgc tttcgctgga gcgcgacgat gatcggcctg   1080
tcgcttgcgg tattcggaat cttgcacgcc ctcgctcaag ccttcgtcac tggtcccgcc   1140
accaaacgtt tcggcgagaa gcaggccatt atcgccggca tggcggccga cgcgctgggc   1200
tacgtcttgc tggcgttcgc gacgcgaggc tggatggcct tccccattat gattcttctc   1260
gcttccggcg gcatcgggat gcccgcgttg caggccatgc tgtccaggca ggtagatgac   1320
gaccatcagg gacagcttca aggatcgctc gcggctctta ccagcctaac ttcgatcact   1380
ggaccgctga tcgtcacggc gatttatgcc gcctcggcga gcacatggaa cgggttggca   1440
tggattgtag gcgccgccct ataccttgtc tgcctccccg cgttgcgtcg cggtgcatgg   1500
agccgggcca cctcgacctg agaacgccaa ctaaaatttc ccgaggtgaa aatcgcccc   1560 gggaataaac tagccatttc aatgtaacaa t                                  1591
```

<210> SEQ ID NO 29
<211> LENGTH: 32
<212> TYPE: DNA
<213> ORGANISM: Artificial Sequence
<220> FEATURE:
<223> OTHER INFORMATION: Construct oligonucleotide

<400> SEQUENCE: 29
tcattaagtt agatataaaa aatacatatt ca                               32

<210> SEQ ID NO 30
<211> LENGTH: 29
<212> TYPE: DNA
<213> ORGANISM: Artificial Sequence
<220> FEATURE:
<223> OTHER INFORMATION: Construct oligonucleotide

<400> SEQUENCE: 30
taattgttac attgaaatgg ctagttatt                                   29

<210> SEQ ID NO 31
<211> LENGTH: 27
<212> TYPE: DNA
<213> ORGANISM: Artificial Sequence
<220> FEATURE:
<223> OTHER INFORMATION: Construct oligonucleotide

<400> SEQUENCE: 31
atgaaatcta acaatgcgct catcgtc                                     27

<210> SEQ ID NO 32
<211> LENGTH: 22
<212> TYPE: DNA
<213> ORGANISM: Artificial Sequence
<220> FEATURE:
<223> OTHER INFORMATION: Construct oligonucleotide

<400> SEQUENCE: 32
tcaggtcgag gtggcccggc tc                                          22

<210> SEQ ID NO 33
<211> LENGTH: 27
<212> TYPE: DNA
<213> ORGANISM: Artificial Sequence
<220> FEATURE:
<223> OTHER INFORMATION: Construct oligonucleotide

<400> SEQUENCE: 33
tctaccgaga ctttatcgtt tactcct                                     27

<210> SEQ ID NO 34
<211> LENGTH: 28
<212> TYPE: DNA
<213> ORGANISM: Artificial Sequence
<220> FEATURE:
<223> OTHER INFORMATION: Construct oligonucleotide

<400> SEQUENCE: 34
ttaaaatgtg tacttaagac cagcagta                                    28

<210> SEQ ID NO 35
<211> LENGTH: 1585
<212> TYPE: DNA
<213> ORGANISM: Artificial Sequence
<220> FEATURE:
<223> OTHER INFORMATION: amplified band

<400> SEQUENCE: 35

```
tcattaagtt agatataaaa aatacatatt caatcattaa aacgattgaa tggagaactt      60
ttattattga agcatttatc agggttattg tctcatgagc ggatacatat ttgaatgtat     120
ttagaaaaat aaacaaatag gggttccgcg cacatttccc cgaaaagtgc cacctgacgt     180
ctaagaaacc attattatca tgacattaac ctataaaaat aggcgtatca cgaggccttc     240
tcatgtttga cagcttatca tcgataagct ttaatgcggt agtttatcac agttaaattg     300
ctaacgcagt caggcaccgt gtatgaaatc taacaatgcg ctcatcgtca tcctcggcac     360
cgtcaccctg gatgctgtag gcataggctt ggttatgccg gtactgccgg gcctcttgcg     420
ggatatcgtc cattccgaca gcatcgccag tcactatggc gtgctgctag cgctatatgc     480
gttgatgcaa tttctatgcg cacccgttct cggagcactg tccgaccgct ttggccgccg     540
cccagtcctg ctcgcttcgc tacttggagc cactatcgac tacgcgatca tggcgaccac     600
acccgtcctg tggatcctct acgccggacg catcgtggcc ggcatcaccg cgccacagg     660
tgcggttgct ggcgcctata tcgccgacat caccgatggg gaagatcggg ctcgccactt     720
cgggctcatg agcgcttgtt tcggcgtggg tatggtggca ggccccgtgg ccgggggact     780
gttgggcgcc atctccttgc atgcaccatt ccttgcggcg gcggtgctca acggcctcaa     840
cctactactg ggctgcttcc taatgcagga gtcgcataag ggagagcgtc gaccgatgcc     900
cttgagagcc ttcaacccag tcagctcctt ccggtgggcg cggggcatga ctatcgtcgc     960
cgcacttatg actgtcttct ttatcatgca actcgtagga caggtgccgg cagcgctctg    1020
ggtcattttc ggcgaggacc gctttcgctg gagcgcgacg atgatcggcc tgtcgcttgc    1080
ggtattcgga atcttgcacg ccctcgctca agccttcgtc actggtcccg ccaccaaacg    1140
tttcggcgag aagcaggcca ttatcgccgg catggcggcc gacgcgctgg gctacgtctt    1200
gctggcgttc gcgacgcgag gctggatggc cttccccatt atgattcttc tcgcttccgg    1260
cggcatcggg atgcccgcgt tgcaggccat gctgtccagg caggtagatg acgaccatca    1320
gggacagctt caaggatcgc tcgcggctct taccagccta acttcgatca ctggaccgct    1380
gatcgtcacg gcgatttatg ccgcctcggc gagcacatgg aacgggttgg catggattgt    1440
aggcgccgcc ctataccttg tctgcctccc cgcgttgcgt cgcggtgcat ggagccgggc    1500
cacctcgacc tgagaacgcc aactaaaatt cccccgaggt gaaaatcgcc ccggggaata    1560
actagccatt tcaatgtaac aatta                                            1585
```

<210> SEQ ID NO 36
<211> LENGTH: 1191
<212> TYPE: DNA
<213> ORGANISM: Artificial Sequence
<220> FEATURE:
<223> OTHER INFORMATION: Amplified band

<400> SEQUENCE: 36

```
atgaaatcta acaatgcgct catcgtcatc ctcggcaccg tcaccctgga tgctgtaggc      60
ataggcttgg ttatgccggt actgccgggc ctcttgcggg atatcgtcca ttccgacagc     120
atcgccagtc actatggcgt gctgctagcg ctatatgcgt tgatgcaatt tctatgcgca     180
cccgttctcg gagcactgtc cgaccgcttt ggccgccgcc cagtcctgct cgcttcgcta     240
cttggagcca ctatcgacta cgcgatcatg gcgaccacac ccgtcctgtg gatcctctac     300
gccggacgca tcgtggccgg catcaccggc gccacaggtg cggttgctgg cgcctatatc     360
```

```
gccgacatca ccgatgggga agatcgggct cgccacttcg ggctcatgag cgcttgtttc    420
ggcgtgggta tggtggcagg ccccgtggcc gggggactgt tgggcgccat ctccttgcat    480
gcaccattcc ttgcggcggc ggtgctcaac ggcctcaacc tactactggg ctgcttccta    540
atgcaggagt cgcataaggg agagcgtcga ccgatgccct tgagagcctt caacccagtc    600
agctccttcc ggtgggcgcg ggcatgact atcgtcgccg cactatgac tgtcttcttt      660 atcatgcaac tcgtaggaca ggtgccggca gcgctctggg tcattttcgg cgaggaccgc    720
tttcgctgga gcgcgacgat gatcggcctg tcgcttgcgg tattcggaat cttgcacgcc    780
ctcgctcaag ccttcgtcac tggtcccgcc accaaacgtt tcggcgagaa gcaggccatt    840
atcgccggca tggcggccga cgcgctgggc tacgtcttgc tggcgttcgc gacgcgaggc    900
tggatggcct tccccattat gattcttctc gcttccggcg gcatcgggat gcccgcgttg    960
caggccatgc tgtccaggca ggtagatgac gaccatcagg gacagcttca aggatcgctc   1020
gcggctctta ccagcctaac ttcgatcact ggaccgctga tcgtcacggc gatttatgcc   1080
gcctcggcga gcacatggaa cgggttggca tggattgtag gcgccgccct ataccttgtc   1140
tgcctccccg cgttgcgtcg cggtgcatgg agccgggcca cctcgacctg a            1191

<210> SEQ ID NO 37
<211> LENGTH: 93
<212> TYPE: DNA
<213> ORGANISM: artificial sequence
<220> FEATURE:
<223> OTHER INFORMATION: Construct Oligonucleotide

<400> SEQUENCE: 37
aatattatct tatctttata ataatcattc tcgtttacgt tatcattcac tttacatcag     60
agatatacca tgatgtccgg cggtgctttt gcc                                  93

<210> SEQ ID NO 38
<211> LENGTH: 93
<212> TYPE: DNA
<213> ORGANISM: Artificial Sequence
<220> FEATURE:
<223> OTHER INFORMATION: Construct Oligonucleotide

<400> SEQUENCE: 38
tgattcgtgt attcctgcat aacagccaac ttgtgaaatg ggcacggaaa tccgtgcccc     60
aaaagagaaa ttacgccccg ccctgccact cat                                  93

<210> SEQ ID NO 39
<211> LENGTH: 29
<212> TYPE: DNA
<213> ORGANISM: Artificial Sequence
<220> FEATURE:
<223> OTHER INFORMATION: Construct oligonucleotide

<400> SEQUENCE: 39
cattctcgtt tacgttatca ttcacttta                                       29

<210> SEQ ID NO 40
<211> LENGTH: 25
<212> TYPE: DNA
<213> ORGANISM: Artificial Sequence
<220> FEATURE:
<223> OTHER INFORMATION: Construct Oligonucleotide
```

-continued

```
<400> SEQUENCE: 40
cctgcataac agccaacttg tgaaa                                            25
```